United States Patent [19]

Atwal et al.

[11] Patent Number: 5,202,330
[45] Date of Patent: Apr. 13, 1993

[54] 2-THIO OR OXO-4-ARYL OR HETEROCYCLO-1,5(2H)-PYRIMIDINEDICARBOXYLIC ACID DIESTERS AND 3-ACYL-5-PYRIMIDINECARBOXYLIC ACIDS AND ESTERS

[75] Inventors: Karnail Atwal, Cranbury; George C. Rovnyak, Hopewell; Spencer D. Kimball, East Windsor, all of N.J.

[73] Assignee: E. R. Squibb & Sons, Inc., Princeton, N.J.

[21] Appl. No.: 618

[22] Filed: Jan. 5, 1987

Related U.S. Application Data

[63] Continuation-in-part of Ser. No. 864,687, May 19, 1986, abandoned, which is a continuation-in-part of Ser. No. 740,800, Jun. 3, 1985, abandoned, and Ser. No. 839,860, Mar. 14, 1986, abandoned.

[51] Int. Cl.$^5$ .................. A61K 31/495; C07D 239/22
[52] U.S. Cl. .................. 514/274; 544/316; 544/317; 544/318; 514/255
[58] Field of Search .................. 544/316, 317, 318; 514/274, 255

[56] References Cited

U.S. PATENT DOCUMENTS

| | | | |
|---|---|---|---|
| 4,048,171 | 9/1977 | Bossert et al. | 544/316 |
| 4,572,908 | 2/1966 | Campbell et al. | 514/340 |
| 4,609,494 | 9/1986 | Baldwin et al. | 544/316 |
| 4,640,922 | 2/1987 | Cho et al. | 544/316 |
| 4,675,321 | 6/1987 | Baldwin et al. | 544/316 |
| 4,683,234 | 7/1987 | Cho et al. | 544/316 |
| 4,684,655 | 8/1987 | Atwal | 544/316 |
| 4,684,656 | 8/1987 | Atwal | 544/316 |
| 4,689,414 | 8/1987 | Atwal | 544/316 |

FOREIGN PATENT DOCUMENTS

| | | | |
|---|---|---|---|
| 157219 | 10/1985 | European Pat. Off. | 544/316 |
| 0204317 | 1/1986 | European Pat. Off. | 544/316 |
| 3234684 | 1/1984 | Fed. Rep. of Germany | 544/316 |
| 0190974 | 10/1984 | Japan | 544/316 |
| 228281 | 2/1985 | Japan | 544/316 |
| 868030 | 5/1961 | United Kingdom | 544/316 |

OTHER PUBLICATIONS

J. Org. Chem., vol. 50, pp. 4227–4230, Cho et al.—"Synthesis of Novel Dihydropyrimidines and Tetra-hydropyrimidines", (1978).

Khanina et al., Khim. Farm. Zh., vol. 12, pp. 1321-1322 (1978) "Synthesis and Pharmacological Investigation . . .".

George et al., Synthesis (1975) pp. 405–407, "Condensed Heterocycles from 5-Ethoxycarbonyl-6-methyltetra hydropyrimidine-2-ones".

Sweet et al., J. Amer. Chem. Soc., vol. 95, pp. 8741–8749 (1973), "On the Synthesis of 3,4-Dihydro-2(1H)-pyrimidones . . .".

Konyukhov et al., Zh. Organ. Khim., vol. 1, No. 8, pp. 1487–1489 (1965), "Synthesis and Investigation . . .".

Folkers et al., J. Am. Chem. Soc., vol. 56, pp. 1374–1377, (1934) "Researches on Pyrimidines . . .".

Goerlitzer et al., Arch. Pharm. vol. 314, pp. 938–949 (1981).

(List continued on next page.)

*Primary Examiner*—Johann Richter
*Attorney, Agent, or Firm*—Stephen B. Davis

[57] ABSTRACT

Pyrimidine compounds of the formula $$\begin{array}{c} R_4 \quad H \\ \diagdown \diagup \\ O \quad C \quad O \\ \| \quad \diagup \diagdown \quad \| \\ Y-C-N \quad C-C-O-R_3 \\ \quad | \quad \| \\ \quad C \quad C-R_2 \\ \diagup \diagdown \diagup \\ X \quad N \\ \quad | \\ \quad H \end{array}$$

wherein X is sulfur or oxygen, Y is $R_{11}$ or $-O-R_1$, and $R_4$ is aryl or heterocyclo are disclosed. These compounds are useful as cardiovascular agents, particularly anti-hypertensive agents, due to their calcium entry blocking vasodilator activity.

30 Claims, No Drawings

OTHER PUBLICATIONS

Burger, Medicinal Chemistry, 2nd Ed., 1960, pp. 551–564, 572–578, 582–591, 606–620.

Derwent, 87-15 2482/22, Apr. 22, 1987.

Elkasaby, Pakistan J.Sci.Ind.Res., vol. 21, No. 2, pp. 58–61 (1978), "Condensation of Ethyl α-Acetylcinnametes With Thioureas".

George et al., Synthesis (1975) pp. 405–407, Condensed Heterocycles from 5-Ethoxycarbonyl-6-methyltetrahydropyrimidin-2-ones.

Zidermane et al., "Antitumor Action of Dihydropyridine and Dihydropyrimidine Derivatives", Chem. Abst., 75, 47266e (1971).

Iwanami et al., "N-Substituted-1,4-Dihydropyridine Derivatives", Chem. Abst., 86, 43570d (1977).

Goerlitzer et al., Chem. Abst., 96, 85501u (1982).

Stolefuss, "Dihydropyrimidines Useful In Treating Circulatory Ailments" Chem. Abst. 101, 55110v (1984).

Merck Index, 10th Ed., "Nifedipine" 6374, (1983).

Bianchi et al., "Long Lasting Anti-hypertensive Effects . . . " IRCS Med. Sci., vol. 14, pp. 817–818 (1986).

Tamazawa et al., "Stereoselectivity of a Potent Calcium Antagonist . . . ", J. Med. Chem., vol. 29, pp. 2504–2511 (1986).

Goodman et al. The Pharmacological Basis of Therapeutics, 6 ed., p. 28.

2-THIO OR OXO-4-ARYL OR HETEROCYCLO-1,5(2H)-PYRIMIDINEDICARBOXYLIC ACID DIESTERS AND 3-ACYL-5-PYRIMIDINECARBOXYLIC ACIDS AND ESTERS

RELATED APPLICATIONS

This application is a continuation-in-part of U.S. Ser. No. 864,687 filed May 19, 1986 now abandoned, which was a continuation-in-part of U.S. Ser. No. 740,800, filed Jun. 3, 1985, now abandoned, and U.S. Ser. No. 839,860, filed Mar. 14, 1986, now abandoned.

BACKGROUND OF THE INVENTION

Baldwin et al. in U.S. Pat. No. 4,609,494 disclose cardiovascular agents of the formula

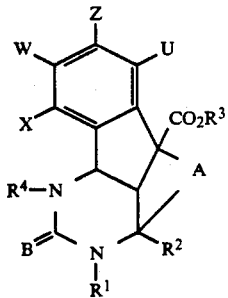

wherein A and B are oxygen or sulfur; $R^2$ is hydrogen, alkyl, cycloalkyl, etc.; $R^3$ is alkyl, cycloalkyl, hydroxyalkyl, alkoxyalkyl, alkoxy (alkoxyalkyl), aminoalkyl, etc.; $R^4$ is COY wherein Y is alkyl, alkoxy, cycloalkyl or $NR^5R^6$; $R^5$ and $R^6$ are hydrogen, alkyl, phenylalkyl, or together complete a heterocycle; and X, W, Z and U are hydrogen, alkyl, alkoxy, alkylthio, $CF_3$, nitro, halo or

These compounds are prepared by cyclizing an intermediate of the formula

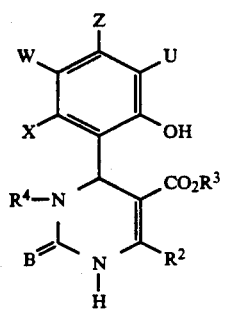

or of the formula

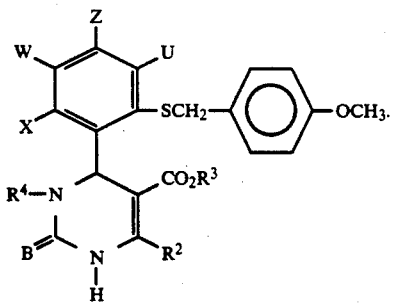

Stoltefuss et al. in German Offenlegungsschrift 3,234,684 A 1 disclose dihydropyrimidines of the formula

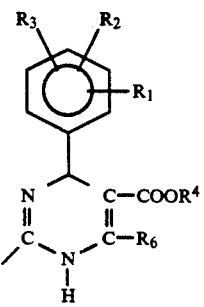

where $R^5$ is hydrogen, alkyl, substituted alkyl, phenyl, etc. These compounds are disclosed as possessing cardiovascular activity.

Khanina et al., Khim. Farm. Zh., Vol. 12 pages 1321–1323 (1978) report some hypotensive activity for 4-aryl-2-oxo-pyrimidines of the formula

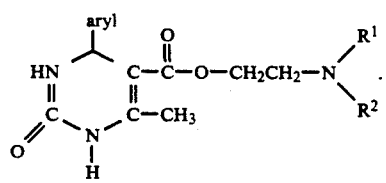

Konyukhov et al., Zh. Organ. Khim., Vol. 1, No. 8, pages 1487–1489 (1965) disclose antitumorigenic and antiviral dihydropyrimidines of the formula

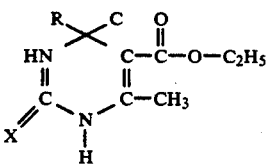

wherein X is oxygen or sulfur and R is aryl or heterocyclo.

SUMMARY OF THE INVENTION

This invention relates to the use of the pyrimidine compounds of formula I and pharmaceutically acceptable salts thereof as cardiovascular agents

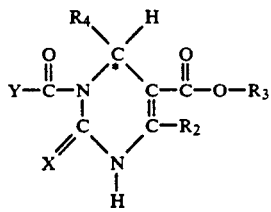

X is oxygen or sulfur.
Y is $R_{11}$ or —O—$R_1$.

$R_1$ is lower alkyl, aryl, cycloalkyl, -$A_1$-aryl, -$A_1$-cycloalkyl, -$A_1$-heterocyclo, -$A_2$-OH, -$A_2$-O-lower alkyl, -$A_2$-O—$(CH_2)_m$-aryl, -$A_2$-SH, -$A_2$-S-lower alkyl, -$A_2$-S-$(CH_2)_m$-aryl,

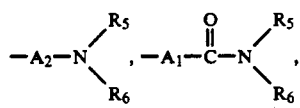

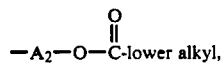

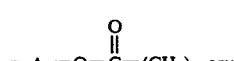

halo substituted lower alkyl, or

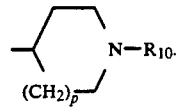

$R_2$ is hydrogen, lower alkyl, lower alkenyl, lower alkynyl, cycloalkyl, aryl, -$A_1$-cycloalkyl, -$A_1$-aryl, -$A_1$-heterocyclo, -$A_1$—OH, -$A_1$—O-lower alkyl, -$A_1$—O—$(CH_2)_m$-aryl, -$A_1$—SH, -$A_1$—S-lower alkyl, -$A_1$—S—$(CH_2)_m$-aryl,

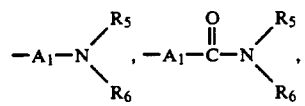

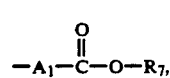

or halo substituted lower alkyl.

$R_3$ is hydrogen, lower alkyl, aryl, cycloalkyl, -$A_1$-aryl, -$A_1$-cycloalkyl, -$A_1$-heterocyclo, -$A_2$—OH, -$A_2$—O—lower alkyl, -$A_2$—O—$(CH_2)_m$-aryl, -$A_2$-SH, -$A_2$—S—lower alkyl, -$A_2$—S—$(CH_2)_m$—aryl,

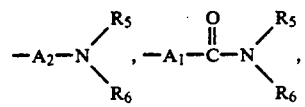

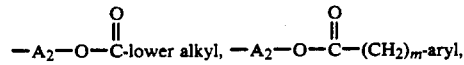

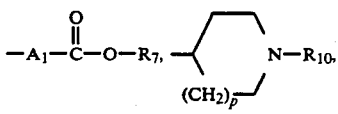

halo substituted lower alkyl, or a pharmaceutically acceptable salt forming ion.

$R_4$ is aryl or heterocyclo.

$R_5$ and $R_6$ are independently selected from the group consisting of hydrogen, lower alkyl, —$(CH_2)_m$—aryl,

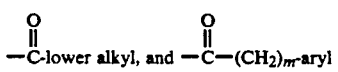

or $R_5$ and $R_6$ taken together with the N atom to which they are attached complete a heterocyclic ring of the formula

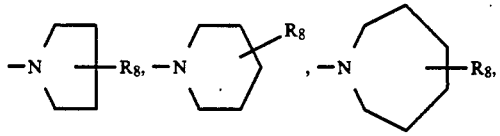

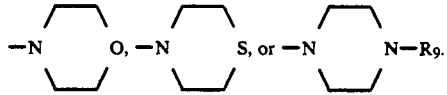

$R_7$ is hydrogen, lower alkyl, —$(CH_2)_m$—aryl, or a pharmaceutically acceptable salt forming ion.

$R_8$ is hydrogen, lower alkyl of 1 to 4 carbons, lower alkoxy of 1 to 4 carbons, lower alkylthio of 1 to 4 carbons, halo, $CF_3$, nitro, or hydroxy.

$R_9$ is hydrogen or lower alkyl of 1 to 4 carbons,

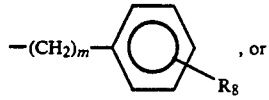

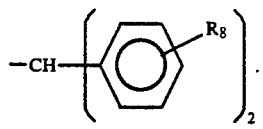

$R_{10}$ is lower alkyl of 1 to 4 carbons,

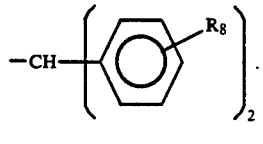

$R_{11}$ is lower alkyl, aryl, cycloalkyl, heterocyclo, -$A_1$-aryl, -$A_1$-cycloalkyl, -$A_1$-heterocyclo, -$A_1$-OH, -$A_1$-O- lower alkyl, $-A_1-O-(CH_2)_m$-aryl, $-A_1-SH$, $-A_1-S$-lower alkyl, $-A_1-S-(CH_2)_m$-aryl,

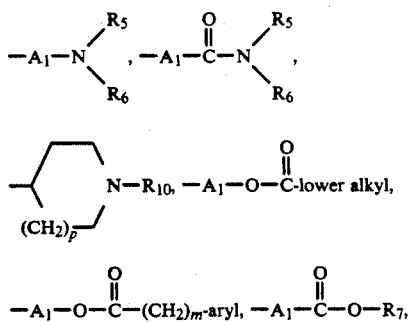

$A_1$ is

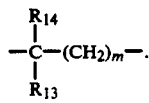

$A_2$ is

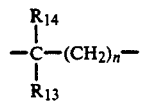

m is zero or an integer from 1 to 6.
n is an integer from 1 to 6.
p is zero, one or two.
$R_{13}$ and $R_{14}$ are independently selected from hydrogen, lower alkyl of 1 to 4 carbons,

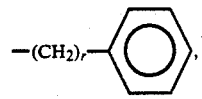

or $-(CH_2)_r$-cycloalkyl.
r is zero or an integer from 1 to 3.

This invention is also directed to the novel pyrimidine compounds of formula I wherein $R^4$ is mono substituted phenyl wherein said substituent is selected from lower alkyl 1 to 4 carbons, halo, $CF_3$, and nitro, disubstituted phenyl wherein said substituents are selected from methyl, halo, $CF_3$, and nitro, or heterocyclo.

DETAILED DESCRIPTION OF THE INVENTION

This invention in its broadest aspects relates to the pyrimidine compounds of formula I above, to compositions and the method of using such compounds as cardiovascular agents.

The term lower alkyl used in defining various symbols refers to straight or branched chain hydrocarbon radicals having up to eight carbons, preferably from one to five carbons. Similarly, the terms lower alkoxy and lower alkylthio refer to such lower alkyl groups attached to an oxygen or sulfur.

The term lower alkenyl refers to straight or branched chain hydrocarbon radicals having from two to eight carbons and one double bond, preferably three to five carbons. The term lower alkynyl refers to straight or branched chain hydrocarbon radicals having from two to eight carbons and one triple bond, preferably three to five carbons.

The term cycloalkyl refers to saturated rings of 4 to 7 carbon atoms with cyclopentyl and cyclohexyl being most preferred.

The term halo refers to chloro, bromo and fluoro.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The term aryl refers to phenyl, 1-naphthyl, 2-naphthyl, mono substituted phenyl, 1-naphthyl, or 2-naphthyl wherein said substituent is lower alkyl of 1 to 4 carbons, lower alkylthio of 1 to 4 carbons, lower alkoxy of 1 to 4 carbons, halo, nitro, cyano, hydroxy, amino, $-NH$-alkyl wherein alkyl is of 1 to 4 carbons, $-N(alkyl)_2$ wherein alkyl is of 1 to 4 carbons, $CF_3$, NCS, $OCHF_2$,

$-O-CH_2$-cycloalkyl,

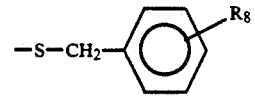

or $-S-CH_2$-cycloalkyl, and di-substituted phenyl, 1-naphthyl, or 2-naphthyl wherein said substituents are selected from methyl, methoxy, methylthio, halo, $CF_3$, nitro, amino, and $OCHF_2$.

The term heterocyclo refers to fully saturated or unsaturated monocyclic rings of 5 or 6 atoms containing one to four N atoms, or one O atom and up to two N atoms, or one S atom and up to two N atoms. The monocyclic ring is attached by way of an available carbon atom. Preferred monocyclic heterocyclo groups include 2- and 3-thienyl, 2- and 3-furyl, 2-, 3- and 4-pyridinyl, and imidazolyl. The term heterocyclo also includes bicyclic rings wherein the five or six membered monocyclic ring containing O, S and N atoms as defined above is fused to a benzene ring and the bicyclic ring is attached by way of an available carbon atom in the benzene ring. Preferred bicyclic heterocyclo groups include 4, 5, 6, or 7-indolyl, 4, 5, 6, or 7-isoindolyl, 5, 6, 7 or 8-quinolinyl, 5, 6, 7 or 8-isoquinolinyl, 4, 5, 6, or 7-benzothiazolyl, 4, 5, 6 or 7-benzoxazolyl, 4, 5, 6 or 7-benzimidazolyl, 4, 5, 6 or 7-benzoxadiazolyl, and 4, 5, 6 or 7-benzofurazanyl. The term heterocyclo also includes 2-, 3-, or 4-pyridinyl rings having a substituent on one available carbon selected from lower alkyl of 1 to 4 carbons, lower alkylthio of 1 to 4 carbons, and lower alkoxy of 1 to 4 carbons, especially 2-methylthio-3-pyridinyl.

The 2-oxo-1,5(2H)-pyrimidinedicarboxylic acid diesters of formula I, i.e., Y is $-O-R_1$ and X is oxygen, and the 2-oxo-3-acyl-5-pyrimidinedicarboxylic acid and esters of formula I, i.e., Y is $R_1$ and X is oxygen, can be prepared as follows.

A keto ester compound of the formula

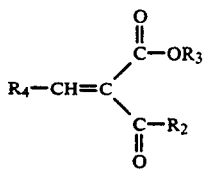

is treated with 2-methylpseudourea, i.e.,

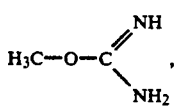

particularly the hydrogen sulfate salt thereof, in the presence of sodium acetate or sodium bicarbonate to give

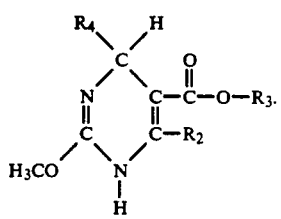

The 1,4-pyrimidinecarboxylic acid ester of formula III is treated with the chloroformate of the formula

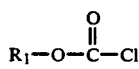

in the presence of an organic base such as pyridine or the dicarbonate of the formula

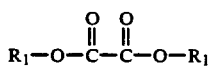

in the presence of an organic base such as 4-dimethylaminopyridine to give the 1,5(6H)-pyrimidinedicarboxylic acid diester of the formula

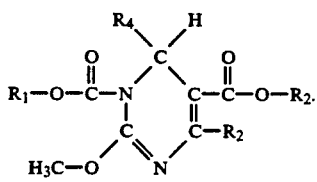

Similarly, the 1,4-pyrimidinecarboxylic acid ester of formula III is treated with the acyl chloride of the formula

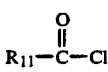

in the presence of an organic base such as pyridine to give the 5-pyrimidinecarboxylic acid ester of the formula

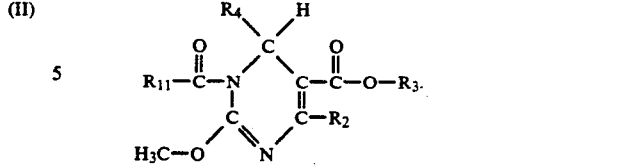

Treatment of the compound of formula VI with hydrochloric acid gives the 2-oxo-1,5(2H)-pyrimidinedicarboxylic acid diester of formula I. Similarly, treatment of the compound of formula VIII with hydrochloric acid gives the 2-oxo-3-acyl-5-pyrimidinecarboxylic acid of formula I.

The 2-thioxo-1,5(2H)-pyrimidinedicarboxylic acid diesters of formula I, i.e., Y is $-O-R_1$ and X is sulfur, and the 2-thioxo-3-acyl-5-pyrimidinecarboxylic acid and esters of formula I, i.e., Y is $R_1$ and X is sulfur, can be prepared as follows.

A keto ester compound of formula III is treated with S-(benzyl or 4-methoxybenzyl)thiopseudourea of the formula

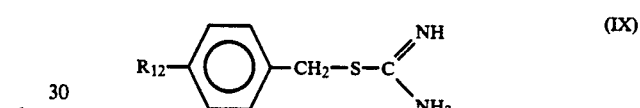
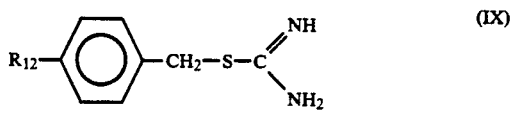

especially the hydrochloride salt thereof, wherein $R_{12}$ is hydrogen or methoxy. This reaction is carried out in the presence of sodium acetate and gives the 1,4-pyrimidinecarboxylic acid of the formula

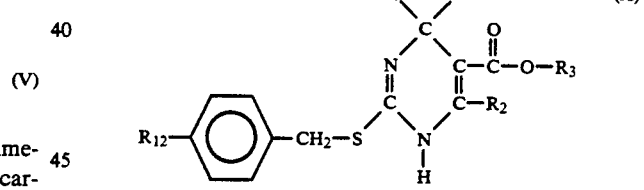

The 1,4-pyrimidinecarboxylic acid ester of formula X is then treated with the chloroformate of formula IV in the presence of an organic base such as pyridine to give the 1,5(6H)-pyrimidinedicarboxylic acid diester of the formula

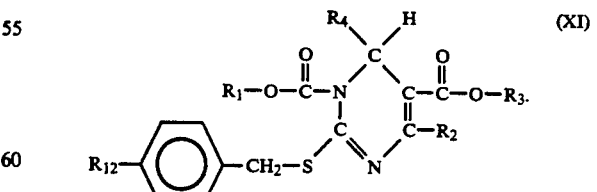
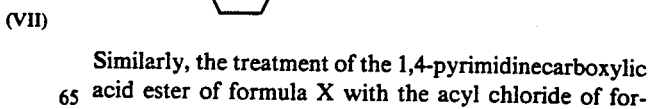

Similarly, the treatment of the 1,4-pyrimidinecarboxylic acid ester of formula X with the acyl chloride of formula VII in the presence of an organic base such as pyridine gives the 3-acyl-5-pyrimidinecarboxylic acid ester of the formula

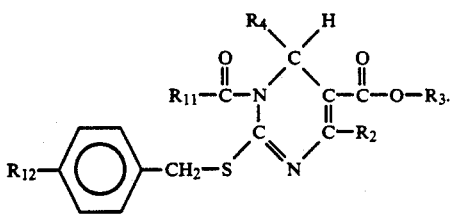

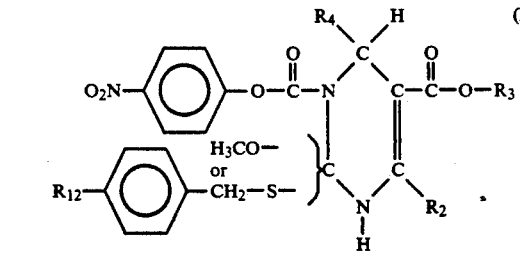

When $R_{12}$ is hydrogen, treatment of the intermediate of formula XI with bromotrimethylsilane gives the desired 1,5(2H)-pyrimidinedicarboxylic acid diester of formula I and similar treatment of the intermediate of formula XII gives the desired 3-acyl-5-pyrimidinecarboxylic acid ester of formula I. When $R_{12}$ is methoxy, treatment of the intermediate of formula XI with trifluoroacetic acid alone or in combination with ethanethiol gives the desired 1,5(2H)-pyrimidinedicarboxylic acid diester of formula I and similar treatment of the intermediate of formula XII gives the desired 3-acyl-5-pyrimidinecarboxylic acid ester.

Additionally, the 1,5(6H)-pyrimidinedicarboxylic acid diester of formulas VI or XI can be prepared by treating the 1,4-pyrimidinecarboxylic acid ester of formula III or X with phosgene followed by the alcohol of formula $R_1$—OH. (XIII)

This procedure is preferred when $R_1$ is

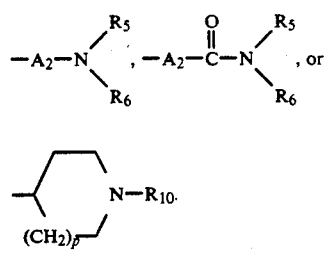

The compounds of formula I wherein Y is —O-$R_1$ can also be prepared by reacting the alcohol of formula XIII with 4-nitrophenyl chloroformate to give the reagent of the formula

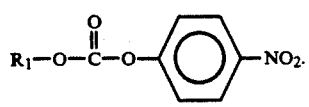
(XIV)

The reagent of formula XIV is then reacted with the 1,4-pyrimidinecarboxylic acid ester of formula III or X wherein $R_{12}$ is methoxy followed by treatment with hydrochloric acid to give the 2-oxo products or treatment with trifluoroacetic acid alone or in combination with ethanethiol to give the 2-thioxo products.

The compounds of formula I wherein Y is —O—$R_1$ can also be prepared by treating the 1,4-pyrimidinecarboxylic acid ester of formula III or X with 4-nitrophenyl chloroformate to give the intermediate of the formula The intermediate of formula XV is treated with hydrochloric acid or trifluoroacetic acid alone or in combination with ethanethiol, as described above, to give

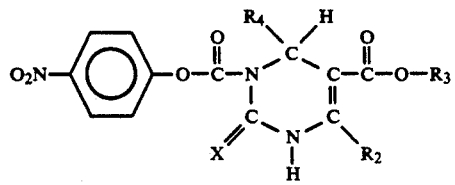

Treatment of the intermediate of formula XVI with the alcohol of formula XIII gives the desired compounds of formula I.

The above two processes are preferred for preparing branched products, i.e. at least one of $R_{13}$ and $R_{14}$ within the definition of $R_1$ is other than hydrogen.

Additionally, the 2-thioxo-1,5(2H)-pyrimidinedicarboxylic acid diesters of formula I can be prepared by reacting a 2-thioxo-5-pyrimidinecarboxylic acid ester of the formula

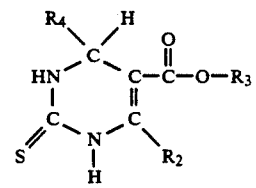

with the acid chloride of formula IV in the presence of pyridine

The 2-thioxo-5-pyrimidinecarboxylic acid ester starting material of formula XVII can be prepared by reacting an aldehyde of the formula $R_4$—CHO (XVIII)

with the keto ester of the formula

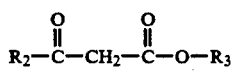
(XIX)

and thiourea.

The compounds of formula I contain an asymmetric center within the pyrimidine ring as represented by the *. Thus, the compounds of formula I can exist in stereoisomeric forms or in mixtures thereof. The above described processes can utilize racemates, enantiomers or diastereomers as starting materials. When diastereomeric products are prepared, they can be separated by conventional chromatographic or fractional crystallization methods.

For example, the 2-thioxo-1,5(2H)-pyrimidinedicarboxylic acid diesters of formula I can be prepared as a resolved product as follows. The 1,4-pyrimidinecarboxylic acid ester of formula X is reacted with phosgene followed by N-[(1,1-dimethylethoxy)carbonyl]-4-(trans-hydroxy)-L-proline, methyl ester in the presence of an organic base such as pyridine to give the unresolved intermediate of the formula

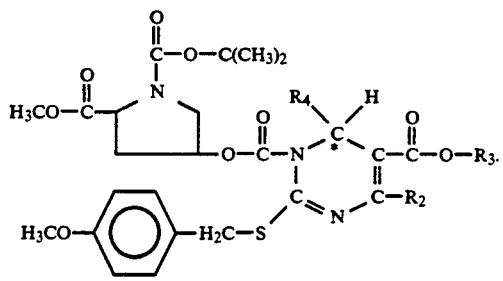 (XX)

The intermediate of formula XVII is treated with trifluoroacetic acid and anisole and the resulting 2-thioxo compound is resolved chromatographically to give

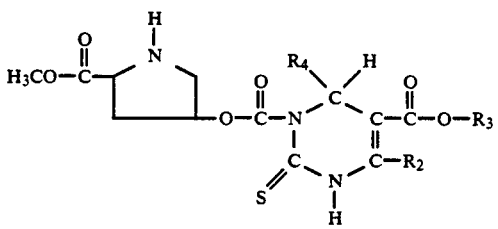 (XXI)

as isomers A and B.

The resolved intermediates of formula XXI can be hydrolyzed to give the resolved form of the 2-thioxo-5-pyrimidinecarboxylic acid of formula XVII. Reaction with the acid chloride of formula IV gives the resolved final product.

If any of $R_1$, $R_{11}$, $R_2$, $R_3$ and $R_4$ in the above are aryl, -$A_1$-aryl, or terminate in —$(CH_2)_m$-aryl wherein aryl is phenyl, 1-naphthyl, or 2-naphthyl substituted with one or more hydroxy or amino groups, heterocyclo, -$A_1$-heterocyclo or -$A_2$-heterocyclo wherein the heterocyclo ring contains an NH such as imidazolyl, or a substituted alkyl such as -$A_2$—OH, -$A_2$—$NH_2$, -$A_2$—SH, or

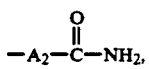

the hydroxyl, amino, or mercaptan function should be protected during the reaction. Suitable protecting groups include benzyloxycarbonyl, t-butoxycarbonyl, benzyl, benzhydryl, etc. The protecting group is removed by hydrogenation, treatment with acid, or by other known means following completion of the reaction.

Preferred 1,5(2H)-pyrimidinedicarboxylic acid compounds of formula I, i.e. Y is —O—$R_1$, are those wherein:

$R_1$ is straight or branched chain lower alkyl of 1 to 5 carbons, benzyl,

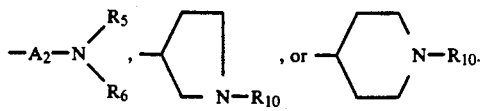

$R_2$ is straight or branched chain lower alkyl of 1 to 5 carbons, especially methyl.

$R_3$ is straight or branched chain lower alkyl of 1 to 5 carbons, benzyl,

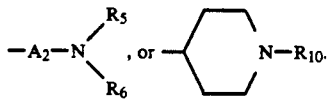

$R_4$ is mono substituted phenyl wherein said substituent is selected from lower alkyl of 1 to 4 carbons, halo, $CF_3$, or nitro, disubstituted phenyl wherein said substituents are selected from methyl, halo, $CF_3$ and nitro, 2-, 3-, or 4-pyridinyl, 2-methylthio-3-pyridinyl, or 2, 1, 3-benzoxadiazolyl.

$A_2$ is —$CH_2$—$(CH_2)_n$— or $$-\underset{\underset{CH_3}{|}}{CH}-(CH_2)_n-.$$

n is 1, 2 or 3.

$R_5$ and $R_6$ are independently selected from hydrogen, straight or branched chain lower alkyl of 1 to 5 carbons, and benzyl, or $R_5$ and $R_6$ taken together with the N atom to which they are attached complete a heterocyclic ring of the formula

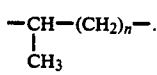

$R_9$ is methyl, benzyl, or diphenylmethyl.
$R_{10}$ is benzyl or diphenylmethyl.

Most preferred 1,5(2H)-pyrimidinedicarboxylic acids are those wherein:

$R_1$ is methyl, ethyl, isopropyl, benzyl,

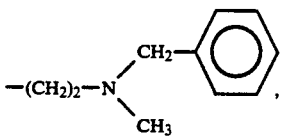

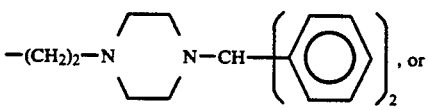

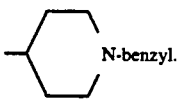

$R_3$ is ethyl, isopropyl, benzyl,

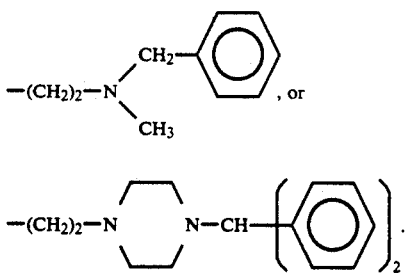

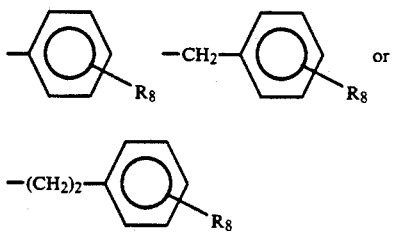

$R_4$ is 2-nitrophenyl, 3-nitrophenyl, 2-chlorophenyl, 3-chlorophenyl, 2-(trifluoromethyl)phenyl, 3-(trifluoromethyl)phenyl, 2,3-dichlorophenyl, 2-chloro-3-nitrophenyl, or 4-(2,1,3-benzoxadiazol)-yl.

Preferred 3-acyl-5-pyrimidinecarboxylic acids and esters of formula I, i.e., Y is $R_{11}$, are those wherein:

$R_{11}$ is straight or branched chain lower alkyl of 1 to 5 carbons,

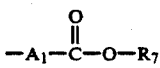

$R_2$ is straight or branched chain lower alkyl of 1 to 5 carbons, especially methyl.

$R_3$ is straight or branched chain lower alkyl of 1 to 5 carbons.

$R_4$ is mono substituted phenyl wherein said substituent is selected from lower alkyl of 1 to 4 carbons, halo, $CF_3$, and nitro, disubstituted phenyl wherein said substituents are selected from methyl, halo, $CF_3$, and nitro, or 2,1,3-benzoxadiazolyl, especially 3-nitrophenyl.

$R_8$ is hydrogen, methyl, methoxy, methylthio, halo, $CF_3$, nitro, or hydroxy

The compounds of formula I which contain an amino group form salts with a variety of inorganic and organic acids. The non-toxic pharmaceutically acceptable salts are preferred, although other salts may also be useful in isolating or purifying the product. Such pharmaceutically acceptable salts include those formed with hydrochloric acid, methanesulfonic acid, sulfuric acid, acetic acid, maleic acid, etc. The salts are obtained by reacting the product with an equivalent amount of the acid in a medium in which the salt precipitates.

In addition, the compounds of formula I in which $R_1$, $R_{11}$, $R_2$ or $R_3$ is $$-A_1-\overset{O}{\underset{\|}{C}}-O-R_7$$

or in which $R_3$ is hydrogen include carboxylic acid salts, i.e., $R_3$ or $R_7$ is a pharmaceutically acceptable salt forming ion. Preferred salt forming ions include alkali metal salt ions such as sodium, potassium and lithium, and alkaline earth metal salt ions such as calcium and magnesium.

The compounds of formula I and the pharmaceutically acceptable salts thereof are useful as cardiovascular agents. These compounds act as calcium entry blocking vasodilators and are especially useful as antihypertensive agents. Thus, by the administration of a composition containing one (or a combination) of the compounds of this invention the blood pressure of a hypertensive mammalian (e.g., human) host is reduced. A single dose, or preferably two to four divided daily doses, provided on a basis of about 0.1 to 100 mg. per kilogram of body weight per day, preferably from about 1 to about 50 mg. per kilogram per day, is appropriate to reduce blood pressure. The substance is preferably administered orally, but parenteral routes such as the subcutaneous, intramuscular, or intravenous routes can also be employed.

As a result of the calcium entry blocking activity of the compounds of formula I, it is believed that such compounds in addition to being anti-hypertensives may also be useful as anti-arrhythmic agents, as anti-anginal agents, as anti-fibrillatory agents, as anti-asthmatic agents, and in limiting myocardial infarction.

The compounds of this invention can also be formulated in combination with a diuretic, or a beta-adrenergic agent, or angiotensin converting enzyme inhibitor. Suitable diuretics include the thiazide diuretics such as hydrochlorothiazide and bendroflumethiazide, suitable beta-adrenergic agents include nadolol, and suitable angiotensin converting enzyme inhibitors include captopril.

The compounds of formula I can be formulated for use in the reduction of blood pressure in compositions such as tablets, capsules or elixirs for oral administration, or in sterile solutions or suspensions for parenteral administration. About 10 to 500 mg. of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples are illustrative of the invention. Temperatures are given in degrees centigrade.

EXAMPLE 1

3,6-Dihydro-4-methyl-6-(3-nitrophenyl)-2-thioxo-1,5(2H)-pyrimidinedicarboxylic, diethyl ester a) 1,2,3,4-Tetrahydro-6-methyl-4-(3-nitrophenyl)-2-thioxo-5-pyrimidinecarboxylic acid, ethyl ester A solution containing m-nitrobenzaldehyde (7.55 g., 50.0 mmole), ethylacetoacetate (6.5 g., 50.0 mmole), and thiourea (3.8 g., 50.0 mmole) in absolute ethanol (30 ml.) is treated with concentrated hydrochloric acid (0.2 ml.). The resulting reaction mixture is heated at reflux for 6 hours. It is then cooled to room temperature and triturated. A small amount of a white solid precipitates out. The reaction flask is then allowed to cool in the refrigerator overnight. The precipitate that forms is filtered off and washed with additional absolute ethanol to provide 2.5 g. of colorless solid product. Recrystallization from absolute ethanol gives an analytically pure sample of 1,2,3,4-tetrahydro-6-methyl-4-(3-nitrophenyl)-2-thioxo-5-pyrimidine-carboxylic acid, ethyl ester; m.p. 208°-209°. TLC (silica gel; ethyl acetate:hexanes, 1:1) $R_f = 0.45$.

Anal. calc'd. for $C_{14}H_{15}N_3O_4S$: C, 52.33; H, 4.71; N, 13.08; S, 9.98. Found: C, 52.28; H, 4.81; N, 13.10; S, 9.90.

b) 3,6-Dihydro-4-methyl-6-(3-nitrophenyl)-2-thioxo-1,5(2H)-pyrimidinedicarboxylic acid, diethyl ester A suspension of 1,2,3,4-tetrahydro-6-methyl-4-(3-nitrophenyl)-2-thioxo-5-pyrimidinecarboxylic acid, ethyl ester (3.0 g., 9.35 mmole) in dichloromethane (40 ml.) and tetrahydrofuran (10 ml.) is cooled to 0° and treated with pyridine (2 ml.) followed by the dropwise addition of ethyl chloroformate (1.58 g., 14.6 mmole). After the addition is complete, a yellow solution results. After stirring the reaction mixture at room temperature for one hour (TLC shows the presence of some starting material), it is diluted with ethyl acetate (250 ml.). The resulting solution is washed with water, 5% citric acid, sodium bicarbonate and brine. After drying over anhydrous magnesium sulfate, the solvent is stripped off to give a thick yellow oil. This oil is triturated with anhydrous ether whereby some starting material precipitates out. The precipitate is filtered off and the filtrate is concentrated and purified by flash chromatography (3% ethyl acetate in dichloromethane). The residue obtained, after evaporation of the solvent, is crystallized from isopropyl ether-hexanes to give 2.20 g. of 3,6-dihydro-4-methyl-6-(3-nitrophenyl)-2-thioxo-1,5(2H)-pyrimidinedicarboxylic acid, diethyl ester, m.p., 125.5°-127°. TLC (silica gel; ethyl acetate:hexanes, 40:60) $R_f$=0.43.

Anal. calc'd. for $C_{17}H_{19}N_3O_6S$: C, 51.90; H, 4.87; N, 10.68; S, 8.15. Found: C, 51.73; H, 4.80; N, 10.44; S, 7.93.

EXAMPLE 2

3,6-Dihydro-4-methyl-6-(3-nitrophenyl)-2-oxo-1,5(2H)-pyrimidinedicarboxylic acid, diethyl ester a) 1,4-Dihydro-2-methoxy-6-methyl-4-(3-nitrophenyl)-5-pyrimidinecarboxylic acid, ethyl ester A reaction mixture containing 2-[(3-nitrophenyl)methylene]-3-oxobutanoic acid, ethyl ester (2.62 g., 10.0 mmole), 2-methylpseudourea sulfate (1.72 g., 10.0 mmole), and sodium acetate (1.8 g., 22.0 mmole) in tetrahydrofuran (10 ml.) is heated under reflux for 4 hours. The reaction mixture is allowed to cool to room temperature, diluted with ethyl acetate, and filtered. The filtrate is washed with sodium bicarbonate and brine, and then dried over anhydrous magnesium sulfate. Evaporation of the solvent gives a yellow oil which is purified by flash chromatography (5% ethyl acetate in dichloromethane). The resulting foam is crystallized from isopropanolhexanes to provide 1.53 g. of 1,4-dihydro-2-methoxy-6-methyl-4-(3-nitrophenyl)-5-pyrimidinecarboxylic acid, ethyl ester as a colorless crystalline product; m.p. 103.5°-105°. TLC (silica gel; ethyl acetate:hexanes, 50:50) $R_f$=0.31.

Anal. calc'd. for $C_{15}H_{17}N_3O_5$: C, 56.42; H, 5.37; N, 13.16. Found: C, 56.52; H, 5.35; N, 13.03.

b) 3,6-Dihydro-4-methyl-6-(3-nitrophenyl)-2-oxo-1,5(2H)-pyrimidinedicarboxylic acid, diethyl ester A solution of 1,4-dihydro-2-methoxy-6-methyl-4-(3-nitrophenyl)-5-pyrimidinecarboxylic acid, ethyl ester (1.5 g., 4.7 mmole) in dichloromethane (15 ml.) and pyridine (0.4 ml.) is cooled to 0° and treated with ethyl chloroformate (537 mg. of 97%, 4.8 mmole). A white precipitate forms immediately. The reaction is allowed to stir at room temperature for 30 minutes and the solvent is stripped off. The residue is dissolved in methanol (10 ml.) and is treated with 2N hydrochloric acid (2 ml.). After stirring the reaction mixture at room temperature for 30 minutes, the solvent is stripped off. The residue is taken up in ethyl acetate and is washed with sodium bicarbonate and brine. After drying over anhydrous magnesium sulfate, the solvent is evaporated to provide a colorless foam. This foam is crystallized from isopropyl ether-hexanes to yield 1.64 g. of 3,6-dihydro-4-methyl-6-(3-nitro-phenyl)-2-oxo-1,5(2H)-pyrimidinedicarboxylic acid, diethyl ester as a colorless crystalline product; m.p. 107°-108.5°. TLC (silica gel; ethyl acetate: hexanes, 50:50) $R_f$=0.26.

Anal. calc'd. for: $C_{17}H_{19}N_3O_7$ C, 54.11; H, 5.08; N, 11.14. Found: C, 54.10; H, 5.06; N, 10.93.

EXAMPLE 3

3,6-Dihydro-4-methyl-6-(2,3-dichlorophenyl)-2-oxo-1,5(2H)-pyrimidinedicarboxylic acid, diethyl ester a) 1,4-Dihydro-2-methoxy-6-methyl-4-(2,3-dichlorophenyl)-5-pyrimidinecarboxylic acid, ethyl ester A solution of 2-[(2,3-dichlorophenyl)methylene]-3-oxobutanoic acid, ethyl ester (2.87 g., 10 mmole) in anhydrous tetrahydrofuran (10 ml.) is treated with 2-methylpseudourea hydrogen sulfate (2.23 g., 13.0 mmole), sodium acetate (2.21 g., 27.0 mmole), and magnesium sulfate (0.50 g.). The resulting suspension is heated at 50° for 24 hours. Some starting material is still present (TLC). The reaction is allowed to cool down to room temperature, diluted with ethyl acetate, and filtered. The filtrate is washed with water, sodium bicarbonate, and brine. After drying over anhydrous magnesium sulfate, the solvent is evaporated to provide a yellow oil. It is purified by flash chromatography on silica gel (5% ethyl acetate in dichloromethane) to yield 1.31 g. of 1,4-dihydro-2-methoxy-6-methyl-4-(2,3-dichlorophenyl)-5-pyrimidinecarboxylic acid, ethyl ester as a colorless foam.

b) 1,4-Dihydro-4-methyl-6-(2,3-dichlorophenyl)-2-oxo-1,5(2H)-pyrimidinedicarboxylic acid, diethyl ester A solution of 1,4-dihydro-2-methoxy-6-methyl-4-(2,3-dichlorophenyl)-5-pyrimidinecarboxylic acid, ethyl ester (1.3 g., 3.8 mmole) in dichloromethane (10 ml.) is cooled to 0° and treated with pyridine (0.6 ml., 7.58 mmole) followed by ethyl chloroformate (0.4 ml., 4.0 mmole). The cooling bath is removed and the reaction is allowed to stir at room temperature overnight. The solvent is then stripped off to provide a colorless solid. This material is dissolved in tetrahydrofuran-methanol (10 ml. of 1:4 mixture) and treated with 2N hydrochloric acid (2 ml.). The reaction is allowed to stir at room temperature for 30 minutes and the solvent is then evaporated. The residue is extracted with ethyl acetate and the combined extracts are washed with sodium bicarbonate and brine. After drying over anhydrous magnesium sulfate, the solvent is stripped and the residue is crystallized from isopropyl ether to provide 1.25 g. of 3,6-dihydro-4-methyl-6-(2,3-dichlorophenyl)-2-oxo-1,5(2H)pyrimidinedicarboxylic acid, diethyl ester as a colorless solid; m.p. 139.5°-141°. TLC(silica gel; acetone/hexanes, 50:50) $R_f$=0.44.

Anal. calc'd. for $C_{17}H_{18}Cl_2N_2O_5$ C, 50.89; H, 4.52; N, 6.98; Cl, 17.67. Found: C, 51.07; H, 4.57; N, 6.74; Cl, 17.55.

EXAMPLE 4

3,6-Dihydro-4-methyl-2-oxo-6-[2-(trifluoromethyl)-phenyl]-1,5(2H)-pyrimidinedicarboxylic acid, diethyl ester a)

1,4-Dihydro-2-methoxy-6-methyl-4-[2-(trifluoromethyl)phenyl]-5-pyrimidinecarboxylic acid, ethyl ester A solution of 2-[[2-(trifluoromethyl)phenyl]methylene]-3-oxobutanoic acid, ethyl ester (2.86 g., 10.0 mmole) in dry dimethylformamide under argon is treated with 2-methylpseudourea hydrogen sulfate (2.10 g., 12.2 mmole) and sodium acetate (2.0 g., 12.2 mmole). The resulting suspension is allowed to stir at room temperature overnight and is then heated at 55° for 6 hours. Some starting material is still present (TLC). The reaction mixture is diluted with ethyl acetate and filtered. The filtrate is washed with water, sodium bicarbonate, and brine. After drying over anhydrous magnesium sulfate, the solvent is evaporated to give a yellow foam. This material is purified by flash chromatography (5% ethyl acetate in methylene chloride) to give 2.17 g. of 1,4-dihydro-2-methoxy-6-methyl-4-[2-(trifluoromethyl)phenyl]-5-pyrimidinecarboxylic acid, ethyl ester as a colorless thick oil which solidifies on standing. TLC (silica gel; ethyl acetate/hexanes, 40:60) $R_f=0.46$.

b)

3,6-Dihydro-4-methyl-2-oxo-6-[2-(trifluoromethyl)-phenyl]-1,5(2H)-pyrimidinedicarboxylic acid, diethyl ester A solution of 1,4-dihydro-2-methoxy-6-methyl-4-[2-(trifluoromethyl)phenyl]-5-pyrimidinecarboxylic acid, ethyl ester (2.11 g., 6.17 mmole) in methylene chloride (10 ml.) and pyridine (1.2 ml., 15.0 mmole) under argon is cooled to 0° and then treated with 97% ethyl chloroformate (0.7 ml. 7.0 mmole). After the addition is completed, the cooling bath is removed and the reaction is allowed to stir at room temperature for 4 hours. The solvent is then stripped to give a colorless solid. The material is dissolved in methanoltetrahydrofuran (15 ml. of a 3:1 solution) and treated with 2N hydrochloric acid (3 ml.). The reaction is allowed to stir at room temperature for 2 hours and the solvent is evaporated. The residue is extracted with ethyl acetate and the resulting solution is washed with water, sodium bicarbonate, and brine. It is dried over anhydrous magnesium sulfate and evaporated. The resulting residue is triturated with isopropyl ether to give 1.97 g. of crude product as a colorless solid. Recrystallization from isopropyl ether-dichloromethane gives 1.82 g. of 3,6-dihydro-4-methyl-2-oxo-6-[2-(trifluorometyl)phenyl]-1,5(2H)-pyrimidinedicarboxylic acid, diethyl ester as a colorless crystalline product; m.p. 161°-163°. TLC (silica gel; acetone/hexanes, 40:60) $R_f=0.33$.

Anal. calc'd. for: $C_{18}H_{19}F_3N_2O_5$ C, 54.00; H, 4.78; N, 7.00. Found: C, 53.87; H, 4.89; N, 6.89.

EXAMPLE 5

3,6-Dihydro-4-methyl-6-(2-nitrophenyl)-2-oxo-1,5(2H)-pyrimidinedicarboxylic acid, diethyl ester a)

1,4-Dihydro-2-methoxy-6-methyl-4-(2-nitrophenyl)-5-pyrimidinecarboxylic acid, ethyl ester A suspension containing 2-[(2-nitrophenyl)methylene]-3-oxobutanoic acid, ethyl ester (2.63 g., 10.0 mmole), 2-methylpseudourea hydrogen sulfate (2.12 g., 12.2 mmole) and sodium acetate (2.0 g., 12.2 mmole) in dry dimethylformamide (10 ml.) is stirred under argon at room temperature overnight.

The reaction mixture is then heated at 55°-60° for 6 hours. Afterward, it is cooled to ambient temperature, diluted with ethyl acetate, and filtered. The filtrate is thoroughly washed with water, sodium bicarbonate, and brine. After drying over anhydrous magnesium sulfate, the solvent is evaporated to yield a yellow foam. Purification by flash chromatography (5% ethyl acetate in dichloromethane) gives 2.47 g. of 1,4-dihydro-2-methoxy-6-methyl-4-(2-nitrophenyl)-5-pyrimidinecarboxylic acid, ethyl ester. TLC (silica gel; ethyl acetate/hexenes, 40:60) $R_f=0.38$.

b)

3,6-Dihydro-4-methyl-6-(2-nitrophenyl)-2-oxo-1,5(2H)-pyrimidinedicarboxylic acid, diethyl ester A solution of 1,4-dihydro-2-methoxy-6-methyl-4-(2-nitrophenyl)-5-pyrimidinecarboxylic acid, ethyl ester (2.4 g., 7.52 mmole) in dichloromethane (12 ml.) and pyridine (1.2 ml., 15 mmole) is treated at 0° with ethyl chloroformate (0.9 ml., 9.0 mmole of 97%). After the addition is completed, the cooling bath is removed and the stirring is continued at room temperature for 4 hours. The solvent is evaporated and the resulting solid is dissolved in methanoltetrahydrofuran (15 ml. of 2:1 mixture) and treated with 2N hydrochloric acid (3 ml.). After two hours, most of the solvent is removed under vacuum. The resulting solid is taken up in ethyl acetate and washed with water, sodium bicarbonate, and brine. After drying over anhydrous magnesium sulfate, the solvent is removed and the residue is crystallized from methylene chloride-isopropyl ether to give 2.3 g. of product as a light yellow solid. Recrystallization from isopropyl etherdichloromethane gives 2.15 g. of analytically pure 3,6-dihydro-4-methyl-6-(2-nitrophenyl)-2-oxo-1,5(2H)-pyrimidinedicarboxylic acid, diethyl ester; m.p. 150.5°-152°. TLC (silica gel; acetate/hexanes, 40:60) $R_f=0.28$.

Anal calc'd. for $C_{17}H_{19}N_3O_7$ C, 54.11; H, 5.08; N, 11.14. Found: C, 54.00; H, 5.09; N, 11.08.

EXAMPLE 6

3,6-Dihydro-4-methyl-6-(3-nitrophenyl)-2-oxo-1,5(2H)-pyrimidinedicarboxylic acid, 1-ethyl 5(1,1-dimethylethyl) ester a)

1,4-Dihydro-2-methoxy-6-methyl-4-(3-nitrophenyl)-5-pyrimidinecarboxylic acid, 1,1-dimethylethyl ester A mixture of 2-[(3-nitrophenyl)methylene]-3-oxobutanoic acid, 1,1-dimethylethyl ester (6.8 g., 23.3 mmole), 2-methylpseudourea hydrogen sulfate (5.22 g., 30.3 mmole) and sodium bicarbonate (5.87 g., 69.9 mmole) in dimethylformamide (35 ml.) is stirred at room temperature overnight under argon. After 23 hours at room temperature, the reaction is heated at 60° (oil bath) for 5.5 hours. It is then partitioned between ethyl acetate and 5% sodium bicarbonate. The organic phase is washed several times with water, washed with saturated sodium chloride, and dried over potassium carbonate. Evaporation gives 9.9 g. of crude 1,4-dihydro-2-methoxy-6-methyl-4-(3-nitrophenyl)-5-pyrimidinecarboxylic acid, 1,1-dimethylethyl ester as a light brown oil. TLC (silica gel; 50% ethyl acetate/hexanes) major spot at $R_f=0.53$.

b) 3,6-Dihydro-4-methyl-6-(3-nitrophenyl)-2-oxo-1,5(2H)-pyrimidinedicarboxylic acid, 1-ethyl 5-(1,1-dimethylethyl)ester A solution of the ester product from part (a) (3.0 g., 8.62 mmole) and dry pyridine (3.5 ml., 43 mmole) in dry dichloromethane (17 ml.) in an ice bath under argon is treated dropwise via gastight syringe with ethyl chloroformate (0.99 ml., 10.35 mmole). After stirring at 0° for an hour, the reaction mixture is evaporated. The residue is taken up in methanol and treated with 5N hydrochloric acid (pH 1). After two hours stirring at room temperature, the reaction mixture is evaporated. The residue is taken up in dichloromethane and washed with water, sodium bicarbonate and brine. After drying over anhydrous magnesium sulfate, the solvent is evaporated. The residue is dissolved in dichloromethane, diluted with isopropyl ether, and partially evaporated to precipitate 2.76 g. of white crystals. A second crop (0.21 g.) precipitates from the mother liquor. These two crops are dissolved in dichloromethane, diluted with isopropyl ether, and the dichloromethane is boiled off. After cooling to room temperature, the solids that precipitated are filtered and vacuum dried at 70° (oil bath) to give 2.51 g. of 3,6-dihydro-4-methyl-6-(3-nitrophenyl)-2-oxo-1,5(2H)-pyrimidinedicarboxylic acid, 1-ethyl 5-(1,1-dimethylethyl) ester; m.p. 177°–179°. TLC(silica gel; 50% ethyl acetate/hexanes) $R_f=0.48$.

Anal. calc'd. for $C_{19}H_{23}N_3O_7$: C, 56.29; H, 5.72; N, 10.36. Found: C, 56.29; H, 5.83; N, 10.32.

EXAMPLE 7

3,6-Dihydro-4-methyl-6-(3-nitrophenyl)-2-oxo-1,5(2H)-pyrimidinedicarboxylic acid, 5-ethyl 1-(1-methylethyl) ester A solution of 1,4-dihydro-2-methoxy-6-methyl-4-(3-nitrophenyl)-5-pyrimidinecarboxylic acid, ethyl ester (1.5 g., 4.7 mmole) and pyridine (1.90 ml.) in dry dichloromethane (10 ml.) is cooled to 0° under argon and treated dropwise with isopropyl chloroformate (0.70 ml., 6.10 mmole). After the addition is completed, the cooling bath is removed and the reaction is allowed to stir at room temperature for 2 hours. The solvent is removed in vacuo and the resulting residue is dissolved in methanol-tetrahydrofuran (20 ml. of 1:1 mixture). It is then treated with 2N hydrochloric acid (60 ml.) and the reaction is allowed to stir at room temperature for one hour. The solvent is stripped and the residue is taken up in ethyl acetate. The resulting solution is washed with water, sodium bicarbonate, and brine. After drying over anhydrous magnesium sulfate, the solvent is evaporated. The residue is crystallized from dichloromethane-isopropyl ether-hexanes to provide 1.34 g. of colorless solid. The mother liquor is concentrated and the residue is triturated with isopropyl ether-hexanes to provide 282 mg. of a second crop. Both crops are combined and recrystallized from dichloromethaneisopropyl ether-hexanes to give 1.33 g. of 3,6-dihydro-4-methyl-6-(3-nitrophenyl)-2-oxo-1,5(2H)-pyrimidinedicarboxylic acid, 5-ethyl 1-(methylethyl) ester; m.p. 128°–129° (sinters at 121°). TLC (silica gel; 50% ethyl acetate/hexanes) $R_f=0.35$.

Anal calc'd. for $C_{18}H_{21}N_3O_7$: C, 55.24; H, 5.41; N, 10.74. Found: C, 55.23; H, 5.40; N, 10.67.

EXAMPLE 8

3,6-Dihydro-4-methyl-6-(3-nitrophenyl)-2-oxo-1,5(2H)-pyrimidinedicarboxylic acid, 5-ethyl 1-(phenylmethyl) ester A solution of 1,4-dihydro-2-methoxy-6-methyl-4-(3-nitrophenyl)-5-pyrimidinecarboxylic acid, ethyl ester (2.00 g., 6.26 mmole) and pyridine (2.53 ml., 31.3 mmole) in dichloromethane (11 ml.) at $-20°$ (methanol-/ice bath) under argon is treated via syringe with benzyl chloroformate (1.16 ml., 8.14 mmole). After one hour at $-20°$, the reaction is stirred at room temperature for 1.5 hours and evaporated. The residue is taken up in tetrahydrofuran/methanol (20 ml. each), treated with 5N hydrochloric acid (5.0 ml.), and stirred at room temperature for 3 hours. The reaction is quenched with saturated sodium bicarbonate and extracted with ethyl acetate. The organic phase is washed with saturated sodium chloride, dried over anhydrous magnesium sulfate, and evaporated. The residue is chromatographed and crystallized from dichloromethane/isopropyl ether to give 1.75 g. of white crystalline 3,6-dihydro-4-methyl-6-(3-nitrophenyl)-2-oxo-1,5(2H)-pyrimidinedicarboxylic acid, 5-ethyl 1-(phenylmethyl) ester; m.p. 143°–144°. TLC (silica gel; ethyl acetate/hexanes, 2:1) $R_f=0.69$.

Anal. calc'd. for $C_{22}H_{21}N_3O_7$: C, 60.13; H, 4.82; N, 9.56. Found: C, 60.22; H, 4.88; N, 9.73.

EXAMPLE 9

3,6-Dihydro-4-methyl-6-(3-nitrophenyl)-2-oxo-1,5(2H)-pyrimidinedicarboxylic acid, 1-(1,1-dimethylethyl) 5-ethyl ester A solution of 1,4-dihydro-2-methoxy-6-methyl-4-(3-nitrophenyl)-5-pyrimidinecarboxylic acid, ethyl ester (0.96 g., 3.0 mmole) and 4-dimethylaminopyridine (36 mg., 0.3 mmole) in dry acetonitrile (6.0 ml.) at room temperature under argon is treated with di-t-butyl-dicarbonate (0.76 ml., 3.3 mmole). After stirring for one hour, the reaction mixture is evaporated. The residue is taken up in tetrahydrofuran/methanol (10 ml. each) and treated with 1N hydrochloric acid (4.0 ml., pH 1.0). After stirring for 2 hours, the reaction is quenched with saturated sodium bicarbonate, partially evaporated, and extracted with ethyl acetate. The organic phase is washed with saturated sodium chloride and evaporated. Flash chromatography and crystallization from dichloromethane/isopropyl ether gives 792 mg. of 3,6-dihydro-4-methyl-6-(3-nitrophenyl)-2-oxo-1,5(2H)-pyrimidinedicarboxylic acid, 1-(1,1-dimethylethyl) 5-ethyl ester as white electrostatic crystals; m.p. 139°–140°. TLC (silica gel; ethyl acetate/hexanes, 1:1) $R_f=0.46$.

Anal. calc'd. for $C_{19}H_{23}N_3O_7$: C, 56.29; H, 5.72; N, 10.36. Found: C, 56.36; H, 5.62; N, 10.03.

EXAMPLE 10

3,6-Dihydro-4-methyl-6-(3-nitrophenyl)-2-oxo-1,5(2H)-pyrimidinedicarboxylic acid, bis(1,1-dimethylethyl) ester A solution of 1,4-dihydro-2-methoxy-6-methyl-4-(3-nitrophenyl)-5-pyrimidinecarboxylic acid, 1,1-dimethylethyl ester (0.64 g., 1.84 mmole) and 4-dimethylaminopyridine (22 mg., 0.18 mmole) in acetonitrile (4.0 ml.) at room temperature under argon is treated via syringe with di-t-butyl-dicarbonate (0.465 ml., 2.02 mmole). After stirring for one hour, the reaction is diluted with methanol (3 ml.) and treated with 1N hydrochloric acid (2.0 ml.). After stirring for 2 hours, the reaction is quenched with saturated sodium bicarbonate and partially evaporated. The resulting mixture is extracted with ethyl acetate. The organic phase is washed with saturated sodium chloride and evaporated. The residue is flash chromatographed and crystallized from isopropyl ether/hexanes to give 706 mg. of 3,6-dihydro-4-methyl-6-(3-nitrophenyl)-2-oxo-1,5(2H)-pyrimidinedicarboxylic acid, bis(1,1-dimethylethyl) ester as white crystals; m.p. 160°-161°. TLC (silica gel; ethyl acetate/hexanes, 2:3) $R_f=0.43$.

Anal. calc'd. for $C_{21}H_{27}N_3O_7$: C, 58.19; H, 6.28; N, 9.69. Found: C, 58.40; H, 6.26; N, 9.51.

EXAMPLE 11

3,6-Dihydro-4-methyl-6-(3-nitrophenyl)-2-oxo-1,5(2H)-pyrimidinedicarboxylic acid, 1-ethyl 5-(1-methylethyl) ester a)
1,4-Dihydro-2-methoxy-6-methyl-4-(3-nitrophenyl)-5-pyrimidinecarboxylic acid, 1-methylethyl ester A mixture of 2-[(3-nitrophenyl)methylene]-3-oxobutanoic acid, 1-methylethyl ester (10.0 g. 36.0 mmole), sodium bicarbonate (8.40 g., 108 mmole) and 2-methylpseudourea hydrogen sulfate (8.06 g., 46.8 mmole) in dimethylformamide (54 ml.) is heated at 60° (oil bath) under argon for about 60 hours., The resultant mixture is diluted with water and extracted with ethyl acetate. The organic phase is washed with water (six times) and saturated sodium chloride, dried over potassium carbonate, and evaporated. The residue is passed through a pad of silica gel and crystallized from isopropyl ether/hexanes to give 8.04 g. of 1,4-dihydro-2-methoxy-6-methyl-4-(3-nitrophenyl)-5-pyrimidinecarboxylic acid, 1-methylethyl ester as yellow crystals. TLC (silica gel; ethyl acetate: hexanes, 1:1) $R_f=0.45$.

b)
3,6-Dihydro-4-methyl-6-(3-nitrophenyl)-2-oxo-1,5(2H)-pyrimidinedicarboxylic acid, 1-ethyl 5-(1-methylethyl) ester A solution of the ester product from part(a) (1.66 g., 5.0 mmole) and pyridine (2.02 ml., 25 mmole) in dichloromethane (10 ml.) in an ice bath under argon is treated via gas-tight syringe with ethyl chloroformate (0.57 ml., 6.0 mmole). After stirring at 0° for one hour, the reaction mixture is evaporated. The residue is taken up in tetrahydrofuran/methanol (10 ml. each) and treated with 5N hydrochloric acid (3.0 ml., pH 1). After stirring at room temperature for one hour, the reaction is cooled in an ice bath and quenched with saturated sodium bicarbonate. After partial evaporation, the remaining aqueous phase is diluted with water and extracted with ethyl acetate. The organic phase is washed with saturated sodium chloride, dried over anhydrous magnesium sulfate, and evaporated. The residue is flash chromatographed and crystallized from dichloromethane/isopropyl ether to give 1.403 g. of 3,6-dihydro-4-methyl-6-(3-nitrophenyl)-2-oxo-1,5(2H)-pyrimidinedicarboxylic acid, 1-ethyl 5-(1-methylethyl) ester as white crystals; m.p. 156°-157°. TLC (silica gel; ethyl acetate:hexanes, 1:1) $R_f=0.40$.

Anal. calc'd. for $C_{18}H_{21}N_3O_7$: C, 55.24; H, 5.41; N, 10.74. Found: C, 55.23; H, 5.38; N, 10.68.

EXAMPLE 12

3,6-Dihydro-4-methyl-6-(3-nitrophenyl)-2-oxo-1,5(2H)-pyrimidinedicarboxylic acid, bis (1methylethyl) ester A solution of 1,4-dihydro-2-methoxy-6-methyl-4-(3-nitrophenyl)-5-pyrimidinecarboxylic acid, 1-methylethyl ester (1.66 g., 5.0 mmole) and pyridine (2.0 g., 25 mmole) in distilled dichloromethane (10 ml.) in an ice bath under argon is treated via gas tight syringe with isopropyl chloroformate (0.68 ml., 6.0 mmole). After the addition is completed, the ice bath is removed and the reaction mixture is stirred at room temperature for 2 hours. The reaction mixture is then evaporated and the residue is taken up in tetrahydrofuran/methanol (10 ml. each), treated with 1N hydrochloric acid, and stirred at room temperature for 1.5 hours. The reaction is then quenched with saturated sodium bicarbonate and evaporated. The residue is diluted with water and extracted with ethyl acetate. The organic phase is washed with saturated sodium chloride, dried over anhydrous magnesium sulfate, and evaporated. The residue is chromatographed and crystallized from isopropyl ether/dichloromethane to give 1.307 g. of 3,6-dihydro-4-methyl-6-(3-nitro-phenyl)-2-oxo-1,5(2H)-pyrimidinedicarboxylic acid, bis(1-methylethyl) ester as translucent colorless crystals; m.p. 143°-144°. TLC (silica gel; ethyl acetate:hexanes, 1:1) $R_f=0.48$.

Anal. calc'd. for $C_{19}H_{23}N_3O_7$: C, 56.29; H, 5.72; N, 10.36. Found: C, 56.46; H, 5.65; N, 10.29.

EXAMPLE 13

3,6-Dihydro-4-methyl-6-(3-nitrophenyl)-2-oxo-1,5(2H)-pyrimidinedicarboxylic acid, 5-(1-methylethyl) 1-(phenylmethyl) ester Following the procedure of Example 12 but employing benzyl chloroformate (0.93 ml., 0.65 mmole), one obtains 1.486 g. of white crystalline 3,6-dihydro-4-methyl-6-(3-nitrophenyl)-2-oxo-1,5(2H)-pyrimidinedicarboxylic acid, 5-(1-methylethyl) 1-(phenylmethyl) ester; m.p. 158°-159°. TLC (silica gel; ethyl acetate:hexanes, 1:1) $R_f=0.50$.

Anal calc'd. for $C_{23}H_{23}N_3O_7$: C, 60.92; H, 5.11; N, 9.27. Found: C, 61.00; H, 5.17; N, 9.27.

EXAMPLE 14

6-(2,3-Dichlorophenyl)-3,6-dihydro-4-methyl-2-oxo-1,5(2H)-pyrimidinedicarboxylic acid, 1-ethyl 5-methyl ester a)
1,4-Dihydro-2-methoxy-6-methyl-4-(2,3-dichlorophenyl)-5-pyrimidinecarboxylic acid, methyl ester A mixture of 2-[(2,3-dichlorophenyl)methylene]-3-oxobutanoic acid, methyl ester (5.0 g., 18.3 mmole), 2-methylpseudourea hydrogen sulfate (4.10 g., 23.8 mmole) and sodium bicarbonate (4.61 g., 54.9 mmole) in dimethylformamide (27 ml.) is stirred overnight under argon at room temperature. The mixture is then heated at 60° (oil bath) for 5 hours. The resulting mixture is partitioned between ethyl acetate and water. The organic phase is washed with water (ten times) and saturated sodium chloride, dried over potassium carbonate, and evaporated to give 7.28 g. of 1,4-dihydro-2-methoxy-6-methyl-4-(2,3-dichlorophenyl)-5-pyrimidinecarboxylic acid, methyl ester as a light brown oil. TLC (silica gel; ethyl acetate: hexanes, 1:1) ma3or spot at $R_f=0.56$.

b)
6-(2,3-Dichlorophenyl)-3,6-dihydro-4-methyl-2-oxo-1,5(2H)-pyrimidinedicarboxylic acid, 1-ethyl 5-methyl ester A solution of the methyl ester product from part (a) (1.80 g., 4.53 mmole) and pyridine (2.21 ml., 27.35 mmole) in dichloromethane (11 ml.) in an ice bath under argon is treated via gas tight syringe with ethyl chloroformate. After stirring at 0° for 15 minutes, the ice bath is removed and the reaction is stirred at room temperature for 1.5 hours. The mixture is then evaporated and the residue is taken up in tetrahydrofuran/methanol (10 ml. each). The resulting solution is treated with 5N hydrochloric acid (60 ml., pH 2) and stirred at room temperature 1.5 hours. The reaction is then evaporated and partitioned between saturated sodium bicarbonate and ethyl acetate. The organic phase is washed with saturated sodium chloride, dried over anhydrous magnesium sulfate, and crystallized from dichloromethane/isopropyl ether to give 1.291 g. of 6-(2,3-dichlorophenyl)-3,6-dihydro-4-methyl-2- oxo-1,5(2H)-pyrimidinedicarboxylic acid, 1-ethyl 5-methyl ester as shiny white crystals; m.p. 159°-160°. TLC (silica gel; ethyl acetate: hexanes, 2:1) $R_f=0.48$.

Anal. calc'd. for $C_{16}H_{16}N_2O_5Cl_2$: C, 49.63; H, 4.16; N, 7.24; Cl, 18.31. Found: C, 49.71; H, 4.15; N, 7.15; Cl, 18.31.

EXAMPLE 15

6-(2,3-Dichlorophenyl)-3,6-dihydro-4-methyl-2-oxo-1,5(2H)-pyrimidinedicarboxylic acid, 5-ethyl 1-methyl ester A solution of 1,4-dihydro-2-methoxy-6-methyl-4-(2,3-dichlorophenyl)-5-pyrimidinecarboxylic acid, ethyl ester (1.47 g., 4.28 mmole) and distilled pyridine (1.7 ml., 21 mmole) in dry dichloromethane (16 ml.) in an ice bath under argon is treated via gas tight syringe with methyl chloroformate (0.40 ml., 5.14 mmole). After stirring for one hour at 0°, the reaction mixture is evaporated. The residue is taken up in tetrahydrofuran/methanol (10 ml. each) and treated wtih 5N hydrochloric acid (3.0 ml.). After stirring at room temperature for one hour, the reaction is cooled in an ice bath and quenched with sodium bicarbonate. After partial evaporation, the aqueous phase is diluted with water and extracted with chloroform. The organic phase is washed with saturated sodium chloride, dried over anhydrous magnesium sulfate, and evaporated. The residue is flash chromatographed and crystallized from isopropyl ether/dichloromethane to give 668 mg. of white crystalline 6-(2,3-dichlorophenyl)-3,6-dihydro-4-methyl-2-oxo-1,5(2H)-pyrimidinedicarboxylic acid, 5-ethyl 1-methyl ester; m.p. 197°-205°. TLC (silica gel; ethyl acetate: hexanes, 1:1) $R_f=0.20$.

Anal. calc'd. for $C_{16}H_{16}N_2O_5Cl_2$: C, 49.63; H, 4.16; N, 7.23; Cl, 18.31. Found: C, 49.35; H, 4.16; N, 7.27; Cl, 18.51.

EXAMPLE 16

6-(2,3-Dichlorophenyl)-3,6-dihydro-4-methyl-2-oxo-1,5(2H)-pyrimidinedicarboxylic acid, 5-ethyl 1-(1-methylethyl) ester Following the procedure of Example 15 but employing isopropyl chloroformate (0.58 ml., 5.10 mmole) one obtains 1.219 g., (69%) of white crystalline 6-(2,3-dichlorophenyl)-3,6-dihydro-4-methyl-2-oxo-1,5(2H)-pyrimidinedicarboxylic acid, 5-ethyl 1-(1-methylethyl) ester; m.p. 139°-140°. TLC (silica gel; ethyl acetate:hexanes, 1:1) $R_f=0.34$.

Anal. calc'd. for $C_{18}H_{20}N_2O_5Cl_2$: C, 52.06; H, 4.85; N, 6.74; Cl, 17.07. Found: C, 51.91; H, 4.66; N, 6.73; Cl, 16.80.

EXAMPLE 17

6-(2,3-Dichlorophenyl)-3,6-dihydro-4-methyl-2-oxo-1,5(2H)-pyrimidinedicarboxylic acid, 1-methyl 5-(1-methylethyl) ester a)
1,4-Dihydro-2-methoxy-6-methyl-4-(2,3-dichlorophenyl)-5-pyrimidinecarboxylic acid, 1-methylethyl ester A solution of 2-[(2,3-dichlorophenyl)methylene]-3-oxobutanoic acid, 1-methylethyl ester (6.0 g., 20.0 mmole) in dry dimethylformamide (20 ml.) is treated with 2-methylpseudourea hydrogen sulfate (4.3 g., 25.0 mmole) and sodium bicarbonate (6.3 g., 75.0 mmole). The reaction mixture is heated at 65° for 48 hours. It is then allowed to cool to room temperature and is diluted with ethyl acetate. The solid is filtered off and the filtrate is washed with water and brine, dried over anhydrous magnesium sulfate, and evaporated. The residue is triturated with isopropyl ether to give 3.79 g. of light yellow solid 1,4-dihydro-2-methoxy-6-methyl-4-(2,3-dichlorophenyl)-5-pyrimidinecarboxylic acid, 1-methylethyl ester; m.p. 139°-141°. Concentration of the mother liquor and trituration with isopropyl ether provides a second crop (0.87 g.).

b)
6-(2,3-Dichlorophenyl)-3,6-dihydro-4-methyl-2-oxo-1,5(2H)-pyrimidinedicarboxylic acid, 1-methyl 5-(1-methylethyl) ester A solution of the 1-methylethyl ester product from part(a) (10 g., 2.8 mmole) in dry dichloromethane (10 ml.) and pyridine (0.70 ml., 8.40 mmole) under argon is cooled to 0° and treated dropwise with methyl chloroformate (0.28 ml., 3.6 mmole). After the addition is completed, the reaction is allowed to warm to room temperature and stirred for 2 hours. The solvent is evaporated and the residue is dissolved in methanol (12 ml.). It is then treated with 1N hydrochloric acid (4.0 ml.) and stirred for one hour. Most of the methanol is evaporated and the residue is partitioned between ethyl acetate and water. The organic extract is washed with brine and dried over anhydrous magnesium sulfate. Evaporation of the solvent gives a colorless residue which is recrystallized from dichloromethane/isopropyl ether to give 745 mg. of 6-(2,3-dichlorophenyl)-3,6-dihydro-4-methyl-2-oxo-1,5(2H)-pyrimidinedicarboxylic acid, 1-methyl 5-(1-methylethyl) ester; m.p.

208°-210°. TLC (silica gel; acetone:hexanes, 40:60) $R_f=0.40$.

Anal. calc'd. for $C_{17}H_{18}Cl_2N_2O_5$: C, 51.01; H, 4.28; N, 7.00; Cl, 17.72. Found: C, 51.11; H, 4.48; N, 6.98; Cl, 17.73.

EXAMPLE 18

6-(2,3-Dichlorophenyl)-3,6-dihydro-4-methyl-2-oxo-1,5(2H)-pyrimidinedicarboxylic acid, dimethyl ester A solution of 1,4-dihydro-2-methoxy-6-methyl-4-(2,3-dichlorophenyl)-5-pyrimidinecarboxylic acid, methyl ester (1.56 g., 4.73 mmole) and pyridine (2.2 ml., 27 mmole) in dichloromethane (10 ml.) in an ice bath under argon is treated via gas tight syringe with methyl chloroformate (0.44 ml., 5.68 mmole). After stirring at 0° for one hour, the reaction mixture is evaporated. The residue is taken up in tetrahydrofuran/methanol (25 ml. each) and treated with 5N hydrochloric acid (40 ml., pH 1). After stirring at room temperature for one hour, the reaction is cooled in an ice bath and quenched with sodium bicarbonate. After partial evaporation, the remaining aqueous phase is diluted with water and extracted with ethyl acetate. The organic phase is washed with saturated sodium chloride, dried over anhydrous magnesium sulfate, and evaporated. The residue is flash chromatographed and crystallized from ethyl acetate/hexanes to give 1.105 g. of 6-(2,3-dichloro-phenyl)-3,6-dihydro-4-methyl-2-oxo-1,5(2H)pyrimidinedicarboxylic acid, dimethyl ester as light, fluffy white crystals; m.p. 235°-236°. TLC (silica gel; ethyl acetate:hexanes, 2:1) $R_f=0.37$.

Anal. calc'd. for $C_{15}H_{14}Cl_2N_2O_5$: C, 48.28; H, 3.78; N, 7.51; Cl, 19.00. Found: C, 48.28; H, 3.79; N, 7.47; Cl, 18.95.

EXAMPLE 19

6-(2,3-Dichlorophenyl)-3,6-dihydro-4-methyl-2-oxo-1,5(2H)-pyrimidinedicarboxylic acid, 5-methyl 1-(1-methylethyl) ester Following the procedure of Example 18 but employing isopropyl chloroformate (0.62 ml., 5.44 mmole), one obtains 1.065 g., (59%) of 6-(2,3-dichlorophenyl)-3,6-dihydro-4-methyl-2-oxo-1,5(2H)-pyrimidinedicarboxylic acid, 5-methyl 1-(1-methylethyl) ester as white crystals; m.p. 162°-163°. TLC (silica gel; ethyl acetate: hexanes, 2:1) $R_f=0.56$.

Anal. calc'd. for $C_{17}H_{18}Cl_2N_2O_5$: C, 50.89; H, 4.52; N, 6.98; Cl, 17.67. Found: C, 51.08; H, 4.49; N, 7.01; Cl. 17.56.

EXAMPLE 20

6-(2,3-Dichlorophenyl)-3,6-dihydro-4-methyl-2-oxo-1,5(2H)-pyrimidinedicarboxylic acid, 1-ethyl 5-(1-methylethyl)ester A solution of 1,4-dihydro-2-methoxy-6-methyl-4-(2,3-dichlorophenyl)-5-pyrimidinecarboxylic acid, 1-methylethyl ester (1.2 g., 3.37 mmole) and pyridine (1.0 ml.) in dichloromethane (10 ml.) under argon is cooled to 0° and treated dropwise with ethyl chloroformate (0.4 ml., 4.04 mmole). After the addition is completed, the cooling bath is removed and the reaction is allowed to stir at room temperature for one hour. The solvent is then stripped off to provide a colorless solid. This crude material is dissolved in methanol (12 ml.) and treated with 2N hydrochloric acid (3 ml.). The reaction is allowed to stir at room temperature overnight precipitating a colorless solid. The solvent is evaporated and the residue is dissolved in ethyl acetate. The resulting solution is washed with water, sodium bicarbonate solution, and brine. After drying over anhydrous magnesium sulfate, the solvent is stripped off and the residue is triturated with isopopyl ether to give 1.12 g. of colorless solid. Recrystallization from dichloromethane—isopropyl ether gives 6-(2,3-dichlorophenyl)-3,6-dihydro-4-methyl-2-oxo-1,5(2H)-pyrimidinedicarboxylic acid, 1-ethyl 5-(1-methylethyl) ester as a colorless solid; m.p. 173°-175°. TLC (silica gel; ethyl acetate: hexanes, 60:40) $R_f=0.30$.

Anal. calc'd. for $C_{18}H_{20}Cl_2N_2O_5$: C, 52.06; H, 4.85; N, 6,74; Cl, 17.07. Found: C, 52.07; H, 4.61; N, 6.49, Cl, 17.07.

EXAMPLE 21

6-(2,3-Dichlorophenyl)-3,6-dihydro-4-methyl-2-oxo-1,5(2H)-pyrimidinedicarboxylic acid, bis (1-methylethyl) ester Following the procedure of Example 20 but employing isopropyl chloroformate (0.47 ml., 4.04 mmole), one obtains 1.19 g. (82.6%) of 6-(2,3-dichlorophenyl)-3,6-dihydro-4-methyl-2-oxo-1,5(2H)-pyrimidinedicarboxylic acid, bis (1-methylethyl) ester as a colorless solid; m.p. 158°-160°. TLC (silica gel; ethyl acetate: hexanes, 60:40) $R_f=0.40$.

Anal. calc'd. for $C_{19}H_{22}Cl_2N_2O_5$: C, 53.15; H, 5.17; N, 6.52; Cl, 16.52. Found: C, 53.46; H, 5.21; N, 6.24; Cl, 16.27.

EXAMPLE 22

6-(2,3-Dichlorophenyl)-3,6-dihydro-4-methyl-2-oxo-1,5(2H)-pyrimidinedicarboxylic acid, 5-ethyl 1-(phenylmethyl) ester A solution of 1,4-dihydro-2-methoxy-6-methyl-4-(2,3-dichlorophenyl)-5-pyrimidinecarboxylic acid, ethyl ester (1.25 g., 3.64 mmole) and pyridine (2.0 ml., 25 mmole), in distilled dichloromethane (7.0 ml.) in an ice bath under argon is treated via gas tight syringe with benzyl chloroformate (0.78 ml., 5.46 mmole). The ice bath is removed and the reaction is stirred at room temperature for 2 hours. It is then evaporated, taken up in tetrahydrofuran/methanol (10 ml. each), and treated with 1N hydrochloric acid (8 ml., pH 1). After stirring at room temperature for one hour, the reaction is quenched with saturated sodium bicarbonate and evaporated. The residue is partitioned between ethyl acetate and water. The organic phase is washed with saturated sodium chloride and evaporated. Flash chromatography and crystallization from isopropyl ether/dichloromethane gives 1.007 g. of 6-(2,3-dichlorophenyl)-3,6-dihydro-4-methyl-2-oxo-1,5(2H)-pyrimidinedicarboxylic acid, 5-ethyl 1-(phenylmethyl) ester as white crystals; m.p. 160°-161°. TLC (silica gel; ethyl acetate:-hexanes, 1:1) $R_f=0.44$.

Anal. calc'd. for $C_{22}H_{20}Cl_2N_2O_5$: C, 57.03; H, 4.35; N, 6.05; Cl, 15.30. Found: C, 56.86; H, 4.32; N, 5.98; Cl, 15.41.

EXAMPLE 23

6-(2-Chloro-3-nitrophenyl)-3,6-dihydro-4-methyl-2-oxo-1,5(2H)-pyrimidinedicarboxylic acid, 5-ethyl 1-(1-methylethyl) ester a)

2-[(2-Chloro-3-nitrophenyl)methylene]-3-oxobutanoic acid, ethyl ester

A solution of 2-chloro-3-nitrobenzaldehyde (2.00 g., 10.8 mmole), ethyl acetoacetate (1.37 ml., 10.78 mmole), piperidine (0.25 ml.) and acetic acid (0.5 ml.) in benzene (21 ml.) under argon is fitted with a Dean-Stark trap and heated at 110° (oil bath) for 3 hours. The reaction is diluted with ether and washed with saturated sodium bicarbonate, 1N hydrochloric acid, and saturated sodium chloride, dried over anhydrous magnesium sulfate, and evaporated to give 2-[(2-chloro-3-nitrophenyl)methylene]-3-oxobutanoic acid, ethyl ester as a red oil (3.42 g.). TLC (silica gel; ether/hexanes) $R_f=0.31$ and 0.43.

b) 1
4-Dihydro-2-methoxy-6-methyl-4-(2-chloro-3-nitrophenyl]-5-pyrimidinecarboxylic acid, ethyl ester A mixture of 2-[(2-chloro-3-nitrophenyl)methylene]-3-oxobutanoic acid, ethyl ester (10.8 mmole), 2-methylpseudourea hydrogen sulfate (2.42 g., 14.0 mmole), and sodium bicarbonate (2.72 g., 32.4 mmole) in dimethyformamide (16 ml.) is heated at 60° (oil bath) overnight under argon. The mixture is diluted with water and extracted with ethyl acetate. The organic phase is washed with water (7 times) and saturated sodium chloride, dried over potassium carbonate, and evaporated to give 4.10 g. of 1,4-dihydro-2-methoxy-6-methyl-4-(2-chloro-3-nitrophenyl)-5-pyrimidinecarboxylic acid, ethyl ester as a red oil. TLC (silica gel; ethyl acetate:hexanes, 2:1) major spot at $R_f=0.76$.

c)

6-(2-Chloro-3-nitrophenyl)-3,6-dihydro-4-methyl-2-oxo-1,5(2H)-pyrimidinedicarboxylic acid, 5-ethyl 1-(1-methylethyl) ester A solution of the ethyl ester product from part(b) (1.72 g., 4.8 mmole) and pyridine (2.1 ml., 26.0 mmole) in dichloromethane (16 ml.) in an ice bath under argon is treated dropwise via gas tight syringe with isopropyl chloroformate (0.77 ml., 6.77 mmole). After 15 minutes at 0°, the ice bath is removed and the reaction is stirred at ambient temperature for 2 hours. The mixture is then concentrated. The residue is taken up in tetrahydrofuran/methanol (about 10 ml. each) and the resulting solution is treated with 5N hydrochloric acid (5.0 ml., pH 2) and stirred at room temperature for one hour. The reaction is then evaporated and partitioned between sodium bicarbonate and ethyl acetate. The organic phase is washed with saturated sodium chloride, dried over anhydrous magnesium sulfate, chromatographed, and crystallized from dichloromethane/isopropyl ether to give the product as off-white crystals (greater than 1.1 g.). These solids are recrystallized from ethyl acetate/isopropanol to give 826 mg. of 6-(2-chloro-3-nitrophenyl)-3,6-dihydro-4-methyl-2-oxo-1,5(2H)-pyrimidinedicarboxylic acid, 5-ethyl 1-(1-methylethyl) ester as sharp white needles; m.p. 194°-195°. TLC (silica gel; 20% ethyl acetate/hexanes) $R_f=0.36$.

Anal. calc'd. for $C_{18}H_{20}N_3O_7Cl$: C, 50.77; H, 4.73; N, 9.87; Cl, 8.32. Found: C, 51.13; H, 5.11; N, 9.48; Cl, 8.10.

EXAMPLE 24

6-(2-Chloro-3-nitrophenyl)-3,6-dihydro-4-methyl-2-oxo-1,5(2H)-pyrimidinedicarboxylic acid, diethyl ester Following the procedure of Example 23 but employing ethyl chloroformate (0.68 ml., 7.07 mmole), one obtains 949 mg. (45%) of 6-(2-chloro-3-nitrophenyl)-3,6-dihydro-4-methyl-2-oxo-1,5(2H)-pyrimidinedicarboxylic acid, diethyl ester as white powdery crystals; m.p. 176°-178°. TLC (silica gel; 20% ethyl acetate/hexanes) $R_f=0.36$.

Anal. calc'd. for $C_{17}H_{18}N_3O_7Cl$: C, 49.58; H, 4.41; N, 10.20; Cl, 8.61. Found: C, 49.71; H, 4.38; N, 10.27; Cl, 8.55.

EXAMPLE 25

3,6-Dihydro-4-methyl-6-[2-(methylthio)-3-pyridinyl]-2-oxo-1,5(2H)-pyrimidinedicarboxylic acid, 1-ethyl 5-(1-methylethyl) ester a)

2-[[2-(Methylthio]-3-pyridinyl]methylene]-3-oxobutanoic acid, 1-methylethyl ester A mixture of 2-methylthiopyridine-3-carbaldehyde (0.82 g., 5.3 mmole) [prepared according to the procedure of Christensen et al., Synthesis, 1980, pages 405–407]and isopropyl acetoacetate (0.77 g., 5.3 mmole) in dichloromethane (20 ml.) is treated with acetic acid (4 drops), piperidine (6 drops) and anhydrous magnesium sulfate (1.5 g.). The mixture is stirred at room temperature for 65 hours. The solution is filtered, stripped in vacuo, and the residue is dissolved in ethyl acetate and washed with sodium bicarbonate, water, and saturated brine. The aqueous washes are back extracted with fresh ethyl acetate. The combined organic solutions are dried over anhydrous magnesium sulfate and concentrated in vacuo to give 1.4 g. of amber oil. Flash chromatography and elution with ethyl acetate:hexanes (1:4) gives 1.25 g. of 2-[[2-(methylthio)-3-pyridinyl]methylene]-3-oxobutanoic acid, 1-methylethyl ester as an oil. TLC (silica gel; ethyl acetate:hexanes, 1:1) $R_f=0.56$, 0.61.

Anal. calc'd. for $C_{14}H_{17}NO_3S$: C, 60.19; H, 6.14; N, 5.02; S, 11.48. Found: C, 59.54; H, 6.00; N, 4.95; S, 11.34.

b)

1,4-Dihydro-2-methoxy-6-methyl-4-[2-(methylthio)-3-pyridinyl]-5-pyrimidinecarboxylic acid, 1-methylethyl ester A mixture of 2-[[2-(methylthio)-3-pyridinyl]methylene]-3-oxobutanoic acid, 1-methylethyl ester (1.25 g., 4.5 mmole) and 2-methylpseudourea hydrogen sulfate (1.01 g., 5.87 mmole) in dry dimethylformamide (7 ml.) under argon is treated with sodium bicarbonate (1.13 g., 13.5 mmole) and warmed at 60° overnight. The crude reaction mixture is diluted with ethyl acetate and washed with sodium bicarbonate, water (twice), and saturated brine. The aqueous washes are back extracted with fresh ethyl acetate. The combined organic extracts are dried over anhydrous magnesium sulfate and concentrated in vacuo to give 1.71 g. of crude product. Flash chromatography and elution with ethyl acetate:hexanes (1:2) gives 800 mg. of 1,4-dihydro2-methoxy-6-methyl-4-[2-(methylthio)-3-pyridinyl]-5-pyrimidinecarboxylic acid, 1-methylethyl ester as an oil. TLC (silica gel, ethyl acetate:hexanes, 1:1) $R_f$=0.37.

Anal. calc'd. for $C_{16}H_{21}N_3O_3S$: C, 57.29; H, 6.31; N, 12.53; S, 9.56. Found: C, 54.41; H, 5.96; N, 11.42; S, 8.81.

c)

3,6-Dihydro-4-methyl-6-[2-(methylthio)-3-pyridinyl]-2-oxo-1,5(2H)-pyrimidinedicarboxylic acid, 1-ethyl 5-(1-methylethyl)ester The 1-methylethyl ester product from part (b) (800 mg., 2.36 mmole) in dry dichloromethane (10 ml.) under argon at 0°–5° is treated with pyridine (0.93 ml., 0.93 g., 11.8 mmole) and then with ethyl chloroformate (0.30 ml., 0.33 g., 3.06 mmole) over a 10–15 minute period. After stirring for 2 hours at 0°–5°, the mixture is diluted with ethyl acetate and washed with sodium bicarbonate, water (twice), and saturated brine. The aqueous fractions are back extracted with ethyl acetate. The combined organic fractions are dried over anhydrous magnesium sulfate and concentrated in vacuo to give 860 mg. of an amorphous solid. This material (860 mg., 2.1 mmole) is taken up in methanol/tetrahydrofuran (15 ml. each) and is warmed to achieve solution. The solution is then cooled in an ice bath and treated with 2N hydrochloric acid to a pH of about 2. The mixture is stirred overnight at room temperature and then concentrated in vacuo. The residue is taken up in ethyl acetate and washed with sodium bicarbonate, water, and saturated brine. The aqueous fractions are back extracted with fresh ethyl acetate. The combined organic fractions are dried over anhydrous magnesium sulfate and concentrated in vacuo to give 830 mg. of crude product. Trituration with isopropyl ether/hexane followed by crystallization from dichloromethane/hexane gives 520 mg. of 3,6-dihydro-4-methyl-6-[2-(methylthio)-3-pyridinyl]-2-oxo-1,5(2H)-pyrimidinedicarboxylic acid, 1-ethyl 5-(1-methylethyl) ester; m.p. 142°–145°. TLC (silica gel; ethyl acetate:hexanes, 1:1) $R_f$=0.55.

Anal. calc'd. for $C_{18}H_{23}N_3O_5S$: C, 54.94; H, 5.89; N, 10.68; S, 8.15. Found: C, 54.56; H, 5.87; N, 10.56; S, 8.08.

EXAMPLE 26

3,6-Dihydro-4-methyl-6-(3-nitrophenyl)-2-oxo-1,5(2H)-pyrimidinedicarboxylic acid, 1-ethyl ester A solution of 3,6-dihydro-4-methyl-6-(3-nitrophenyl)-2-oxo-1,5(2H)-pyrimidinedicarboxylic acid, 1-ethyl 5-(1,1-dimethylethyl) ester (1.5 g., 3.70 mmole) [prepared as set forth in Example 6] in dichloromethane (10 ml.) at room temperature under argon is treated with trifluoroacetic acid (3.0 ml.). After stirring for 3 hours, the reaction mixture is evaporated. The residue is triturated with ether to give an off-white solid (1.2 g.). This solid is dissolved in 5% methanol/dichloromethane, diluted with isopropyl ether (45 ml.), and gently boiled to remove the dichloromethane. After cooling to room temperature, the solids which precipitate are vacuum dried at 70° (oil bath) to give 1.057 g. of 3,6-dihydro-4-methyl-6-(3-nitrophenyl)-2-oxo-1,5(2H)-pyrimidinedicarboxylic acid, 1-ethyl ester as white crystals; m.p. sinters at 120°–130°. TLC (silica gel; 2% methanol/ethyl acetate) $R_f$=0.67.

Anal. calc'd. for $C_{15}H_{15}N_3O_7$: C, 51.58; H, 4.33; N, 12.03. Found: C, 51.32; H, 4.47; N, 11.70.

EXAMPLE 27

3,6-Dihydro-4-methyl-6-(3-nitrophenyl)-2-oxo-1,5(2H)-pyrimidinedicarboxylic acid, 5-ethyl 1-[2-[methyl(phenylmethyl)amino]ethyl]ester, monohydrochloride a)

2-Methoxy-4-methyl-6-(3-nitrophenyl)-1,5(6H)-pyrimidinedicarboxylic acid, 5-ethyl 1-[2-[methyl(phenylmethyl)amino]ethyl]ester A solution of 1,4-dihydro-2-methoxy-6-methyl-4-(3-nitrophenyl)-5-pyrimidinecarboxylic acid, ethyl ester (1.60 g., 5.0 mmole) and dry triethylamine (2.70 ml., 20 mmole) in dry dichloromethane (10 ml.) in an ice bath under argon is treated dropwise via gas tight syringe with a 1.3M solution of phosgene in benzene (5.0 ml., 6.5 mmole). After stirring at 0° for 3 hours, more phosgene solution (1.0 ml., 1.3 mmole) is added and the reaction is stirred an additional 30 minutes. While still at 0°, N-benzyl-N-methyl ethanolamine (1.22 ml., 7.5 mmole) is added via gas tight syringe. The reaction is then stirred at room temperature for 9 hours. The reaction is partitioned between ethyl acetate and saturated sodium bicarbonate. The organic phase is washed with saturated sodium chloride, dried over potassium carbonate, and evaporated. The resultant yellow oil is purified via flash chromatography (25% acetone/hexane plus a small amount of triethylamine) to give 3.2 g. of 2-methoxy-4-methyl-6-(3-nitrophenyl)-1,5(6H)-pyrimidinedicarboxylic acid, 5-ethyl 1-[2-methyl(-phenylmethyl)amino]ethyl]ester. TLC (30% acetone/hexane) major spot at $R_f$=0.31.

b)

3,6-Dihydro-4-methyl-6-(3-nitrophenyl)-2-oxo-1,5(2H)-pyrimidinedicarboxylic acid, 5-ethyl 1-[2-[methyl(phenylmethyl)amino]ethyl]ester, monohydrochloride The crude ester product from part (a) (3.2 g., 5.0 mmole) is taken up in tetrahydrofuran/methanol (20 ml. each), treated with 5N hydrochloric acid (3.0 ml., pH 1), and stirred overnight at room temperature. The mixture is then partitioned between ethyl acetate and saturated sodium bicarbonate. The organic phase is washed with saturated sodium chloride, dried over anhydrous magnesium sulfate, and evaporated. The free base is regenerated, flash chromatographed (25% acetone/hexanes), taken up in ethanol, and treated with methanolic hydrochloric acid. The precipitated solids are filtered and dried to give 847 mg. of 3,6-dihydro-4-methyl-6-(3-nitrophenyl)2-oxo-1,5(2H)-pyrimidinedicarboxylic acid, 5-ethyl 1-[2-[methyl(-phenylmethyl)aminoethyl]ester, monohydrochloride as white crystals; m.p. 189°–191°. A second crop of 285 mg. is obtained from the mother liquor. TLC (silica gel; 40% acetone/hexanes) $R_f$=0.28. (silica gel; dichloromethane:methanol:acetic acid, 15:1:1) $R_f$=0.18.

Anal. calc'd. for $C_{25}H_{28}N_4O_7$·HCl: C, 56.33; H, 5.48; N, 10.51; Cl, 6.65. Found: C, 56.13; H, 5.66; N, 10.24; Cl, 6.70.

EXAMPLE 28

3,6-Dihydro-4-methyl-6-(3-nitrophenyl)-2-oxo-1,5(2H)-pyrimidinedicarboxylic acid, 5-(1-methylethyl) 1-[2-[methyl(phenylmethyl)amino]ethyl]ester, monohydrochloride a)

2-Methoxy-4-methyl-6-(3-nitrophenyl)-1,5(6H)-pyrimidinedicarboxylic acid, 5-(1-methylethyl) 1-[2-methyl(phenylmethyl)amino]ethyl]ester A solution of 1,4-dihydro-2-methoxy-6-methyl-4-(3-nitrophenyl)-5-pyrimidinecarboxylic acid, 1-methylethyl ester (2.00 g., 6.0 mmole) and triethylamine (3.34 ml., 24.0 mmole) in dichloromethane (24 ml.) in an ice bath under argon is treated via gas tight syringe with a 1.3M solution of phosgene in benzene (6.0 ml., 7.8 mmole). After stirring at 0° for 2 hours, the reaction is treated with N-benzyl-N-methyl ethanolamine (1.46 ml., 9.0 mmole) and stirred at room temperature overnight. The reaction is then diluted with water and extracted with dichloromethane. The organic phase is washed with saturated sodium chloride and evaporated. Flash chromatography of the residue gives 4.09 g. of 2-methoxy-4-methyl-6-(3-nitrophenyl)-1,5(6H)-pyrimidinedicarboxylic acid, 5-(1-methylethyl) 1-[2-[methyl(phenylmethyl)amino]ethyl]ester as a yellow oil. TLC (silica gel; 30% acetone/hexanes) major spot at $R_f=0.39$.

b)

3,6-Dihydro-4-methyl-6-(3-nitrophenyl)-2-oxo-1,5(2H)-pyrimidinedicarboxylic acid, 5-(1-methylethyl) 1-[2-[methyl(phenylmethyl)amino]ethyl]ester, monohydrochloride A solution of the crude ester product from part (a) (4.09 g., 5.94 mmole) in tetrahydrofuran/methanol (20 ml. each) is treated with 5N hydrochloric acid (4.0 ml., pH 1). After stirring at room temperature for 4 hours, the reaction mixture is evaporated, diluted with water, and extracted with ethyl acetate. The organic phase is washed with saturated sodium bicarbonate and saturated sodium chloride, dried over anhydrous magnesium sulfate, and evaporated to give a yellow oil. This residue is taken up in ether, treated with 1.2N methanolic hydrochloric acid (6.0 ml.), capped, and allowed to stand at room temperature for one hour. The mixture is evaporated and crystallized from ethanol. Two additional crops also crystallize. All three are combined and triturated with ether to give 1.220 g. of 3,6-dihydro-4-methyl-6-(3-nitrophenyl)-2-oxo-1,5(2H)-pyrimidinedicarboxylic acid, 5-(1-methylethyl) 1-[2-[methyl(phenylmethyl)amino]ethyl]ester, monohydrochloride; m.p. 183°–185°. TLC(silica gel; 10% methanol/dichloromethane) $R_f=0.44$.

Anal. calc'd. for $C_{26}H_{30}N_4O_7 \cdot HCl$: C, 57.09; H, 5.71; N, 10.24; Cl, 6.48. Found: C, 57.20; H, 5.74; N, 10.32; Cl, 6.27.

EXAMPLE 29

6-(2,3-Dichlorophenyl)-3,6-dihydro-4-methyl-2-oxo-1,5i2H]-pyrimidinedicarboxylic acid, 5-ethyl 1-[2-[methyl(phenylmethyl)amino]ethyl]ester, monooxalate salt a)

6-(2,3-Dichlorophenyl)-2-methoxy-4-methyl-1,5(6H)-pyrimidinedicarboxylic acid, 5-ethyl 1-[2-[methyl(phenylmethyl)amino]ethyl]ester A solution of 1,4-dihydro-2-methoxy-6-methyl-4-(2,3-dichlorophenyl)-5-pyrimidinecarboxylic acid, ethyl ester (4.09 g., 9.90 mmole) and dry triethylamine (5.58 ml., 40.0 mmole) in dichloromethane (40 ml.) in an ice bath under argon is treated via gas tight syringe with a 1.3M solution of phosgene in benzene (9.9 ml., 12.9 mmole) and stirred at 0° for 2 hours. The resulting mixture is then treated with N-benzyl-N-methyl ethanolamine (2.4 ml., 14.8 mmole) and stirred at room temperature overnight. The reaction is then partitioned between ethyl acetate and saturated sodium bicarbonate. The organic phase is washed with saturated sodium chloride, dried over potassium carbonate, and evaporated. The residue is flash chromatographed to give 1.09 g. of 6-(2,3-dichlorophenyl)-2-methoxy-4-methyl-1,5(6H)-pyrimidinedicarboxylic acid, 5-ethyl 1-[2-[methyl(phenylmethyl)amino]ethyl]ester as a clear oil. TLC (silica gel; 15% ethyl acetate/dichloromethane) $R_f=0.39$.

b)

6-(2,3-Dichlorophenyl)-3,6-dihydro-4-methyl-2-oxo-1,5(2H)-pyrimidinedicarboxylic acid, 5-ethyl 1-[2-[methyl(phenylmethyl)amino]ethyl]ester, monooxalate salt A solution of the ester product from part (a) (1.09 g., 2.04 mmole) in tetrahydrofuran/methanol (20 ml. each) is treated with 5N hydrochloric acid (5.0 ml.) and stirred at room temperature for 3 hours. The reaction is quenched with saturated sodium bicarbonate and extracted with ethyl acetate. The organic phase is washed with saturated sodium chloride, dried over anhydrous magnesium sulfate, and evaporated. The free base (1.55 g., 3.17 mmole) is taken up in isopropanol (31 ml.) and treated with oxalic acid (349 mg., 3.49 mmole). After unsuccessful attempts to crystalize from isopropanol, the desired oxalic salt (1.0 g.) is crystallized from acetonitrile/isopropyl ether. A second crop (130 mg.) crystallizes from the mother liquor. The two crops are combined and recrystallized from acetonitrile/isopropyl ether to give 992 mg. of the desired monooxalate salt. Recrystallization from ethyl acetate/methanol (trace) gives 420 mg. of white crystals. A second crop of about 400 mg. precipitates from the mother liquor after rinsing the first crop with ether. These two crops are combined and triturated with ether to give 760 mg. of 6-(2,3-dichlorophenyl)-3,6-dihydro-4-methyl-2-oxo-1,5(2H)-pyrimidinedicarboxylic acid, 5-ethyl 1-[2-[methyl(phenylmethyl)amino]ethyl]ester as white crystals; m.p. gradual 105°–155°. TLC(silica gel; 10% methanol/dichloromethane) $R_f=0.51$.

Anal calc'd. for $C_{25}H_{27}Cl_2N_3O_5 \cdot C_2H_2O_4$: C, 53.12; H, 4.79; N, 6.88; Cl, 11.61. Found: C, 52.98; H, 4.69; N, 6.93; Cl, 11.61.

EXAMPLE 30

3,6-Dihydro-4-methyl-6-(3-nitrophenyl)-2-oxo-1,5(2H)-pyrimidinedicarboxylic acid, 1-(1-methylethyl) 5-[2-[methyl(phenylmethyl)amino]ethyl]ester, monohydrochloride a)

1,4-Dihydro-2-methoxy-6-methyl-4-(3-nitrophenyl)-5-pyrimidinecarboxylic acid, 2-[methyl(phenylmethyl)amino]ethyl ester A solution of 2-[(3-nitrophenyl)carboxylic methylene]-3-oxobutanoic acid, 2-[methyl(phenylmethyl)amino]ethyl ester (5.0 g., 10.6 mmole) in dimethylformamide (10 ml.) is treated with 2-methylpseudourea hydrogen sulfate (2.37 g., 13.78 mmole) and sodium bicarbonate (6.0 g., 71.4 mmole). The reaction is allowed to stir at room temperature for one hour and then heated at 70° for 16 hours. After cooling to room temperature, it is diluted with etherdichloromethane (75:25), filtered, and the filtrate is washed with water and brine. After drying over magnesium sulfate, the solvent is evaporated to give a yellow oil. Flash chromatography using 3% methanol in dichloromethane gives 2.52 g. of 1,4-dihydro-2-methoxy-6-methyl-4-(3-nitrophenyl)-5-pyrimidinecarboxylic acid, 2-[methyl(phenylmethyl)amino]ethyl ester.

b)

3,6-Dihydro-4-methyl-6-(3-nitrophenyl)-2-oxo-1,5(2H)-pyrimidinedicarboxylic acid, 1-(1-methylethyl) 5-[2-[methyl(phenylmethyl)amino]ethyl]ester, monohydrochloride A solution of the product from part (a) (2.0 g., 4.57 mmole) in dichloromethane (7.0 ml.) and pyridine (1.5 ml., 18.3 mmole) is cooled to 0° under argon and treated with isopropyl chloroformate (0.65 ml., 5.48 mmole). After the addition is completed, the cooling bath is removed and the reaction is allowed to stir at room temperature for 2 hours. The solvent is removed in vacuo and the residue is dissolved in methanol (12 ml.). This is then treated with 2.5N hydrochloric acid (50 ml.) and the reaction is allowed to stir at room temperature for one hour. The methanol is evaporated, and the residue is treated with 1N sodium hydroxide until pH of about 10 to 11 and then is extracted with chloroform. The combined extracts are washed with brine and dried over anhydrous magnesium sulfate. Evaporation gives a colorless foam which is dissolved in ether and treated with ethereal hydrochloric acid (4.5 ml. of 1.2N solution). The colorless solid that precipitates out is filtered and dried at 70° under high vacuum to give 2.2 g. of 3,6-dihydro-4-methyl-6-(3-nitrophenyl)-2-oxo-1,5(2H)-pyrimidinedicarboxylic acid, 1-(1-methylethyl) 5-[2-[methyl(phenylmethyl)amino]ethyl]ester, monohydrochloride; m.p. foams at 128° (softens above 105°).

EXAMPLE 31

3,6-Dihydro-4-methyl-6-(3-nitrophenyl)-2-oxo-1,5(2H)-pyrimidinedicarboxylic acid, 1-[1-(phenylmethyl)-4-piperidinyl]5-(1-methylethyl) ester, monohydrochloride a)

2-Methoxy-4-methyl-6-(3-nitrophenyl)-1,5(6H)-pyrimidinedicarboxylic acid, 1-[1-(phenylmethyl)-4-piperidinyl]5-(1-methylethyl) ester A solution of 1,4-dihydro-2-methoxy-6-methyl-4-(3-nitrophenyl)-5-pyrimidinecarboxylic acid, 1-methylethyl ester (5.03 g., 15.1 mmole) [prepared as set forth in Example 11 (a)] and dry triethylamine (10.5 ml., 75.4 mmole) in dichloromethane (30 ml.) in an ice bath under argon is treated dropwise via gas tight syringe with a 1.3M solution of phosgene in benzene (15.1 ml., 19.6 mmole). The resulting mixture is stirred in the bath for 20 hours. After cooling in a fresh ice bath, the mixture is treated with more triethylamine (5.5 ml., 39.5 mmole) and 1.3M phosgene in benzene solution (7.5 ml., 9.8 mmole). After 4 hours stirring in the bath, the reaction is treated with N-benzyl-4-hydroxypiperidine (3.75 g., 19.6 mmole) and stirred at room temperature for 18 hours. The reaction is then diluted with dichloromethane and washed with water and saturated sodium chloride. The evaporated organic phase is then flash chromatographed to give 4.1 g. of 2-methoxy-4-methyl-6-(3-nitrophenyl)-1,5(6H)-pyrimidinedicarboxylic acid, 1-[1-(phenylmethyl)-4-piperidinyl]5-(1-methylethyl) ester as an oil.

b)

3,6-Dihydro-4-methyl-6-(3-nitrophenyl)-2-oxo-1,5(2H)-pyrimidinedicarboxylic acid, 1-1-(phenylmethyl)-4-piperidinyl]5-(1-methylethyl) ester, monohydrochloride A solution of the ester product from part (a) (1.22 g., 2.21 mmole) in tetrahydrofuran and methanol (18 ml. each) is treated with 1N hydrochloric acid (3.0 ml., pH 1), and stirred at room temperature for 90 minutes. The reaction is quenched with saturated sodium bicarbonate and partially evaporated. The remaining aqueous phase is then extracted with ethyl acetate. The combined organic phase is washed with saturated sodium chloride, dried over potassium carbonate, and evaporated. The residue is taken up in ether and treated with 1.2M ethereal hydrochloric acid (3.0 ml., 3.6 mmole). The solids which precipitate are filtered and vacuum dried. The resulting impure product is crystallized from isopropanol and triturated with acetonitrile/ether to give 944 mg. of 3,6-dihydro-4-methyl-6-(3-nitro-phenyl)-2-oxo-1,5(2H)-pyrimidinedicarboxylic acid, 1-[1-(phenylmethyl)-4-piperidyl]5-(1-methylethyl) ester, monohydrochloride as a colorless solid; m.p. greater than 250°. TLC (silica gel; 10% methanol/dichloromethane) $R_f$=0.54.

Anal. calc'd. for $C_{28}H_{32}N_4O_7$ HCl 0.37 $H_2O$: 58.01; H, 5.87; N, 9.66; Cl, 6.12. Found: C, 58.01; H, 5.87; N, 9.53; Cl, 6.12.

EXAMPLES 32–55

Following the procedures of Examples 2 to 25 and 27 to 31, the substituted 1,4-dihydro-2-methoxy-5-pyrimidinecarboxylic acid ester shown in Col. I is reacted to give the 1,5(6H)-pyrimidinedicarboxylic acid ester shown below in Col. II. Treatment with hydrochloric acid yields the product shown in Col. III.
Col. I
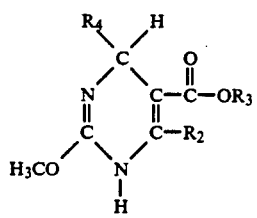
Col. II
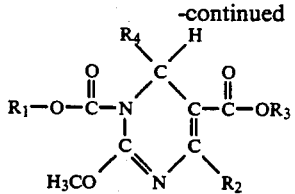
Col. III
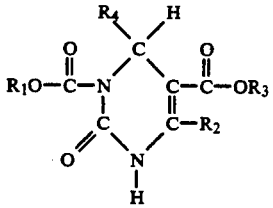

| Example | R₃ | R₂ | R₄ | R₁ |
|---|---|---|---|---|
| 32 | —C₂H₅ | —CH₃ | | —C₂H₅ |
| 33 | —CH—(CH₃)₂ | —CH₃ | 2-SCH₃-phenyl | —CH—(CH₃)₂ |
| 34 | —CH—(CH₃)₂ | —CH₃ | 2-OCH₃-phenyl | —(CH₂)₂—N(piperazine)-phenyl |
| 35 | —(CH₂)₂—O—CH₂-phenyl | —CH₃ | 2-NO₂-6-Cl-phenyl | —(CH₂)₂—O—CH₂-phenyl |
| 36 | CH₃-CH—CH₂—N(CH₃)— | —CH₃ | 2-Cl-phenyl | —CH—(CH₃)₂ |
| 37 | —C₂H₅ | —CH₃ | 4-NO₂-phenyl | —C₂H₅ |
| 38 | —C₂H₅ | —CH₃ | 5-O₂N-naphthyl | —C₂H₅ |
| | | | 6-F₃C-naphthyl | |

-continued

| Example | R₃ | R₂ | R₄ | R₁ |
|---|---|---|---|---|
| 39 | —C₂H₅ | —CH₃ | 2-methylphenyl | —C₂H₅ |
| 40 | —CH₂—CH—(CH₃)₂ | —CH₃ | 2-methyl-6-OCHF₂-phenyl | —C₂H₅ |
| 41 | —C₂H₅ | —CH₃ | 3-methyl-2-SCH₃-pyridyl | —(CH₂)₂—O—C₂H₅ |
| 42 | —(CH₂)₂—S—CH₃ | —CH₃ | 2-methylthienyl | —(CH₂)₂—S—CH₃ |
| 43 | phenyl-S—(CH₂)₂— | —CH₃ | N-benzyl-vinyl imine | —C₂H₅ |
| 44 | —(CH₂)₂—N(CH₃)₂ | —CH₃ | N-benzyl-7-methylindolyl | —C₂H₅ |

-continued

| Example | R₃ | R₂ | R₄ | R₁ |
|---|---|---|---|---|
| 45 | —CH₂—C(=O)—N(CH₃)₂ | —CH₃ | benzo-fused ring with N (CH=N) | —CH₂—C(=O)—N(CH₃)₂ |
| 46 | —C₂H₅ | —CH₂—C₆H₅ | quinoline-type (N in ring) | —C₂H₅ |
| 47 | —C₂H₅ | —CF₃ | isoquinoline-type (N in ring) | —C₂H₅ |
| 48 | —C₂H₅ | —CH₂—O—CH₃ | benzothiazole | —C₂H₅ |
| 49 | —C₂H₅ | —CH₂—O—C₆H₅ | benzoxazole | —C₂H₅ |
| 50 | —C₂H₅ | —CH₂—S—C₂H₅ | N-benzyl-N=CH-phenyl | —C₂H₅ |
| 51 | —C₂H₅ | —CH₂—S—CH₂—C₆H₅ | benzo[d]isoxazole (N=N—O) | —C₂H₅ |

-continued

| Example | R₃ | R₂ | R₄ | R₁ |
|---------|------|------|------|------|
| 52 | —C₂H₅ | —CH₃ | ![structure: phenyl with =N—O—N= oxime group] | —C₂H₅ |

The N-protecting groups in Examples 43, 44, and 50 are removed as the last step in the synthesis.

EXAMPLE 53

3,6-Dihydro-4-methyl-6-(3-nitrophenyl)-2-oxo-1,5(2H)-pyrimidinedicarboxylic acid, 5-(1-methylethyl) 1-[(S)-phenylethyl]ester A solution of (S)-(-)phenylethyl alcohol (1.0 g., 8.2 mmole) in acetonitrile (10 ml.) and pyridine (1.0 ml.) is treated at 0° under argon with 4-nitrophenyl chloroformate (1.65 g., 8.2 mmole). The reaction is stirred at 0° for 30 minutes and at room temperature for one hour. It is then treated with 1,4-dihydro-2-methoxy-6-methyl-4-(3-nitrophenyl)-5-pyrimidinecarboxylic acid, 1-methylethyl ester (2.1 g., 6.3 mmole) [prepared as set forth in Example 11(a)] followed by triethylamine (1.7 ml.) and 4-dimethylaminopyridine (75 mg., 0.63 mmole). The reaction is stirred at room temperature for 6 hours and at 75° for 24 hours. The solvent is evaporated and the residue is taken up in tetrahydrofuran (20 ml.) and treated with 2N hydrochloric acid until pH 2.0. The reaction is then stirred at room temperature overnight, after which most of the solvent is removed under vacuum. The residue is extracted with ether several times and the combined extract is washed with 5% potassium carbonate and brine and then dried over anhydrous magnesium sulfate. The solvent is evaporated and the residue is purified by flash chromatography 10% ethyl acetate in dichloromethane). The product is crystallized from isopropyl ether-dichloromethane to give 820 mg. of 3,6-dihydro-4-methyl-6-(3-nitrophenyl)-2-oxo-1,5(2H)-pyrimidinedicarboxylic acid, 5-(1-methylethyl) 1-[(S)-phenylethyl]ester as a colorless solid; m.p. 149°-160°.

Anal. calc'd for $C_{24}H_{25}N_3O_7$: C, 61.66; H, 5.39; N, 8.98. Found: C, 61.47; H, 5.71; N, 8.91.

EXAMPLE 54

3,6-Dihydro-4-methyl-6-(3-nitrophenyl)-2-oxo-1,5(2H]-pyrimidinedicarboxylic acid, 5-(1-methylethyl)-1-[(S)-1-methyl-2-[methyl(phenylmethyl)amino]ethyl]ester a)

3,6-Dihydro-4-methyl-6-(3-nitrophenyl)-2-oxo-1,5(2H]-pyrimidinedicarboxylic acid, 5-(1-methylethyl) 1-(4-nitrophenyl) ester A solution of 1,4-dihydro-2-methoxy-6-methyl-4-(3-nitrophenyl)-5-pyrimidinecarboxylic acid, 1-methylethyl ester (500 mg., 1.5 mmole) [prepared as set forth in Example 11(a)] and pyridine (0.61 ml., 7.5 mmole) in dichloromethane (4.0 ml.) in an ice bath under argon is treated with 4-nitrophenyl chloroformate (363 mg., 1.8 mmole). After stirring at 0° for one hour, the reaction mixture is evaporated. The residue is taken up in tetrahydrofuran-methanol (4 ml. each) and treated with 3N hydrochloric acid (2 ml., pH 1). The reaction is stirred at room temperature for several hours and evaporated. The residue is partitioned between chloroform and saturated sodium bicarbonate solution. The organic phase is washed with saturated sodium chloride solution, dried (MgSO$_4$), and evaporated. The residue is purified by flash chromatography (5% dichloromethane in ether) and crystallized from isopropyl ether to give 574 mg. of 3,6-dihydro-4-methyl-6-(3-nitrophenyl)-2-oxo-1,5(2H)-pyrimidinedicarboxylic acid, 5-(1-methylethyl) 1-(4-nitrophenyl) ester; m.p. 138°-140°. TLC (silica gel; 40% acetone/hexane) $R_f = 0.20$.

b.

3,6-Dihydro-4-methyl-6-(3-nitrophenyl)-2-oxo-1,5(2H)-pyrimidinedicarboxylic acid, 5-(1-methylethyl) 1-[(S)-1-methyl-2-[methyl(phenylmethyl)amino]ethyl]-ester A mixture of the product from part (a) (227 mg., 0.57 mmole) and (S)-1-methyl-2-[methyl(phenylmethyl-)amino[ethanol (135 mg., 0.74 mmole) in acetonitrile (5.7 ml.) under argon is heated at 50° for 72 hours. The mixture is evaporated and flash chromatographed (5% dichloromethane in ether) to give 0.33 g. of crude product as a yellow oil. This material is taken up in ether, treated with ethanolic hydrochloric acid, and evaporated. Trituration with ether gives 204 mg. of 3,6-dihydro-4-methyl-6-(3-nitrophenyl)-2-oxo-1,5(2H)-pyrimidinedicarboxylic acid, 5-(1-methylethyl) 1-[(S)-1-methyl-2-[methyl(phenylmethyl)amino]ethyl] ester as colorless crystals; m.p. 120°-150° (dec.). TLC (silica gel; 5% dichloromethane/ether) $R_f = 0.42$.

Anal. calc'd for $C_{27}H_{32}N_4O_7 \cdot 0.8H_2O$: C, 56.45; H, 5.90; N, 9.75; Cl, 6.17. Found: C, 56.57; H, 6.30; N, 9.25; Cl, 6.54.

EXAMPLE 55

3,6-Dihydro-4-methyl-6-[2-(trifluoromethyl)phenyl]-2-thioxo-1,5(2H)-pyrimidinedicarboxylic acid, diethyl ester a)

1,4-Dihydro-6-methyl-4-[2-(trifluoromethyl)phenyl]-2-[(phenylmethyl)thio]-5-pyrimidinecarboxylic acid, ethyl ester A solution of 2-[[2-(trifluoromethyl)phenyl]methylene]-3-oxobutanoic acid, ethyl ester (2.8 g., 10.0 mmole) in dry dimethylformamide is treated with S-(benzyl)thiopseudourea hydrochloride (2.43 g., 12.0 mmole) and sodium acetate (984 mg., 12.0 mmole). The reaction mixture is stirred at room temperature for 2 hours and then heated at 60° for 4 hours. The reaction is then cooled to room temperature, diluted with ether, and filtered. The filtrate is washed with water, sodium bicarbonate, and brine. After drying over anhydrous magnesium sulfate, the solvent is evaported. The residue is purified by flash chromatography (2% ethyl acetate in dichloromethane) to provide 3.6 g. of 1,4-dihydro-6-methyl-4-[2-(trifluoromethyl)phenyl]-2-[(phenylmethyl)thio]-5-pyrimidinecarboxylic acid, ethyl ester as a light yellow foam. TLC (silica gel; ethyl acetate/hexanes, 30:70) $R_f = 0.51$.

b)

4-Methyl-6-[2-(trifluoromethyl)phenyl]-2-[(phenylmethyl)thio]-1,5(6H)-pyrimidinedicarboxylic acid, diethyl ester A solution of 1,4-dihydro-6-methyl-4-[2-(trifluoromethyl)phenyl]-2-[(phenylmethyl)thio]-5-pyrimidinecarboxylic acid, ethyl ester (3.3 g., 7.6 mmole) in dichloromethane (20 ml.) and pyridine (1.2 ml.) is cooled to 0° under argon and treated dropwise with ethyl chloroformate (0.9 ml., 9.0 mmole). A catalytic amount of 4-dimethylamino pyridine is added and the reaction is allowed to warm to room temperature. The reaction is then stirred overnight and then diluted with ethyl acetate. The resulting solution is washed with 1N hydrochloric acid, sodium bicarbonate and brine. After drying over anhydrous magnesium sulfate, the solvent is stripped to provide a yellow foam. Crystallization from hexanes provides 3.11 g. of yellow crystalline 4-methyl-6-[2-(trifluoromethyl)phenyl]-2-[(phenylmethyl)thio]-1,5(6H)-pyrimidinedicarboxylic acid, diethyl ester; m.p. 85.5°–87.5°. TLC (silica gel; ethyl acetate/hexanes, 30:70) $R_f=0.64$.

c)
3,6-Dihydro-4-methyl-6-[2-(trifluoromethyl)phenyl]-2-thioxo-1,5(2H)-pyrimidinedicarboxylic acid, diethyl ester A solution of 4-methyl-6-[2-(trifluoromethyl)phenyl]-2-[(phenylmethyl)thio]-1,5(6H)-pyrimidinedicarboxylic acid, diethyl ester (1.0 g., 1.97 mmole) in dry acetonitrile (5 ml.) is treated with bromotrimethylsilane (1.0 ml., 7.57 mmole) under argon. The reaction is heated to 60° overnight and then cooled to room temperature. Some starting material is still present (TLC). The acetonitrile and excess bromotrimethylsilane are evaporated and the resulting residue is diluted with ethyl acetate. This solution (yellow) is washed with 5% sodium bicarbonate and brine, and is dried over anhydrous magnesium sulfate. The solvent is evaporated off and the residue is flash chromatographed eluting with 15% acetone in hexanes. The fractions containing the desired product are combined, evaporated, and the residue is crystallized from isopropyl ether/hexanes to give 405 mg. of 3,6-dihydro-4-methyl-6-[2-(trifluoromethyl)phenyl]-2-thioxo-1,5(2H)-pyrimidinedicarboxylic acid, diethyl ester as a yellow solid; m.p. 106°–108°. TLC (silica gel; ethyl acetate/hexanes, 40:60) $R_f=0.48$.

Anal. calc'd. for $C_{18}H_{19}F_3N_2O_4S$: C, 51.92; H, 4.60; N, 6.73; S, 7.70; F, 13.69. Found: C, 51.99; H, 4.63; N, 6.61; S, 7.86; F, 13.70.

EXAMPLES 56

3,6-Dihydro-4-methyl-6-(2-nitrophenyl)-2-thioxo-1,5(2H)-pyrimidinedicarboxylic acid, diethyl ester a)
1,4-Dihydro-6-methyl-4-(2-nitrophenyl)-2-[(phenylmethyl)thio]-5-pyrimidinecarboxylic acid, ethyl ester, hydrochloride A solution of 2-[(2-nitrophenyl)methylene]-3-oxobutanoic acid, ethyl ester (3.09 g., 11.4 mmole) in dry dimethylformamide (7.0 ml.) under argon is treated with S-(benzyl)thiopseudourea, hydrochloride (2.31 g., 11.4 mmole) and sodium acetate (984 mg., 12.0 mmole). The reaction is heated at 60° for 4 hours and then allowed to cool to ambient temperature. It is diluted with ethyl acetate and the solid is filtered off. The filtrate is washed with water, sodium bicarbonate, and brine. After drying over anhydrous magnesium sulfate, the solvent is stripped off to yield a yellow foam. This material is dissolved in isopropanol (30 ml.) and treated with methanolic hydrochloric acid (3.5 ml. of 4N solution). Most of the methanol is evaporated and the solution is refrigerated overnight. The solid that precipitates out is filtered, washed with isopropanol and dried to provide 4.4 g. of 1,4-dihydro-6-methyl-4-(2-nitrophenyl)-2-[(phenylmethyl)thio]-5-pyrimidinecarboxylic acid, ethyl ester, hydrochloride as a light yellow solid. An analytically pure sample is obtained by recrystallization from isopropanol-dichloromethane; m.p. 151.5°–153°. TLC (silica gel; ethyl acetate/hexanes, 40:60) $R_f=0.38$.

Anal calc'd. for $C_{21}H_{21}N_3O_4S\cdot HCl$: C, 56.31; H, 4.95; N, 9.38; S, 7.16; Cl, 7.91. Found: C, 56.18; H, 5.15; N, 9.15; S, 6.90; Cl, 7.87.

b)
4-Methyl-6-(2-nitrophenyl)-2-[(phenylmethyl)thio]-1,5(6H)-pyrimidinedicarboxylic acid, diethyl ester A solution of 1,4-dihydro-6-methyl-4-(2-nitrophenyl)-2-[phenylmethyl)thio]-5-pyrimidinecarboxylic acid, ethyl ester, hydrochloride (4.0 g., 10.0 mmole) in dichloromethane (20 ml.) and pyridine (2.16 ml., 26.7 mmole) is cooled to 0° under argon and treated dropwise with ethyl chloroformate (1.1 ml., 11.0 mmole). After the addition is completed, the cooling bath is removed and the reaction mixture is allowed to stir at room temperature for 3 hours. It is then diluted with ethyl acetate and the resulting solution is washed with water, 1N hydrochloric acid, sodium bicarbonate, and brine. After drying over anhydrous magnesium sulfate, the solvent is stripped and the residue is crystallized from ether-hexanes to give 4.01 g. of 4-methyl-6-(2-nitrophenyl)-2-[(phenylmethyl)thio]-1,5(6H)-pyrimidinedicarboxylic acid, diethyl ester as a yellow solid; m.p. 110°–112°. TLC (silica gel; ethyl acetate/hexanes, 40:60) $R_f=0.53$.

Anal calc'd. for $C_{24}H_{25}N_3O_6S$: C,59.61; H,5.21; N,8.69; S,6.63. Found: C,59.82; H,5.32; N,8.52; S,6.66.

c)
3,6-Dihydro-4-methyl-6-(2-nitrophenyl)-2-thioxo-1,5(2H)-pyrimidinedicarboxylic acid, diethyl ester A suspension of 4-methyl-6-(2-nitrophenyl)-2-[(phenylmethyl)thio]-1,5(6H)-pyrimidinedicarboxylic acid, diethyl ester (2.0 g., 4.14 mmole) in dry acetonitrile (10 ml.) under argon is treated with bromotrimethylsilane (2.5 ml.) using a gas tight syringe. The reaction mixture is heated at 70° for 36 hours and then cooled to room temperature. The solvent is stripped and the residue is purified by flash chromatography (25% ethyl acetate in hexanes). The desired product is crystallized from isopropyl etherhexanes to give 590 mg. of 3,6-dihydro-4-methyl-6-(2-nitrophenyl)-2-thioxo-1,5(2H)-pyrimidinedicarboxylic acid, diethyl ester; m.p. 130°–132°. TLC (silica gel; ethyl acetate/hexanes, 50:50) $R_f=0.48$.

Anal. calc'd. for $C_{17}H_{19}N_3O_6S$: C,51.90; H,4.87; N,10.68; S,8.15. Found: C,51.94; H,4.69; N,10.33; S,8.04.

EXAMPLE 57

6-(2,3-Dichlorophenyl)-3,6-dihydro-4-methyl-2-thioxo-1,5(2H)-pyrimidinedicarboxylic acid, 5-methyl 1-ethyl ester a) S-(4-Methoxybenzyl)thiopseudourea, hydrochloride A suspension of thiourea (38 g., 50.0 mmole) in dry tetrahydrofuran (40 ml.) is cooled to 0° under argon and is treated dropwise with 4-methoxybenzylchloride (8.0 g., 50.0 mmole). After the addition is completed, the cooling bath is removed and the reaction is allowed to stir at room temperature for 2 hours. It is then heated at 60°–65° for 4 hours whereupon a colorless voluminous precipitate is formed. The reaction is allowed to cool down to room temperature and is diluted with anhydrous ether. The solid is filtered off and washed with anhydrous ether to give 10.92 g. of S-(4-methoxybenzyl)thiopseudourea, hydrochloride; m.p. 161°–163.5°.

Anal. calc'd. for $C_9H_{12}N_2OS \cdot HCl$: C,46.45; H,5.63; N,12.04; S,13.78; Cl, 15.23. Found: C,46.48; H,5.64; N,12.25; S,13.74; Cl, 15.31.

b) 4-(2 3-Dichlorophenyl)-1 4-dihydro-2-[[(4-methoxyphenyl)methyl]thio]-6-methyl-5-pyrimidinecarboxylic acid, methyl ester A solution of 2-[(2,3-dichlorophenyl)methylene]-3-oxobutanoic acid, methyl ester (1.36 g., 5.0 mmole) in dry dimethylformamide (5 ml.) is treated with S-(4-methoxybenzyl)thiopseudourea, hydrochloride (1.16 g., 5.0 mmole) and sodium acetate (420 mg., 5.0 mmole) under argon at room temperature. The reaction is heated at 60° for 4 hours and then allowed to cool down to room temperature. It is diluted with ethyl acetate and the solid is filtered off. The filtrate is washed with water, sodium bicarbonate, and brine. After drying over anhydrous magnesium sulfate, the solvent is evaporated to provide 2.21 g. of 4-(2,3-dichlorophenyl)-1,4-dihydro-2-[[(4-methoxyphenyl)methyl]thio]-6-methyl-5-pyrimidinecarboxylic acid, methyl ester as a light yellow foam. TLC (silica gel; ethyl acetate/hexanes 40:60) $R_f = 0.38$.

c) 6-(2,3-Dichlorophenyl)-4-methyl-2-[[(4-methoxyphenyl]methyl]thio-1,5(6H)-pyrimidinedicarboxylic acid, 5-methyl 1-ethyl ester A solution of 4-(2,3-dichlorophenyl)-1,4-dihydro-2-[[(4-methoxyphenyl)methyl]thio]-6-methyl-5-pyrimidinecarboxylic acid, methyl ester (2.17 g., 4.80 mmole) in dichloromethane (10 ml.) and pyridine (0.8 ml.) is treated dropwise with ethyl chloroformate (0.6 ml., 6.5 mmole) at 0° under argon. After the addition is completed, the reaction mixture is allowed to warm to room temperature and stirred for 3 hours. Anhydrous ether (60 ml.) is added and the resulting solution is washed with water, 1N hydrochloric acid, sodium bicarbonate, and brine. It is dried over magnesium sulfate and evaporated to provide a yellow foam. Crystallization from ether-hexanes provides 2.25 g. of 6-(2,3-dichlorophenyl)-4-methyl-2-[[(4-methoxyphenyl)methyl]thio]-1,5(6H)-pyrimidinedicarboxylic acid, 5-methyl 1-ethyl ester; m.p. 134°-135°. TLC (silica gel; ethyl acetate:hexanes, 40:60) $R_f = 0.53$.

Anal. calc'd. for $C_{24}H_{24}Cl_2N_2O_5S$: C,55.07; H,4.62; N,5.35; S,6.12; Cl, 13.55. Found: C,55.15; H,4.47; N,5.42; S,6.33; Cl, 13.47.

d) 6-(2,3-Dichlorophenyl)-3,6-dihydro-4-methyl-2-thioxo-1,5(2H)-pyrimidinedicarboxylic acid, 5-methyl 1-ethyl ester A suspension of the ester product from part (c) (1.0 g., 1.91 mmole) in anhydrous benzene (5 ml.) under argon is treated with trifluoroacetic acid (0.5 ml.). The resulting solution is heated at 70° (oil bath temperature) for 30 hours. The reaction is then cooled to ambient temperature and the solvent stripped off. The residue is purified by flash chromatography on silica gel (5% ethyl acetate in dichloromethane). The resulting product is crystallized from dichloromethane-isopropyl ether to give 589 mg. of yellow solid product. This material is combined with a previous batch and recrystallized from dichloromethane-benzene-hexanes to give an analytically pure sample of 6-(2,3-dichlorophenyl)-3,6-dihydro-4-methyl-2-thioxo-1,5(2H)-pyrimidinedicarboxylic acid, 5-methyl 1-ethyl ester; m.p. 190°-191°. TLC (silica gel; ethyl acetate hexanes, 40:60) $R_f = 0.43$.

Anal. calc'd. for $C_{16}H_{16}Cl_2N_2O_4S$: C,47.65; H,4.00; N,6.95; S,7.95; Cl, 17.56. Found: C,47.91; H,3.97; N,6.66; S,7.92; Cl, 17.50.

EXAMPLE 58

3,6-Dihydro-6-(2-methoxyphenyl)-4-methyl-2-thioxo-1,5(2H)-pyrimidinedicarboxylic acid, diethyl ester a) 1,4-Dihydro-4-(2-methoxyphenyl)-2-[[(4-methoxyphenyl)methyl]thio]-6-methyl-5-pyrimidinecarboxylic acid, ethyl ester A mixture of 2-[(2-methoxyphenyl)methylene]-3-oxobutanoic acid, ethyl ester (1.61 g., 6.5 mmole), S-(4-methoxybenzyl)thiopseudourea, hydrochloride (1.51 g., 6.5 mmole), and sodium acetate (0.54 g., 6.5 mmole) in dimethylformamide (7 ml.) is stirred and heated at 60° for 4 hours, cooled and diluted with ether. After extraction with water, sodium bicarbonate, and brine, the dried solution is evaporated to give 2.8 g. of crude 1,4-dihydro-4-(2-methoxyphenyl)-2-[[(4-methoxyphenyl)methyl]thio]-6-methyl-5-pyrimidinecarboxylic acid, ethyl ester as an oil.

b) 6-(2-Methoxyphenyl)-2-[[(4-methoxyphenyl)methyl]thio]-4-methyl-1,5(6H)-pyrimidinedicarboxylic acid, diethyl ester A solution of the crude ethyl ester product from part (a) (2.8 g., 6.5 mmole) in dichloromethane (15 ml.) containing pyridine (1.1 ml.) is cooled to 5° and treated dropwise with ethyl chloroformante (0.8 ml., 8.0 mmole) and then stirred at room temperature for 4 hours. After dilution with ether, the solution is washed with water, 1N hydrochloric acid, saturated sodium bicarbonate, and brine. The dried solution is evaporated to give 2.0 g. of yellow solid 6-(2-methoxyphenyl)-2-[[(4-methoxyphenyl)methyl]thio]-4-methyl-1,5(6H)-pyrimidinedicarboxylic acid, diethyl ester; m.p. 116°-118°.

Anal. calc'd. for $C_{26}H_{31}N_2O_6S$: C, 62.50; H, 6.25; N, 5.60. Found: C, 62.34; H, 6.01; N, 5.49.

3,6-Dihydro-6-(2-methoxyphenyl)-4-methyl-2-thioxo-1,5(2H)-pyrimidinedicarboxylic acid, diethyl ester A solution of the diethyl ester product from part (b) (2.0 g., 4.0 mmole) and trifluoroacetic acid (1.1 ml.) in benzene (12 ml.) is heated at 70° for 30 minutes. The solvent is evaporated and the residue is flash chromatographed using dichloromethane:ethyl acetate (98:2) to give 0.7 g. of a mixture containing the desired product. This material is combined with 0.3 g. of a similar mixture from a previous run and flash chromatographed using ethyl acetate:hexanes (1:3) to give 0.44 g. of yellow solid 3,6-dihydro-6-(2-methoxyphenyl)-4-methyl-2-thioxo-1,5(2H)-pyrimidinedicarboxylic acid, diethyl ester; m.p. 117°-118°. TLC (silica gel; ethyl acetate:hexanes, 1:1) $R_f = 0.55$.

Anal. calc'd. for $C_{18}H_{22}N_2O_5S$: C, 57.12; H, 5.85; N, 7.40; S, 8.47. Found: C, 56.99; H, 5.97; N, 7.19; S, 8.27.

EXAMPLE 59

6-(2-Chlorophenyl)-3,6-dihydro-4-methyl-2-thioxo-1,5 2H)-pyrimidinedicarboxylic acid, diethyl ester a)

4-(2-Chlorophenyl)-1,4-dihydro-2-[[(4-methoxylphenyl)methyl]thio]-6-methyl-5-pyrimidinecarboxylic acid, ethyl ester A solution of 2-[(2-chlorophenyl)methylene]-3-oxobutanoic acid, ethyl ester (1.26 g., 5.0 mmole), S-(4-methoxybenzyl)thiopseudourea, hydrochloride (1.16 g., 5.0 mmole) and sodium acetate (0.42 g., 5.0 mmole) in dimethylformamide is stirred and heated at 60° for 4 hours. After cooling, ether is added and the solution is extracted with ether, sodium bicarbonate, and brine, then dried and evaporated to give 2.0 g. of 4-(2-chlorophenyl)-1,4-dihydro-2-[[(4-methoxyphenyl)methyl]thio]-6-methyl-5-pyrimidinecarboxylic acid, ethyl ester as an oil.

b)

6-(2-Chlorophenyl)-2-[[(4-methoxyphenyl)methyl]thio]-4-methyl-1,5(6H)-pyrimidinedicarboxylic acid, diethyl ester A stirred solution of the ethyl ester product from part (a) (2.0 g., 4.6 mmole) in dichloromethane (12 ml.) containing pyridine (0.8 ml.) is cooled to 5° and treated dropwise with ethyl chloroformate (0.5 ml., 5.2 mmole). After stirring for 16 hours at room temperature, the solution is diluted with ether and extracted with water, 1N hydrochloric acid, saturated sodium bicarbonate and brine. The dried solution is concentrated to a small volume to allow slow crystallization. As a result, 1.0 g. of yellow product is obtained; m.p. 107°–109°. An additional 0.33 g. of product is obtained by repeat treatment of the concentrated mother liquor, in dichloromethane, with pyridine (0.4 ml.) and ethyl chloroformate (0.25 ml.) to give a total yield of 1.33 g. of 6-(2-chlorophenyl)-2-[[(4-methoxyphenyl)methyl]thio]-4-methyl-1,5(6H)-pyrimidinedicarboxylic acid, diethyl ester.

Anal. calc'd. for $C_{25}H_{27}N_2ClO_5S$: C, 59.69; H, 5.40; N, 5.57. Found: C, 60.03; H, 5.55; N, 5.53.

c)

6-(2-Chlorophenyl)-3,6-dihydro-4-methyl-2-thioxo-1,5(2H)-pyrimidinedicarboxylic acid, diethyl ester A stirred solution of the diethyl ester product from part (b) (1.3 g., 2.5 mmole) and trifluoroacetic acid (0.65 ml.) in benzene (8 ml.) is heated at 70° for 46 hours. The solvent is evaporated and the crude residue is flash chromatographed using dichloromethane:ethyl acetate (98:2) to give 0.4 g. of 6-(2-chlorophenyl)-3,6-dihydro-4-methyl-2-thioxo-1,5(2H)-pyrimidinedicarboxylic acid, diethyl ester as a yellow solid homogeneous material; m.p. 126°–128°. TLC (silica gel; dichloromethane:ethyl acetate, 98:2) $R_f=0.25$.

Anal. calc'd. for $C_{17}H_{19}N_2ClO_4S$: C, 53.32; H, 5.00; N, 7.31; Cl, 9.25; S, 8.37. Found: C, 53.02; H, 4.96; N, 7.11; Cl, 9.58; S, 8.30.

EXAMPLE 60

3,6-Dihydro-4-methyl-6-(4-nitrophenyl)-2-thioxo-1,5(2H)-pyrimidinedicarboxylic acid, diethyl ester a)

1,4-Dihydro-2-[(4-methoxyphenyl)methyl]thio]-6-methyl-4-(4-nitrophenyl)-5-pyrimidinecarboxylic acid, ethyl ester A stirred mixture of 2-[(4-nitrophenyl)methylene]-3-oxobutanoic acid, ethyl ester (1.97 g., 7.5 mmole), S-(4-methoxybenzyl)thiopseudourea, hydrochloride (1.74 g., 7.5 mmole), and sodium acetate (0.63 g., 7.5 mmole) in dimethylformamide (8 ml.) is heated at 70° for 4 hours. After cooling, ether is added and the solution is washed with water, sodium bicarbonate, and brine. The dried solution is evaporated to give 3.1 g. of crude 1,4-dihydro-2-[[(4-methoxyphenyl)methyl]thio]-6-methyl-4-(4-nitrophenyl)-5-pyrimidinecarboxylic acid, ethyl ester as an oil.

b)

2-[[(4-Methoxyphenyl)methyl]thio]-4-methyl-6-(4-nitrophenyl)-1,5(6H)-pyrimidinedicarboxylic acid, diethyl ester A solution of the ethyl ester product from part (a) (3.1 g., 7.0 mmole) and pyridine (1.2 ml.) in dichloromethane (20 ml.) is cooled to 5° and treated dropwise with ethyl chloroformate (0.92 ml., 9.0 mmole). After stirring at room temperature for 16 hours, the solution is siluted with ether and washed with water, 1N hydrochloric acid, sodium bicarbonate, and brine. The dried solution is evaporated to give 2.95 g. of 2-[[(4-methoxyphenyl)methyl]thio]-4-methyl-6-(4-nitrophenyl)-1,5(6H)-pyrimidinedicarboxylic acid, diethyl ester as an oil containing a minor impurity.

c)

3,6-Dihydro-4-methyl-6-(4-nitrophenyl)-2-thioxo-1,5(2H)-pyrimidinedicarboxylic acid diethyl ester A solution of the diethyl ester product from part (b) (2.9 g., 5.6 mmole) and trifluoroacetic acid (1.5 ml.) in benzene (20 ml.) is heated at 70° for 3 hours. The solvent is evaporated and the residue is flash chromatographed using dichloromethane:ethyl acetate (98:2) to give 1.05 g. of yellow solid 3,6-dihydro-4-methyl-6-(4-nitrophenyl)-2-thioxo-1,5(2H)-pyrimidinedicarboxylic acid , diethyl ester; m.p. 163°–165°. TLC(silica gel; ethyl acetate:hexanes, 1:1) $R_f=0.45$.

Anal. calc'd for $C_{17}H_{19}N_3O_6S$: C, 51.89; H, 4.86; N, 10.68; S, 8.14. Found: C, 52.03; H, 4.88; N, 10.56; S, 7.95.

EXAMPLE 61

3,6-Dihydro-6-(4-methoxyphenyl)-4-methyl-2-thioxo-1,5(2H)-pyrimidinedicarboxylic acid, diethyl ester a)

1,4-Dihydro-2-[[(4-methoxyphenyl)methyl]thio]-4-(4-methoxyphenyl)-6-methyl-5-pyrimidinecarboxylic acid, ethyl ester A mixture of 2-[(4-methoxyphenyl)methylene]-3-oxobutanoic acid, ethyl ester (1.49 g., 6.0 mmole), S-(4-methoxybenzyl)thiopseudourea, hydrochloride (1.4 g., 6.0 mmole) and sodium acetate (0.5 g., 6.0 mmole) in dimethylformamide (7 ml.) is stirred and heated at 70° for 4 hours. After cooling, ether is added and the mixture is washed with water, saturated sodium bicarbonate solution and brine. The dried solution is evaporated to give 2.2 g. of 1,4-dihydro-2-[[(4-methoxyphenyl)methyl]thio]-4-(4-methoxyphenyl)-6-methyl-5-pyrimidinecarboxylic acid, ethyl ester as an oil.

b)
2-[[(4-Methoxyphenyl)methyl]thio]-4-methyl-6-(4-methoxyphenyl-1,5(6H)-pyrimidinedicarboxylic acid, diethyl ester A cold solution of the ethyl ester product from part(a) (2.2 g., 5.1 mmole) and pyridine (0.86 ml.) in dichloromethane (15 ml.) is treated slowly with ethyl chloroformate (0.63 ml., 6.5 mmole). After stirring at room temperature overnight, the solution is diluted with ether and washed with water, 1N hydrochloric acid, saturated sodium bicarbonate, and brine. The dried solution is evaporated to give 2.45 g. of 2-[[(4-methoxyphenyl)methyl]thio]-4-methyl-6-(4-methoxyphenyl)-1,5(6H)-pyrimidinedicarboxylic acid as an oil containing a small amount of impurity.

c)
3,6-Dihydro-6-i4-methoxyphenyl)-4-methyl-2-thioxo-1,5i2H)-pyrimidinedicarboxylic acid, diethyl ester A solution of the crude diethyl ester product from part (b) (2.45 g., 4.9 mmole), trifluoroacetic acid (1.42 ml., 15 mmole) and ethanethiol (0.63 g., 10 mmole) in dichloromethane (25 ml.) is stirred at room temperature for 60 hours. The solvent is evaporated and the residue flash chromatographed using ethyl acetate:hexane (1:4) to give an oil which slowly solidifies to 1.15 g. of yellow solid 3,6-dihydro-6-(4-methoxyphenyl)-4-methyl-2-thioxo-1,5(2H)-pyrimidinedicarboxylic acid, diethyl ester, m.p. 130°–132°. TLC (silica gel; ethyl acetate:hexane, 1:1) $R_f$=0.45.

Anal. calc'd. for $C_{18}H_{22}N_2O_5S$: C, 57.12; H, 5.85; N, 7.40; S, 8.47. Found: C, 57.18; H, 5.88; N, 7.24; S, 8.31.

EXAMPLE 62

3,6-Dihydro-4-methyl-6-[2-(phenylmethoxy)phenyl]-2-thioxo-1,5(2H)-pyrimidinedicarboxylic acid, diethyl ester a)
1,4-Dihydro-2-[[(4-methoxyphenyl)methyl]thio]-6-methyl-4-2-(phenylmethoxy)phenyl]-5-pyrimidinecarboxylic acid, ethyl ester A mixture of 2-[[2-(phenylmethoxy)phenyl]methylene]-3-oxobutanoic acid, ethyl ester (1.94 g., 6 mmole), S-(4-methoxybenzyl)thiopseudourea, hydrochloride (1.4 g., 6 mmole), and sodium acetate (0.5 g., 6 mmole) in dimethylformamide (7 ml.) is stirred and heated at 70° for 4 hours. Ether is added to the cooled mixture which is then washed with water, sodium bicarbonate, and brine. The dried solution is evaporated to give 3.0 g. of 1,4-dihydro-2-[[(4-methoxyphenyl)methyl]thio]-6-methyl-4-[2-(phenylmethoxy)phenyl]-5-pyrimidinecarboxylic acid, ethyl ester as an oil. TLC (silica gel; ethyl acetate:hexane, 1:1) $R_f$=0.55.

b)
2-[[(4-Methoxyphenyl)methyl]thio]-4-methyl-6-[2-phenylmethoxy)phenyl]-1,5(6H)-pyrimidinedicarboxylic acid, diethyl ester A cold solution of the ethyl ester from part (a) (3.0 g., 6 mmole) and pyridine (1.0 ml.) in dichloromethane (15 ml.) is treated dropwise with ethyl chloroformate (0.84 ml.) and stirred at room temperature for 16 hours. Ether is added and the solution is washed with water, 1N hydrochloric acid, sodium bicarbonate, and brine. The dried solution is evaporated to a yellow solid. Trituration with isopropyl ether gives 2.4 g. of 2-[[(4-methoxyphenyl)methyl]thio]-4-methyl-6-[2-(phenylmethoxy)phenyl]-1,5(6H)-pyrimidinedicarboxylic acid, diethyl ester.

Anal. calc'd. for $C_{32}H_{34}N_2O_6S$: C, 66.87; H, 5.96; N, 4.87; S, 5.57. Found: C, 66.72; H, 5.97; N, 4.55; S, 5.49.

c)
3,6-Dihydro-4-methyl-6-[2-(phenylmethoxy)phenyl]-2-thioxo-1,5(2H)-pyrimidinedicarboxylic acid, diethyl ester A solution of the diethyl ester product from part (b) (1.8 g., 3 mmole), trifluoroacetic acid (1.3 g., 11 mmole), and ethanethiol (0.4 g., 6 mmole) in dichloromethane (25 ml.) is heated at reflux for 32 hours. The cooled solution is diluted with isopropyl ether to crystallize 1.2 g. of yellow solid; m.p. 153°–155°. A solution is made of this material in isopropyl ether (50 ml.) and ethyl acetate (16 ml.) at 50°. Approximately 40 ml. of solvent is boiled off. The cooled solution gives 0.95 g. of 3,6-dihydro-4-methyl-6-[2-(phenylmethoxy)phenyl]-2-thioxo-1,5(2H)-pyrimidinedicarboxylic acid, diethyl ester as yellow crystals; m.p. 155°–157°. TLC (silica gel; ethyl acetate:hexane, 1:1) $R_f$=0.60.

Anal. calc'd. for $C_{24}H_{26}N_2O_5S$: C, 63.41; H, 5.76; N, 6.16; S, 7.05. Found: C, 63.37; H, 5.66; N, 6.12; S, 6.73.

EXAMPLE 63

3,6-Dihydro-4-methyl-6-[3-(trifluoromethyl)phenyl]-2-thioxo-1,5(2H)-pyrimidinedicarboxylic acid, diethyl ester a)
1,4-Dihydro-2-[[(4-methoxyphenyl)methyl]thio]-6-methyl-4-[3-(trifluoromethyl)phenyl]-5-pyrimidinecarboxylic acid, ethyl ester A mixture of 2-[[3-(trifluoromethyl)phenyl]methylene]-3-oxobutanoic acid, ethyl ester (2.0 g., 6.9 mmole), S-(4-methoxybenzyl)thiopseudourea, hydrochloride (1.62 g., 6.9 mmole) and sodium acetate (0.58 g., 6.9 mmole) in dimethylformamide (10 ml.) is heated at 70° for 4 hours. The cooled solution is diluted with ether and washed with water, sodium bicarbonate, and brine. The dried solution is evaporated to give 2.85 g. of an oil. Flash chromatography using ethyl acetate:hexanes gives 1.57 g. of 1,4-dihydro-2-[[(4-methoxyphenyl)methyl]thio]-6-methyl-4-[3-(trifluoromethyl)phenyl]-5-pyrimidinecarboxylic acid, ethyl ester as an oil.

Anal. calc'd for $C_{23}H_{23}N_2F_3O_3S$: C, 59.46; H, 4.99; N, 6.03. Found: C, 59.61; H, 5.38; N, 5.84.

b)
2-[[(4-Methoxyphenyl)methyl]thio]-4-methyl-6-3-(trifluoromethyl)phenyl-1,5i6H]-pyrimidinedicarboxylic acid, diethyl ester A cold solution of the ethyl ester product from part (a) (1.5 g., 3.2 mmole) and pyridine (0.54 ml.) in dichloromethane (15 ml.) is treated dropwise with ethyl chloroformate (0.44 g., 4 mmole). The solution is stirred at room temperature for 16 hours, then diluted with ether and washed with water, 1N hydrochloric acid, sodium bicarbonate, and brine. The dried solution is evaporated to give 1.57 g. of 2-[[(4-methoxyphenyl)methyl]thio]-4- methyl-6-[3-(trifluoromethyl)phenyl]-1,5(6H)-pyrimidinedicarboxylic acid, diethyl ester as an oil.

Anal. calc'd. for $C_{26}H_{27}N_2F_3O_5S$: C, 58.19, H, 5.07; N, 5.22. Found: C, 58.20; H, 5.13; N, 5.20.

c)
3,6-Dihydro-4-methyl-6-[3-(trifluoromethyl)phenyl]-2-thioxo-1,5(2H)-pyrimidinedicarboxylic acid, diethyl ester A solution of the diethyl ester product from part (b) (1.5 g., 2.8 mmole), trifluoroacetic acid (0.82 ml., 10 mmole), and ethanethiol (0.36 g., 5.7 mmole) in dichloromethane (20 ml.) is stirred at room temperature for 24 hours. The solvent is evaporated leaving the residue (1.6 g.) as a semisolid. This material is flash chromatographed using ethyl acetate:hexanes to give 0.82 g. of yellow solid 3,6-dihydro-4-methyl-6-[3-(trifluoromethyl)phenyl]-2-thioxo-1,5(2H)-pyrimidinedicarboxylic acid, diethyl ester; m.p. 98°-100°. TLC (silica gel; ethyl acetate:hexanes, 1:1) $R_f$=0.65.

Anal. calc'd. for $C_{18}H_{19}N_2F_3O_4S$: C, 51.91; H, 4.59; N, 6.72; F, 13.68; S, 7.69. Found: C, 52.07; H, 4.70; N, 6.41; F, 13.35; S, 7.58.

EXAMPLE 64

3,6-Dihydro-4-methyl-6-[2-(methylthio)phenyl]-2-thioxo-1,5(2H)-pyrimidinedicarboxylic acid, diethyl ester a)
1,4-Dihydro-2-[[(4-methoxyphenyl)methyl]thio]-6-methyl-4-[2-(methylthio)phenyl]-5-pyrimidinecarboxylic acid, ethyl ester A mixture of 2-[[2-(methylthio)phenyl]methylene]-3-oxobutanoic acid, ethyl ester (2.0 g., 7.5 mmole), S-(4-methoxybenzyl)thiopseudourea, hydrochloride (1.76 g., 7.5 mmole) and sodium acetate (0.66 g. 8.0 mmole) in dimethylformamide (10 ml.) is stirred and heated at 70° for 6 hours. The cooled mixture is diluted with ether and washed with water, sodium bicarbonate, and brine. The dried solution is evaporated to give 3.0 g. of an oil. Flash chromatography using ethyl acetate:hexanes (1:4) gives 2.13 g. of 1,4-dihydro2-[[( 4-methoxybenzyl)methyl]thio]-6-methyl-4-[2-(methylthio)phenyl]-5-pyrimidinecarboxylic acid, ethyl ester as a yellow oil.

b)
2-[[(4-Methoxyphenyl)methyl]thio]-4-methyl-6-[2-(methylthio)phenyl]-1,5(6H)-pyrimidinedicarboxylic acid, diethyl ester A cold solution of the ethyl ester product from part (a) (2.1 g., 4.7 mmole) and pyridine (0.78 ml., 9 mmole) in dichloromethane (15 ml.) is treated dropwise with ethyl chloroformate (0.63 g., 5.8 mmole) and stirred at room temperature overnight. The solution is then diluted with ether and washed with water, 1N hydrochloric acid, sodium bicarbonate, and brine. The dried solution is evaporated to give 2.1 g. of 2-[[(4-methoxyphenyl)methyl]thio]-4-methyl-6-[2-(methylthio)phenyl]-1,5(6H)-pyrimidinedicarboxylic acid, diethyl ester as an oil which gradually solidifies; m.p. 87°-89°.

Anal. calc'd. for $C_{26}H_{30}N_2O_5S_2$: C, 60.67; H, 5.87; N, 5.44. Found: C, 61.00; H, 5.98; N, 5.17.

c)
3,6-Dihydro-4-methyl-6-[2-(methylthio)phenyl]-2-thioxo-1,5(2H)-pyrimidinedicarboxylic acid, diethyl ester A solution of the diethyl ester product from part (b) (2.1 g., 4 mmole), trifluoroacetic acid (1.18 ml., 13.7 mmole) and ethanethiol (0.52 g., 8 mmole) in dichloromethane (20 ml.) is stirred at room temperature for 16 hours. The mixture is then heated at reflux for 10 hours and the solvent is evaporated to give an oil which gradually solidifies. Trituration with isopropyl ether gives 1.34 g. of yellow solid 3,6-dihydro-4-methyl-6-[2-(methylthio)phenyl]-2-thioxo-1,5(2H)-pyrimidinedicarboxylic acid, diethyl ester; m.p. 148°-150°. TLC(silica gel; ethyl acetate: hexanes, 1:2) $R_f$=0.30.

Anal. calc'd. for $C_{18}H_{22}N_2O_4S_2$: C, 54.79; H, 5.61; N, 7.10; S, 16.25. Found: C, 54.62; H, 5.56; N, 7.01; S, 16.09.

EXAMPLE 65

3,6-Dihydro-4-methyl-6-i3-methoxyphenyl)-2-thioxo-1,5(2H)-pyrimidinedicarboxylic acid, diethyl ester a)
1,4-Dihydro-2-[[(4-methoxyphenyl)methyl]thio]-4-(3-methoxyphenyl)-6-methyl-5-pyrimidinecarboxylic acid, ethyl ester A mixture of 2-[(3-methoxyphenyl)methylene]-3-oxobutanoic acid, ethyl ester (2.0 g., 8 mmole), S-(4-methoxybenzyl)thiopseudourea, hydrochloride (1.87 g., 8 mmole), and sodium acetate (0.67 g., 8 mmole) in dimethylformamide (10 ml.) is stirred at 70° for 4 hours. The cooled mixture is diluted with ether and washed with water, sodium bicarbonate, and brine. The dried solution is evaporated to give 2.85 g. of an impure oil. Flash chromatography using ethyl acetate:hexanes (1:3) gives 2.0 g. of 1,4-dihydro-2-[[(4-methoxyphenyl)methyl]thio]-4-(3-methoxyphenyl)- 6-methyl-5-pyrimidinedicarboxylic acid, ethyl ester as an oil.

b)
2-[[(4-Methoxyphenyl)methyl]thio]-6-(3-methoxyphenyl)-4-methyl-1,5(6H)-pyrimidinedicarboxylic acid, diethyl ester A cold solution of the ethyl ester product from part (a) (2.0 g., 4.7 mmole) and pyridine (0.78 ml., 9 mmole) in dichloromethane (15 ml.) is treated dropwise with ethyl chloroformate (0.64., 5.8 mmole) and stirred at room temperature for 24 hours. The solution is diluted with ether and washed with water, 1N hydrochloric acid, sodium bicarbonate, and brine. The dried solution is evaporated to give 1.95 g. of 2-[[(4-methoxyphenyl)methyl]thio]-6-(3-methoxyphenyl)-4-methyl-1,5(6H)-pyrimidinedicarboxylic acid, diethyl ester as an oil which gradually solidifies; m.p. 79°-81°.

Anal. calc'd. for $C_{26}H_{30}N_2O_6S$: C, 62.62; H, 6.06; N, 5.61. Found: C, 62.55; H, 6.08; N, 5.63.

c)
3,6-Dihydro-4-methyl-6-(3-methoxyphenyl)-2-thioxo-1,5(2H)-pyrimidinedicarboxylic acid, diethyl ester A solution of the diethyl ester product from part (b) (1.95 g., 3.9 mmole), trifluoroacetic acid (1.14 ml., 13.2 mmole) and ethanethiol (0.5 g., 8 mmole) in dichloromethane (20 ml.) is stirred at room temperature for 16 hours. The solvent is evaporated and the oil residue is dissolved in isopropyl ether, then cooled to crystallize 0.8 g. of cream colored 3,6-dihydro-4-methyl-6-(3-methoxyphenyl)-2-thioxo-1,5(2H)-pyrimidinedicarboxylic acid, ethyl ester; m.p. 107°-109°. TLC (silica gel; ethyl acetate:hexanes, 1:2 $R_f$=0.30.

Anal. calc'd. for $C_{18}H_{22}N_2O_5S$: C, 57.12; H, 5.85; N, 7.40; S, 8.47. Found: C, 57.05; H, 5.76; N, 7.46; S, 8.33.

EXAMPLE 66

3,6-Dihydro-4-methyl-6-[3-(phenylmethoxy)phenyl]-2-thioxo-1,5(2H)-pyrimidinedicarboxylic acid, diethyl ester a)
1,4-Dihydro-2-[[(4-methoxyphenyl)methyl]thio]-6-methyl-4-[3-(phenylmethoxy)phenyl]-5-pyrimidinecarboxylic acid, ethyl ester A mixture of 2-[[3-(phenylmethoxy)phenyl]methylene]-3-oxobutanoic acid, ethyl ester (2.0 g., 6.1 mmole), S-(4-methoxybenzyl)thiopseudourea, hydrochloride (1.4 g., 6.1 mmole) and sodium acetate (0.52 g., 6.1 mmole) in dimethylformamide (10 ml.) is stirred and heated at 70° for 6 hours. The cooled mixture is diluted with ether and washed with water, sodium bicarbonate, and brine. The dried solution is evaporated to give 3.0 g. of an oil. Flash chromatography using ethyl acetate:hexanes (1:3) give 1.76 g. of 1,4-dihydro-2-[[(4-methoxyphenyl)methyl]thio]-6-methyl-4-[3-(phenylmethoxy)phenyl]-5-pyrimidinecarboxylic acid, ethyl ester as an oil.

b)
2-[[(4-Methoxyphenyl)methyl]thio]-4-methyl-6-[3-(phenylmethoxy)phenyl]-1,5(6H)-pyrimidinedicarboxylic acid, diethyl ester A cold solution of the ethyl ester product from part (a) (1.76 g., 3.5 mmole) and pyridine (0.58 ml., 7.1 mmole) in dichloromethane (15 ml.) is treated dropwise with ethyl chloroformate (0.48 g., 4.4 mmole) and stirred at room temperature for 24 hours. The solution is then diluted with ether and washed with water, 1N hydrochloric acid, sodium bicarbonate, and brine. The dried solution is evaporated to give 1.76 g. of 2-[[(4-methoxyphenyl)methyl]thio]-4-methyl-6-[3-(phenylmethoxy)phenyl]-1,5(6H)-pyrimidinedicarboxylic acid, diethyl ester as an oil.

Anal. calc'd. for $C_{32}H_{34}N_2O_6S$: C, 66.87; H, 5.96; N, 4.87. Found: C, 66.70; H, 6.17; N, 4.71.

c)
3,6-Dihydro-4-methyl-6-[3-(phenylmethoxy)phenyl]-2-thioxo-1,5(2H)-pyrimidinedicarboxylic acid, diethyl ester A solution of the diethyl ester product from part (b) (1.87 g., 3.2 mmole), trifluoroacetic acid (0.94, 11.4 mmole), ethanethiol (0.49 ml., 3.7 mmole) in dichloromethane (20 ml.) is stirred at room temperature for 16 hours. The solvent is evaporated to give 2.0 g. of an oil. Flash chromatography using ethyl acetate:hexane (1:4) gives 0.95 of yellow solid 3,6-dihydro-4-methyl-6-[3-(phenylmethoxy)phenyl]-2-thioxo-1,5(2H)-pyrimidinedicarboxylic acid, diethyl ester, m.p. 119°–121°. TLC (silica gel; ethyl acetate: hexanes, 1:2) $R_f=0.30$.

Anal. calc'd. for $C_{24}H_{25}N_2O_5S$: C, 63.55; H, 5.55; N, 6.17; S, 7.06. Found: C, 63.23; H, 5.70; N, 6.06; S, 6.82.

EXAMPLE 67

3,6-Dihydro-4-methyl-6-(3-chlorophenyl)-2-thioxo-1,5(2H)-pyrimidinedicarboxylic acid, diethyl ester a)
1,4-Dihydro-6-methyl-4-(3-chlorophenyl)-2-[[(4-methoxyphenyl)methyl]thio]-5-pyrimidinecarboxylic acid, ethyl ester A mixture of 2-[(3-chlorophenyl)methylene]-3-oxobutanoic acid, ethyl ester (2.0 g., 7.9 mmole), S-(4-methoxyphenyl)thiopseudourea, hydrochloride (1.84 g., 7.9 mmole), and sodium acetate (0.66 g., 7.9 mmole) in dimethylformamide (10 ml.) is heated at 70° for 6 hours. After cooling, ether is added followed by washing with water, sodium bicarbonate, and brine. The dried solution is evaporated to give 3.1 g. of an oil. Flash chromatography using ethyl acetate:hexanes (1:4) gives 2.0 g. of 1,4-dihydro-6-methyl-4-(3-chlorophenyl)-2-[[(4-methoxyphenyl)methyl]thio]-5-pyrimidinecarboxylic acid, ethyl ester as a yellow oil.

Anal. calc'd. for $C_{22}H_{23}N_2O_3ClS$: C, 61.45; H, 5.15; N, 6.51. Found: C, 61.18; H, 5.43; N, 6.34.

b)
2-[[(4-Methoxyphenyl)methyl]thio]-4-methyl-6-(3-chlorophenyl)-1,5(6H)-pyrimidinedicarboxylic acid, diethyl ester A cold solution of the ethyl ester product from part (a) (2.0 g., 4.6 mmole) and pyridine (0.76 ml., 9.3 mmole) in dichloromethane (15 ml.) is treated dropwise with ethyl chloroformate (0.48 g., 4.4 mmole) and stirred at room temperature for 24 hours. The solution is diluted with ether and washed with water, 1N hydrochloric acid, sodium bicarbonate, and brine. The dried solution is evaporated to give 1.87 g. of 2-[[(4-methoxyphenyl)methyl]thio]-6-(3-chlorophenyl)-1,5(6H)-pyrimidinedicarboxylic acid, diethyl ester as an oil.

Anal. calc'd. for $C_{25}H_{27}N_2O_5ClS$: C, 66.87; H, 5.96; N, 4.87. Found: C, 66.70; H. 6.17; N, 4.71.

c)
3,6-Dihydro-4-methyl-6-(3-chlorophenyl)-2-thioxo-1,5(2H)-pyrimidinedicarboxylic acid, diethyl ester A solution of the diethyl ester product from part (b) (2.1 g., 4.1 mmole), trifluoroacetic acid (1.2 ml., 14.5 mmole), and ethanethiol (0.52 g., 16 mmole) in dichloromethane (20 ml.) is stirred at room temperature for 16 hours. The solvent is evaporated and the oil residue is dissolved in isopropyl ether (20 ml.), then cooled in an ice bath to crystallize 1.0 g. of cream colored 3,6-dihydro-4-methyl-6-(3-chlorophenyl)-2-thioxo-1,5(2H)-pyrimidinedicarboxylic acid, diethyl ester; m.p. 95°–97°. TLC (silica gel; ethyl acetate: hexanes, 1:2) $R_f=0.40$.

Anal. calc'd. for $C_{17}H_{19}N_2ClO_4S$: C, 53.32; H, 5.00; N, 7.31; Cl, 9.25; S, 8.37. Found: C, 53.34; H, 5.01; N, 7.23; Cl, 9.19; S, 8.09.

EXAMPLE 68

3,6-Dihydro-6-(3-cyanophenyl)-4-methyl-2-thioxo-1,5(2H)-pyrimidinedicarboxylic acid, diethyl ester a)

1,4-Dihydro-2-[[-(4-methoxyphenyl)methyl]thio]-6-methyl-4-(3-cyanophenyl)-5-pyrimidinecarboxylic acid, ethyl ester A mixture of 2-[(3-cyanophenyl)methylene]-3-oxobutanoic acid, ethyl ester (2.6 g., 10.7 mmole), S-(4-methoxybenzyl)thiopseudourea, hydrochloride (2.5 g., 10.7 mmole), and sodium acetate (0.84 g., 10.7 mmole) in dimethylformamide (12 ml.) is stirred and heated at 70° for 6 hours. The cooled mixture is diluted with ether and washed with water, sodium bicarbonate, and brine. The dried solution is evaporated to give 4.2 g. of an oil. Flash chromatography using ethyl acetate:hexanes (1:2) gives 2.0 g. of an oil. Trituration with isopropyl ether gives 1.6 g. of cream colored solid 1,4-dihydro-2-[[(4-methoxyphenyl)methyl]thio]-6-methyl-4-(3-cyanophenyl)-5-pyrimidinecarboxylic acid, ethyl ester; m.p. 124°–126°. TLC (silica gel; ethyl acetate: hexane, 1:1) $R_f$=0.55.

Anal. calc'd for $C_{23}H_{23}N_3O_3S$: C, 65.53; H, 5.49; N, 9.96; S, 7.60. Found: C, 65.62; H, 5.52; N, 9.82; S, 7.60.

b)

2-[[(4-Methoxyphenyl)methyl]thio]-4-methyl-6-(3-cyanophenyl)-1,5(6H)-pyrimidinedicarboxylic acid, diethyl ester A cold solution of the ethyl ester product from part (a) (1.25 g., 2.9 mmole) and pyridine (0.5 ml., 6.0 mmole) in dichloromethane (15 ml.) is treated dropwise with ethyl chloroformate (0.39 g., 3.6 mmole) and stirred at room temperature for 4 hours. Ether is added and the solution is washed with water, 1N hydrochloric acid, sodium bicarbonate, and brine. The dried solution is evaporated to give 1.45 g. of 2-[[(4-methoxyphenyl)methyl]thio]-4-methyl-6-(3-cyanophenyl)-1,5(6H)-pyrimidinedicarboxylic acid, diethyl ester as an oil which slowly solidifies; m.p. 85°–87°.

Anal. calc'd. for $C_{26}H_{27}N_3O_5S$: C, 63.26; H, 5.51; N, 8.51. Found: C, 63.25; H, 5.54; N, 8.57.

c)

3,6-Dihydro-6-(3-cyanophenyl)-4-methyl-2-thioxo-1,5(2H)-pyrimidinedicarboxylic acid, diethyl ester A solution of the diethyl ester product from part (b) (1.4 g., 2.8 mmole), trifluoroacetic acid (0.9 ml., 10 mmole), and ethanethiol (0.39 g., 6.2 mmole) in dichloromethane (15 ml.) is stirred at room temperature for 16 hours. The solvent is evaporated and the oil residue is dissolved in isopropyl ether, then quickly filtered to remove a small amount of insoluble material. The filtrate gives 0.74 g. of yellow solid 3,6-dihydro-6-(3-cyanophenyl)-4-methyl-2-thioxo-1,5(2H)-pyrimidinedicarboxylic acid, diethyl ester; m.p. 155°–156°. TLC (silica gel; ethyl acetate:hexanes, 1:1) $R_f$=0.45.

Anal. calc'd. for $C_{18}H_{19}N_3O_4S$: C, 57.89; H, 5.12; N, 11.25; S, 8.58. Found C, 58.14; H, 5.23; N, 11.10; S, 8.44.

EXAMPLE 69

3,6-Dihydro-4-methyl-6-(3-methylphenyl)-2-thioxo-1,5(2H)-pyrimidinedicarboxylic acid, diethyl ester a)

1,4-Dihydro-2-[[(4-methoxyphenyl)methyl]thio]-6-methyl-4-(3-methylphenyl)-5-pyrimidinecarboxylic acid, ethyl ester A mixture of S-(4-methoxybenzyl)thiopseudourea, hydrochloride (2.5 g., 10.7 mmole), 2-[(3-methylphenyl)methylene]-3-oxobutanoic acid, ethyl ester (2.5 g., 10.7 mmole] and sodium acetate (0.84 g., 10.7 mmole) in dimethylformamide (12 ml.) is stirred and heated at 70° for 6 hours. After cooling, ether is added followed by water, sodium bicarbonate, and brine. The dried solution is evaporated to give 4.4 g. of an impure oily product. Flash chromatography using ethyl acetate: hexane (1:4) gives 2.5 g. of 1,4-dihydro-2-[[(4-methoxyphenyl)methyl]thio]-6-methyl-4-(3-methylphenyl)-5-pyrimidinecarboxylic acid, ethyl ester as an oil which slowly solidifies; m.p. 65°–67°.

Anal. calc'd. for $C_{23}H_{26}N_2O_3S$: C, 67.28; H, 6.38; N, 6.82. Found: C, 67.44; H, 6.52; N, 6.72.

b)

2-[[i4-Methoxyphenyl)methyl]thio]-4-methyl-6-(3-methylphenyl)-1,5(6H)-pyrimidinedicarboxylic acid, diethyl ester A cold solution of the ethyl ester product from part (a) (2.0 g., 4.8 mmole) and pyridine (0.8 ml., 9.6 mmole) in dichloromethane (15 ml.) is treated dropwise with ethyl chloroformate (0.6 g., 5.9 mmole) and stirred at room temperature for 4 hours. Ether is added followed by washing with water, 1N hydrochloric acid, sodium bicarbonate, and brine. The dried solution is evaporated to give 1.7 g. of yellow solid 2-[[(4-methoxyphenyl)methyl]thio]-4-methyl-6-(3-methyl-phenyl)-1,5(6H)-pyrimidinedicarboxylic acid, diethyl ester. m.p. 100°–102°.

Anal. calc'd. for $C_{26}H_{30}N_2O_5S$: C, 64.70; H, 6.26; N, 5.80. Found: C, 64.97; H, 6.59; N, 5.45.

c)

3,6-Dihydro-4-methyl-6-(3-methylphenyl)-2-thioxo-1,5(2H)-pyrimidinedicarboxylic acid, diethyl ester A solution of the diethyl ester product from part (b) (1.6 g., 3.3 mmole), trifluoroacetic acid (0.99 ml., 11 mmole), and ethanethiol (0.43 g., 6.8 mmole) in dichloromethane (15 ml.) is stirred at room temperature for 48 hours. The solvent is evaporated and the oil residue is dissolved in isopropyl ether to crystallize 0.77 g. of yellow solid 3,6-dihydro-4-methyl-6-(3-methylphenyl)-2-thioxo-1,5(2H)-pyrimidinedicarboxylic acid, diethyl ester; m.p. 93°–95°. TLC (silica gel; ethyl acetate:hexane, 1:1) $R_f$=0.55.

Anal. calc'd. for $C_{18}H_{22}N_2O_4S$: C, 59.64; H, 6.11; N, 7.73; S, 8.84. Found: C, 59.57; H, 6.00; N, 7.62; S, 8.60.

EXAMPLE 70

3,6-Dihydro-4-methyl-6-(2-methylphenyl)-2-thioxo-1,5(2H)-pyrimidinedicarboxylic acid, diethyl ester a)
1,4-Dihydro-2-[[(4-methoxyphenyl)methyl]thio]-6-methyl-4-(2-methylphenyl)-5-pyrimidinedicarboxylic acid, ethyl ester A mixture of 2-[(2-methylphenyl)methylene]-3-oxobutanoic acid, ethyl ester (6.0 g., 25.8 mmole), S-(4-methoxybenzyl)thiopseudourea, hydrochloride (6.0 g., 25.8 mmole) and sodium acetate (2.12 g., 25.8 mmole) in dimethylformamide (50 ml.) is stirred and heated at 70° for 4 hours. The cooled mixture is diluted with ether and washed with water, sodium bicarbonate, and brine. The dried solution is evaporated to give 9.6 g. of 1,4-dihydro-2-[[(4-methoxyphenyl)methyl]thio]-6-methyl-4-(2-methylphenyl)-5-pyrimidinecarboxylic acid, ethyl ester as an oil.

b)
2-[[(4-methoxyphenyl)methyl]thio]-4-methyl-6-(2-methylphenyl)-1,5(6H)-pyrimidinedicarboxylic acid, diethyl ester A cold solution of the ethyl ester product from part (a) (2.0 g., 4.9 mmole) and pyridine (0.8 ml., 10.4 mmole) in dichloromethane (20 ml.) is treated dropwise with a solution of ethyl chloroformate (0.64 g., 5.8 mmole) in dichloromethane (3 ml.) and stirred for 4 hours at room temperature. Dichloromethane is added and the solution is washed with water, 1N hydrochloric acid, sodium bicarbonate, and brine. The dried solution is evaporated to an oil which slowly solidifies. Trituration with ether gives 1.25 g. of cream colored solid 2-[[(4-methoxyphenyl)methyl]thio]-4-methyl-6-(2-methylphenyl)-1,5(6H)-pyrimidinedicarboxylic acid, diethyl ester; m.p. 118°-120°.

Anal. calc'd. for $C_{26}H_{30}N_2O_5S$: C, 64.70; H, 6.26; N, 5.80. Found: C, 64.80; H, 6.28; N, 6.09.

c)
3,6-Dihydro-4-methyl-6-(2-methylphenyl)-2-thioxo-1,5(2H)-pyrimidinedicarboxylic, acid diethyl ester A solution of the diethyl ester product from part (b) (1.25 g., 2.6 mmole), trifluoroacetic acid (1.0 ml., 12.9 mmole) and ethanethiol (0.39 g., 6 mmole) in dichloromethane (20 ml.) is stirred at room temperature for 48 hours. The solvent is evaporated and the oil residue is dissolved in isopropyl ether (10 ml.) to slowly crystallize 0.57 g. of cream colored solid 3,6-dihydro-4-methyl-6-(2-methylphenyl)-2-thioxo-1,5(2H)-pyrimidinedicarboxylic acid, diethyl ester; m.p. 112°-114°. TLC (silica gel; ethyl acetate: hexane, 1:1) $R_f=0.55$.

Anal. calc'd. for $C_{18}H_{22}N_2O_4S$: C, 59.64; H, 6.11; N, 7.73; S, 8.84. Found: C, 59.45; H, 6.17; N, 7.66; S, 8.85.

EXAMPLE 71

3,6-Dihydro-4-methyl-6-(3-nitrophenyl)-2-thioxo-1,5(2H)-pyrimidinedicarboxylic acid, 1-ethyl-5-methyl ester a)
1,4-Dihydro-2-[[(4-methoxyphenyl)methyl]thio]-6-methyl-4-(3-nitrophenyl)-5-pyrimidinecarboxylic acid, methyl ester A solution of 2-[(3-nitrophenyl)methylene]-3-oxobutanoic acid, methyl ester (5.0 g., 0.02 mole) in dimethylformamide (20 ml.) under argon at room temperature is treated with S-(4-methoxybenzyl)thiopseudourea hydrochloride (4.65 g., 0.02 mole) in one portion. The mixture is then heated at 65° for 3 hours. Upon cooling, the mixture is diluted with ethyl acetate and washed with water (twice), aqueous sodium bicarbonate, and saturated brine. The aqueous fractions are back-extracted with fresh ethyl acetate. The combined organic fractions are dried (magnesium sulfate) and concentrated in vacuo to give 9.0 g. of crude product. Crystallization from acetone/isopropyl ether gives 6.8 g. of 1,4-dihydro-2-[[(4-methoxyphenyl)methyl]thio]-6-methyl-4-(3-nitrophenyl)-5-pyrimidinecarboxylic acid, methyl ester; m.p. 125°-127.5°. TLC (silica gel; ethyl acetate:hexanes, 1:1) $R_f=0.48$.

Anal. calc'd. for $C_{21}H_{21}N_3O_5S$: C, 59.00; H, 4.95; N, 9.83; S, 7.50. Found: C, 58.86; H, 4.82; N, 9.51; S, 7.25.

b)
2-[[(4-Methoxyphenyl)methyl]thio]-4-methyl-6-(3-nitrophenyl)-1,5(6H)-pyrimidinedicarboxylic acid, 1-ethyl 5-methyl ester A solution of the methyl ester from part (a) (1.0 g., 2.4 mmole) in dichloromethane (10 ml.) under argon at 0°-5° is treated with pyridine (0.6 ml., 7.6 mmole) and ethyl chloroformate (0.44 ml., 4.6 mmole). The reaction mixture is then stirred at room temperature for 4 hours. The mixture is diluted with ether and washed with water, 1N hydrochloric acid, and water (ether solution is filtered to remove a small amount of insolubles) and then washed with aqueous sodium bicarbonate, water and saturated brine. The organic fraction is dried over anhydrous magnesium sulfate and concentrated in vacuo to give 1.58 g. of crude product. Flash chromatography eluting with ethyl acetate:hexane (1:4) gives 740 mg. of the desired product. Trituration with hexane:isopropyl ether gives 590 mg. of 2-[[(4-methoxyphenyl)methyl]thio]-4-methyl-6-(3-nitrophenyl)-1,5(6H)-pyrimidinedicarboxylic acid, 1-ethyl 5-methyl ester; m.p. 99°-104°. TLC (silica gel; ethyl acetate:hexanes) $R_f=0.54$.

Anal. calc'd. for $C_{24}H_{25}N_3O_6S$: C, 57.70; H, 5.04; N, 8.41; S, 6.42. Found: C, 57.84; H, 5.12; N, 8.43; S, 6.38.

c)
3,6-Dihydro-4-methyl-6-(3-nitrophenyl)-2-thioxo-1,5(2H)-pyrimidinedicarboxylic acid, 1-ethyl 5-methyl ester A solution of the diethyl ester product from part (b) (580 mg., 1.16 mmole) in dichloromethane (8 ml.) under argon at room temperature is treated with trifluoroacetic acid (0.3 ml., 0.42 g., 3.8 mmole) and ethanethiol (0.2 ml., 0.16 g., 2.7 mmole) overnight. The volatiles are removed in vacuo and the residue is triturated with isopropyl ether/hexane to give 430 mg. of yellow powder. Crystallization from chloroform/acetone/isopropyl ether gives 380 mg. of 3,6-dihydro-4-methyl-6-(3-nitrophenyl)-2-thioxo-1,5(2H)-pyrimidinedicarboxylic acid, 1-ethyl 5-methyl ester as a light yellow powder; m.p. 163°-165°. TLC (silica gel; ethyl acetate:hexane, 1:1) $R_f=0.45$.

Anal. calc'd. for $C_{16}H_{17}N_3O_6S$: C, 50.65; H, 4.52; N, 11.08; S, 8.45. Found: C, 50.72; H, 4.53; N, 10.86; S, 8.18.

EXAMPLE 72

3,6-Dihydro-4-methyl-6-(3-nitrophenyl)-2-thioxo-1,5(2H)-pyrimidinedicarboxylic acid, 5-ethyl 1-methyl ester a)

1,4-Dihydro-2-[[(4-methoxyphenyl)methyl]thio]-6-methyl-4-(3-nitrophenyl)-5-pyrimidine-carboxylic acid, ethyl ester A mixture of 2-[(3-nitrophenyl)methylene]-3-oxobutanoic acid, ethyl ester (13.58 g., 51 mmole), S-(4-methoxybenzyl)thiopseudourea, hydrochloride (12.0 g., 51 mmole), and sodium acetate (4.18 g., 51 mmole) in dimethylformamide (90 ml.) is stirred and heated at 70° for 4 hours. After cooling, ether is added followed by washing with water, sodium bicarbonate and brine. The dried solution is evaporated to give an oil which is treated with isopropyl ether to give 18.8 g. of cream colored solid 1,4-dihydro-2-[[(4-methoxyphenyl)methyl]-thio]-6-methyl-4-(3-nitrophenyl)-5-pyrimidinecarboxylic acid, ethyl ester; m.p. 95°–97°. TLC (silica gel; ethyl acetate:hexane, 1:1) $R_f$=0.50.

Anal. calc'd. for $C_{22}H_{23}N_3O_5S$: C, 59.84; H, 5.25; N, 9.51; S, 7.26 Found: C, 59.90; H, 5.26; N, 9.58; S, 7.34.

b)

2-[[(4-Methoxyphenyl)methyl]thio]-4-methyl-6-(3-nitrophenyl)-1,5(6H)-pyrimidinedicarboxylic acid, 5-ethyl 1-methyl ester A solution of the ethyl ester product from part (a) (1.0 g., 2.27 mmole) in dichloromethane (6 ml.) and pyridine (0.5 ml.) is cooled to 0° under argon and treated dropwise with methyl chloroformate (0.26 ml., 3.37 mmole). After the addition is completed, the cooling bath is removed and the reaction is stirred at room temperature for 1 hour. The yellow reaction solution is diluted with ethyl acetate and washed with water, 0.5N hydrochloric acid, sodium bicarbonate, and brine. After drying over anhydrous magnesium sulfate, the solvent is stripped to give 1.10 g. of 2-[[(4-methoxyphenyl)methyl]thio]-4-methyl-6-(3-nitrophenyl)-1,5(6H)-pyrimidinedicarboxylic acid, 5-ethyl 1-methyl ester as a yellow thick oil.

c)

3,6-Dihydro-4-methyl-6-(3-nitrophenyl)-2-thioxo-1,5(2H)-pyrimidinedicarboxylic acid, 5-ethyl 1-methyl ester The ester product from part (b) (1.10 g.) is dissolved in dichloromethane (5 ml.) and treated with trifluoroacetic acid (1.0 ml.) and ethanethiol (0.5 ml.). The reaction is stirred at room temperature overnight and the solvent is evaporated. The residue is coevaporated with toluene twice and the product is crystallized from dichloromethane-isopropyl ether to give 750 mg. of yellow solid 3,6-dihydro-4-methyl-6-(3-nitrophenyl)-2-thioxo-1,5(2H)-pyrimidinedicarboxylic acid, 5-ethyl 1-methyl ester; m.p. 149.5°–151°. TLC (silica gel; ethyl acetate:hexanes, 40:60) $R_f$=0.35.

Anal. calc'd. for $C_{16}H_{17}N_3O_6S$: C, 50.65; H, 4.52; N, 11.08; S, 8.45. Found: C, 50.63; H, 4.44; N, 11.04; S, 8.21.

EXAMPLE 73

3,6-Dihydro-4-methyl-6-(3-nitrophenyl)-2-thioxo-1,5(2H)-pyrimidinedicarboxylic acid, 1-(1-methylethyl) 5-methyl ester a)

2-[[(4-Methoxyphenyl)methyl]thio]-4-methyl-6-(3-nitrophenyl)-1,5(6H)-pyrimidinedicarboxylic acid, 1-(1-methylethyl) 5-methyl ester 1,4-Dihydro-2-[[(4-methoxyphenyl)methyl]thio]-6-methyl-4-(3-nitrophenyl)-5-pyrimidinecarboxylic acid, methyl ester (4.2 g., 9.8 mmole) is dissolved in dry dichloromethane (20 ml.) at 0° under nitrogen. Bis(trimethylsilyl)trifluoroacetamide (1.1 eq., 2.87 ml., 10.8 mmole) is added dropwise. After 30 minutes, a precipitate forms in the reaction mixture. Pyridine (1.1 eq., 0.87 ml., 10.8 mmole) is added followed by the dropwise addition of isopropyl chloroformate (1.1 eq., 1.23 ml., 10.8 mmole) in dichloromethane (5 ml.). The cooling bath is removed and the mixture is stirred to room temperature. After 1 hour, the precipitate is in solution. The reaction mixture is poured into ethyl acetate (20 ml.) and washed with sodium bicarbonate (10 ml.), sodium dihydrogen phosphate (15 ml.), and brine. The mixture is dried over anhydrous magnesium sulfate, filtered, and evaporated to give 6.51 g. of 2-[[(4-methoxyphenyl)methyl]thio]-4-methyl-6-(3-nitrophenyl)-1,5(6H)-pyrimidinedicarboxylic acid, 1-(1-methylethyl) 5-methyl ester as an orange oil.

b)

3,6-Dihydro-4-methyl-6-(3-nitrophenyl)-2-thioxo-1,5(2H)-pyrimidinedicarboxylic acid, 1-(1-methylethyl) 5-methyl ester The ester product from part (a) (6.51 g.) is dissolved in dichloromethane (40 ml.) and treated with trifluoroacetic acid (4.0 ml.) and ethanethiol (1.45 ml., 19.6 mmole). The mixture is stirred overnight at room temperature. The reaction mixture is diluted with dichloromethane (20 ml.) and washed with water (2×40 ml.), sodium bicarbonate (2×40 ml.), and sodium dihydrogen phosphate (2×40 ml.). The organic layer is dried over anhydrous magnesium sulfate, filtered, and stripped to give 5.28 g. of a yelow solid. This solid product is recrystallized from aqueous acetonitrile to give 2.62 g. of pale yellow solid 3,6-dihydro-4-methyl-6-(3-nitrophenyl)-2-thioxo-1,5(2H)-pyrimidinedicarboxylic acid, 1-(1-methylethyl) 5-methyl ester; m.p. 197°–199°. TLC (silica gel; ethyl acetate:hexanes, 1:2) $R_f$=0.4.

Anal. calc'd. for $C_{17}H_{19}N_3O_6S$: C, 51.90; H, 4.87; N, 10.68; S, 8.15. Found: C, 52.01; H, 4.89; N, 10.68; S, 8.21.

EXAMPLE 74

3,6-Dihydro-4-methyl-6-(3-nitrophenyl)-2-thioxo-1,5(2H)-pyrimidinedicarboxylic acid, dimethyl ester a)

2-[[(4-Methoxyphenyl)methyl]thio]-4-methyl-6-(3-nitrophenyl)-1,5(6H)-pyrimidinedicarboxylic acid, dimethyl ester Bis(trimethylsilyl)trifluoroacetamide (2.87 ml., 10.8 mmole) is added to a solution of 1,4-dihydro-2-[[(4-methoxyphenyl)methyl]thio]-6-methyl-4-(3-nitrophenyl)-5-pyrimidinecarboxylic acid, methyl ester (4.19 g., 9.8 mmole) in dry dichloromethane (20 ml.) at 0°.

After 30 minutes, methyl chloroformate (0.83 ml., 10.8 mmole) in dichloromethane (3 ml.) is added dropwise followed by the addition of pyridine (0.87 ml., 10.8 mmole). The ice bath is removed and the reaction is allowed to stir for 2 hours. The reaction is diluted with ethyl acetate (20 ml.) and washed with saturated sodium bicarbonate, sodium dihydrogen phosphate, and saturated sodium chloride. The organic layer is dried over anhydrous magnesium sulfate, filtered and stripped in vacuo to give 5.3 g. of 2-[[(4-methoxyphenyl)methyl]thio-4-methyl-6-(3-nitrophenyl)-1,5(6H)-pyrimidinedicarboxylic acid, dimethyl ester as a pale green gum.

b)

3,6-Dihydro-4-methyl-6-(3-nitrophenyl)-2-thioxo-1,5(2H)-pyrimidinedicarboxylic acid, dimethyl ester The dimethyl ester product from part (a) (5.3 g.) is dissolved in dichloromethane (45 ml.) at room temperature and treated with trifluoroacetic acid (4.5 ml.) and ethanethiol (1.7 ml.). The reaction mixture is stirred for 18 hours and then poured into dichloromethane (20 ml.) and washed with water (2×50 ml.), saturated sodium bicarbonate (50 ml.), and sodium dihydrogen phosphate (50 ml.), dried over magnesium sulfate, filtered, and stripped in vacuo to give 4.06 g. of yellow solid. Recrystallization from hexane/ether/isopropyl alcohol gives 2.5 g. of a yellow solid. A second recrystallization from ethanol/water gives 3,6-dihydro-4-methyl-6-(3-nitrophenyl)-2-thioxo-1,5(2H)-pyrimidinedicarboxylic acid, dimethyl ester as a yellow solid; m.p. 171.5°–173°. TLC(silica gel; ethyl acetate:hexanes, 1:2) $R_f$=0.29.

Anal. calc'd. for $C_{15}H_{15}N_3O_6S$: C, 49.31; H, 4.14; N, 11.50; S, 8.77. Found: C, 49.30; H, 4.11; N, 11.48; S, 8.55.

EXAMPLE 75

3,6-Dihydro-4-methyl-6-(3-nitrophenyl)-2-thioxo-1,5(2H)-pyrimidinedicarboxylic acid, 5-ethyl 1-(1-methylethyl) ester a)

2-[(4-Methoxyphenyl)methyl]thio-4-methyl-3-(3-nitrophenyl)-1,5(6H)-pyrimidinedicarboxylic acid 5-ethyl 1-(1-methylethyl) ester A solution of 1,4-dihydro-2-[[(4-methoxyphenyl)methyl]thio]-6-methyl-4-(3-nitrophenyl)-5-pyrimidinecarboxylic acid, ethyl ester (2.0 g., 4.5 mmole) in dichloromethane (20 ml.) containing pyridine (0.71 g., 9.1 mmole) is cooled to −10° and treated dropwise with a solution of isopropyl chloroformate (0.66 g., 5.4 mmole) in dichloromethane (3 ml.). After stirring at room temperature for 16 hours, dichloromethane is added and the solution is washed with water, 1N hydrochloric acid, sodium bicarbonate, and brine. The dried solution is evaporated to give 2.6 g. of an oil. Flash chromatography using dichloromethane gives 2.3 g. of 2-[[(4-methoxyphenyl)methyl]thio]-4-methyl-6-(3-nitrophenyl)-1,5(6H)-pyrimidinedicarboxylic acid, 5-ethyl 1-(1-methylethyl) ester as an oil.

b)

3,6-Dihydro-4-methyl-6-(3-nitrophenyl)-2-thioxo-1,5(2H)-pyrimidinedicarboxylic acid, 5-ethyl 1-(1-methylethyl) ester A solution of the ester product from part (a) (2.2 g., 4.1 mmole) in dichloromethane (25 ml.) is treated with trifluoroacetic acid (1.5 ml., 19.5 mmole) and ethanethiol (0.61 g., 9.5 mmole). After stirring at room temperature overnight, the solvent is evaporated and the residue is dissolved in isopropyl ether to crystallize 1.16 g. of cream colored 3,6-dihydro-4-methyl-6-(3-nitrophenyl)-2-thioxo-1,5(2H)-pyrimidinedicarboxylic acid, 5-ethyl 1(1-methyl-ethyl) ester; m.p. 150°–152°. TLC (silica gel; ethyl acetate:hexanes, 1:2) $R_f$=0.30.

Anal. calc'd for $C_{18}H_{21}N_3O_6S$: C, 53.06; H, 5.19; N, 10.31; S, 7.86. Found: C, 53.13; H, 5.25; N, 10.15; S, 7.92.

EXAMPLE 76

3,6-Dihydro-4-methyl-6-(3-nitrophenyl)-2-thioxo-1,5(2H)-pyrimidinedicarboxylic acid, 1-methyl 5-(1-methylethyl) ester a)

1,4-Dihydro-2-[[(4-methoxyphenyl)methyl]-thio]-6-methyl-4-(3-nitrophenyl)-5-pyrimidinecarboxylic acid, 1-methylethyl ester, monohydrochloride 2-[(3-Nitrophenyl)methylene]-3-oxobutanoic acid, 1-methylethyl ester (20 g., 72.4 mmole) and S-(4-methoxybenzyl)thiopseudourea, hydrochloride (16.8 g., 72.4 mmole) are combined in dimethylformamide (70 ml.). Sodium acetate (5.9 g., 72.4 mmole) is added and the mixture is heated at 60° for 16 hours. The mixture is diluted with ether and filtered, washed with water (2×100 ml.), saturated sodium bicarbonate (2×100 ml.), and saturated sodium chloride, dried over anhydrous magnesium sulfate, filtered and stripped in vacuo to give an oil. This product is taken up in ether (200 ml.) and treated dropwise with methanol hydrochloric acid (1 eq.). The white salt is collected by filtration, washed thoroughly with ether, and dried to give 33.99 g. of 1,4-dihydro-2-[[(4-methoxyphenyl)methyl]thio]-6-methyl-4-(3-nitrophenyl)-5-pyrimidinecarboxylic acid, 1-methylethyl ester, monohydrochloride.

b)

2-[(4-Methoxyphenyl)methyl]thio]-4-methyl-6-(3-nitrophenyl)-1,5 6H)-pyrimidinedicarboxylic acid, 5-(1-methylethyl 1-methyl ester The free base of the ester product from part (a) (5.27 g., 11.6 mmole) is dissolved in dichloromethane (25 ml.) and cooled to 0° under argon. Bis(trimethylsilyl)trifluoroacetamide (3.38 ml., 12.8 mmole) is added and the reaction is stirred for 30 minutes at 0°. Pyridine (1.03 ml., 12.8 mmole) is then added, followed by the dropwise addition of methyl chloroformate (10 ml., 12.8 mmole) in dichloromethane (15 ml.). The reaction mixture is stirred for one hour at 0° and then the ice bath is removed. After stirring for 3 hours at room temperature, ethyl acetate (75 ml.) is added and the reaction is washed with sodium bicarbonate (2×150 ml.), sodium dihydrogen phosphate (2×150 ml.), and saturated sodium chloride (2×100 ml.), dried over magnesium sulfate, and stripped in vacuo to give 7.52 g. of 2-[[(4-methoxyphenyl)methyl]thio]-4-methyl-6-(3-nitrophenyl)-1,5(6H)-pyrimidinedicarboxylic acid, 5-(1-methylethyl 1-methyl ester.

c)

3,6-Dihydro-4-methyl-6-(3-nitrophenyl)-2-thioxo-1,5(2H)-pyrimidinedicarboxylic acid, 5-(1-methylethyl 1-methyl ester The ester product from part (b) (7.42 g.) is dissolved in dichloromethane (50 ml.) and treated with trifluoroacetic acid (5 ml.) and ethanethiol (1.5 ml.). The reaction is stirred at room temperature for 16 hours, and then dichloromethane (50 ml.) is added. The organic layer is washed with water (2×150 ml.), saturated sodium bicarbonate (2×150 ml.), saturated sodium carbonate (100 ml.), sodium dihydrogen phosphate (100 ml.), and saturated sodium chloride (100 ml.), dreid over magnesium sulfate, and evaporated in vacuo to give 6.31 g. of product as an oil. Crystallization from ethyl acetate: hexanes gives 3.2 g. of yellow solid 3,6-dihydro-4-methyl-6-(3-nitrophenyl)-2-thioxo-1,5(2H)-pyrimidinedicarboxylic acid, 5-(1-methylethyl 1-methyl ester; m.p. 130.5°–131.5°. TLC (silica gel; ethyl acetate:-hexanes, 1:2) $R_f$=0.30.

Anal. calc'd. for $C_{17}H_{19}N_3O_6S$: C, 51.90; H, 4.83; N, 10.68; S, 8.15. Found: C, 51.91; H, 4.94; N, 10.52; S, 8.08.

EXAMPLE 77

3,6-Dihydro-4-methyl-6-(3-nitrophenyl)-2-thioxo-1,5(2H)-pyrimidinedicarboxylic acid, 1-ethyl 5-(1-methylethyl) ester a)

2-[[(4-M-ethoxyphenyl)methyl]thio]-4-methyl-6-(3-nitrophenyl)-1,5(6H]-pyrimidinedicarboxylic acid, 1-ethyl 5-(1-methylethyl)ester 1,4-Dihydro-2-[[(4-methoxyphenyl)methyl]thio]-6-methyl-4-(3-nitrophenyl)-5-pyrimidinecarboxylic acid, 1-methylethyl ester (5.35 g., 11.7 mmole) is dissolved in dichloromethane (25 ml.) and cooled to 0° under argon. Bis(trimethylsilyl)trifluoroacetamide (3.43 ml., 12.9 mmole) is added and the reaction is stirred for 30 minutes at 0°. Pyridine (1.04 ml., 12.9 mmole) is then added followed by the dropwise addition of ethyl chloroformate (1.24 ml., 12.9 mmole) as a solution in dichloromethane (5 ml.). The reaction is stirred for one hour at 0° and then the ice bath is removed. After stirring for 3 hours at room temperature, ethyl acetate (75 ml.) is added and the reaction is washed with sodium bicarbonate (2×150 ml.), sodium dihydrogen phosphate (2×150 ml.), and saturated sodium chloride (2×100 ml.), dried over anhydrous magnesium sulfate, and stripped in vacuo to give 8.23 g. of 2-[[(4-methoxyphenyl)methyl]-thio]-4-methyl-6-(3-nitrophenyl)-1,5(6H)-pyrimidinedicarboxylic acid, 1-ethyl 5-(1-methylethyl)ester as an oil.

b)

3,6-Dihydro-4-methyl-6-(3-nitrophenyl)-2-thioxo-1,5(2H)-pyrimidinedicarboxylic acid, 1-ethyl 5-(1-methylethyl)ester The ester product from part (a) (8.23 g.) is dissolved in dichloromethane (50 ml.) and treated with trifluoroacetic acid (5 ml.) and ethanethiol (1.5 ml.). The reaction is stirred at room temperature for 16 hours and then dichloromethane (50 ml.) is added. The organic layer is washed with water (2×150 ml.), saturated sodium bicarbonate (2×150 ml.), saturated sodium carbonate (100 ml.), sodium dihydrogen phosphate (100 ml.), and saturated sodium chloride (100 ml.), dried over anhydrous magnesium sulfate, and evaporated in vacuo to give 7.71 g. of solid product. Crystallization from ethyl acetate/hexane gives 3.87 g. of yellow solid 3,6-dihydro-4-methyl-6-(3-nitrophenyl)-2-thioxo-1,5(2H)-pyrimidinedicarboxylic acid, 1-ethyl 5-(1-methylethyl)ester; m.p. 163.5°–165°. TLC (silica gel; ethyl acetate:hexane, 1:2) $R_f$=0.36.

Anal. calc'd. for $C_{18}H_{21}N_3O_6S$: C, 53.06; H, 5.20; N, 10.31; S, 7.87. Found: C, 53.20; H, 5.03; N, 10.25; S, 7.79.

EXAMPLE 78

3,6-Dihydro-4-methyl-6-(3-nitrophenyl)-2-thioxo-1,5(2H)-pyrimidinedicarboxylic acid, bis(1-methylethyl) ester a)

2-[[(4-Methoxyphenyl)methyl]thio]-4-methyl-6-(3-nitrophenyl)-1,5(6H)-pyrimidinedicarboxylic acid, bis(1-methylethyl) ester 1,4-Dihydro-2-[[(4-methoxyphenyl)methyl]thio]-6-methyl-4-(3-nitrophenyl)-5-pyrimidinecarboxylic acid, 1-methylethyl ester (5.14 g., 11.3 mmole) is dissolved in dichloromethane (25 ml.) and cooled to 0° under argon. Bis(trimethylsilyl)trifluoroacetamide (3.0 ml., 12.4 mmole) is added and the reaction is stirred for 30 minutes at 0°. Pyridine (1.0 ml., 12.4 mmole) is then added followed by dropwise addition of isopropyl chloroformate (1.41 ml., 12.4 mmole) as a solution in dichloromethane (5 ml.). The reaction is stirred for one hour at 0° and then the ice bath is removed. After stirring for 3 hours at room temperature, additional isopropyl chloroformate (0.25 ml.) is added. After stirring for an additional hour at room temperature, ethyl acetate (75 ml.) is added and the reaction is washed with sodium bicarbonate (2×150 ml.), sodium dihydrogen phosphate (2×100 ml.), and saturated sodium chloride (2×100 ml.), dried over anhydrous magnesium sulfate, and stripped in vacuo to give 8.45 g. of 2-[[(4-methoxyphenyl)methyl]thio]-4-methyl-6-(3-nitrophenyl)-1,5(6H)-pyrimidinedicarboxylic acid, bis(1-methylethyl) ester as an oil.

b)

3,6-Dihydro-4-methyl-6-(3-nitrophenyl)-2-thioxo-1,5(2H)-pyrimidinedicarboxylic acid, bis(1-methylethyl) ester The ester product from part (a) (8.45 g.) is dissolved in dichloromethane (50 ml.) and treated with trifluoroacetic acid (5 ml.) and ethanethiol (1.5 ml.). The reaction is stirred at room temperature for 16 hours and then dichloromethane is added (50 ml.). The organic layer is washed with water (2×150 ml.), saturated sodium bicarbonate (2×150 ml.), saturated sodium carbonate (100 ml.), and saturated sodium chloride (100 ml.), dried over anhydrous magnesium sulfate, and evaporated to give 7.71 g. of solid product. Crystallization from ethyl acetate/hexane gives 3.34 g. of yellow solid 3,6-dihydro-4-methyl-6-(3-nitrophenyl)-2-thioxo-1,5(2H)-pyrimidinedicarboxylic acid, bis(1-methylethyl) ester; m.p. 138°–138.5°. TLC (silica gel; ethyl acetate: hexanes, 1:2) $R_f$=0.35.

Anal calc'd. for $C_{19}H_{23}N_3O_6S$: C, 54.15; H, 5.50; N, 9.97; S, 7.61. Found: C, 54.18; H, 5.40; N, 9.96; S, 7.64.

EXAMPLE 79

3,6-Dihydro-4-methyl-6-(3-nitrophenyl)-2-thioxo-1,5(2H)-pyrimidinedicarboxylic acid, 5-ethyl 1-(phenylmethyl) ester a)

2-[[(4-Methoxyphenyl)methyl]thio]-4-methyl6-(3-nitrophenyl)-1,5)6H)-pyrimidinedicarboxylic acid, 5-ethyl 1-(phenylmethyl) ester A solution of 1,4-dihydro-2-[[(4-methoxyphenyl)methyl]thio]-6-methyl-4-(3-nitrophenyl)-5-pyrimidinecarboxylic acid, ethyl ester (2.0 g., 4.5 mmole) in dichloromethane (20 ml.) containing pyridine (0.71 g., 9.1 mmole) is cooled to −10° and treated slowly with a solution of benzyl chloroformate (0.92 g., 5.4 mmole) in dichloromethane (5 ml.). After stirring for 16 hours at room temperature, the solution is diluted with dichloromethane and washed with water, 1N hydrochloric acid, sodium bicarbonate, and brine. The dried solution is evaporated to give 2.8 g. of an oil. Flash chromatography using dichloromethane yields 1.62 g. of 2-[[(4-methoxyphenyl)methyl]thio]-4-methyl-6-(3-nitrophenyl)-1,5(6H)-pyrimidinedicarboxylic acid, 5-ethyl 1-(phenylmethyl) ester as an oil.

b)

3,6-Dihydro-4-methyl-6-(3-nitrophenyl)-2-thioxo-1,5(2H)-pyrimidinedicarboxylic acid, 5-ethyl 1-(phenylmethyl) ester A solution of the ester product from part (a) (1.5 g., 2.6 mmole), trifluoroacetic acid (0.96 ml., 10 mmole) and ethanethiol (0.40 g., 60 mmole) in dichloromethane (20 ml.) is stirred at room temperature overnight. The solvent is evaporated and the semi-solid residue (1.3 g.) is flash chromatographed using ethyl acetate:hexane (1:4) to give an oil which slowly solidifies to 0.55 g. of yellow solid 3,6-dihydro-4-methyl-6-(3-nitrophenyl)-2-thioxo-1,5(2H)-pyrimidinedicarboxylic acid, 5-ethyl 1-(phenylmethyl) ester; m.p. 122°-124°. TLC (silica gel; ethyl acetate: hexanes, 1:1) $R_f$=0.50.

Anal. calc'd for $C_{22}H_{21}N_3O_6S$: C, 58.01; H, 4.64; N, 9.22; S, 7.03. Found: C, 58.09; H, 4.57; N, 9.10; S, 7.06.

EXAMPLE 80

6-(2,3-Dichlorophenyl)-3,6-dihydro-4-methyl-2-thioxo-1,5(2H)-pyrimidinedicarboxylic acid, bis(1-methylethyl) ester a)

4-(2,3-Dichlorophenyl)-1,4-dihydro-2-[[(4-methoxyphenyl)methyl]thio]-6-methyl-5-pyrimidinecarboxylic acid, 1-methylethyl ester A mixture of 2-[(2,3-dichlorophenyl)methylene]-3-oxobutanoic acid, 1-methylethyl ester (15.0 g., 0.049 mole), S-(4-methoxybenzyl)thiopseudourea hydrochloride (11.5 g., 0.049 mole), and sodium acetate (4.0 g., 0.049 mole) in dimethylformamide (90 ml.) is stirred and heated at 70° for 4 hours. After cooling, ether is added followed by extraction with water, sodium bicarbonate, and brine. The dried solution is evaporated to give 24.8 g. of an impure oily product. This material is flash chromatographed using ethyl acetate:haxane (1:3) to give 16.5 g. of an oil. A solution of this material in isopropyl ether yields 12.8 g. of colorless 4-(2,3-dichlorophenyl)-1,4-dihydro-2-[[(4-methoxyphenyl)methyl]thio]-6-methyl-5-pyrimidinecarboxylic acid, 1-methylethyl ester; m.p. 98°-100°.

Anal. calc'd. for $C_{23}H_{24}N_2Cl_2O_3S$: C, 57.61; H, 5.04; N, 5.84; S, 6.68. Found: C, 57.66; H, 5.02; N, 5.75; S, 6.64.

b)

2-[[(4-Methoxyphenyl)methyl]thio]-4-methyl-6-(2,3-dichloro)-1,5(6H)-pyrimidinedicarboxylic acdi, bis(1-methylethyl) ester A solution of the ester product from part (a) (3.0 g., 6 mmole) and pyridine (1.0 ml., 12 mmole) in dichloromethane (30 ml.) is cooled to 5° and treated dropwise with a solution of isopropyl chloroformate (0.89 g., 7 mmole) in dichloromethane (3 ml.). Work-up according to the procedure of Example 60 (b) gives 3.5 g. of cream colored 2-[[(4-methoxyphenyl)methyl]thio]-4-methyl-6-(2,3-dichlorophenyl)-1,5(6H)-pyrimidinedicarboxylic acid, bis (1-methylethyl) ester; m.p. 87°-89°.

Anal. calc'd. for $C_{27}H_{30}N_2Cl_2O_5S$: C, 57.34; H, 5.34; N, 4.95. Found: C, 57.06; H, 5.36; N, 4.91.

c)

6-(2,3-Dichlorophenyl)-3,6-dihydro-4-methyl-2-thioxo-1,5(2H)-pyrimidinedicarboxylic acid, bis(1-methylethyl) ester A solution of the ester product from part (b) (3.25 g., 5.7 mmole), trifluoroacetic acid (2.2 ml., 24 mmole), and ethanethiol (0.85 g., 13 mmole) in dichloromethane (30 ml.) is stirred at room temperature for 24 hours. Work-up according to the procedure of Example 63 (c) gives 2.0 g. of yellow solid 6-(2,3-dichlorophenyl)-3,6-dihydro-4-methyl-2-thioxo-1,5(2H)-pyrimidinedicarboxylic acid, bis(1-methylethyl) ester; m.p. 179°-181°. TLC (silica gel; ethyl acetate:hexane, 1:1) $R_f$=0.60.

Anal. calc'd. for $C_{19}H_{22}Cl_2N_2O_4S$: C, 51.35; H, 4.76; N, 6.30; Cl, 15.95; S, 7.21. Found: C, 51.70; H, 5.10; N, 6.14; Cl, 15.79; S, 7.17.

EXAMPLE 81

6-(2,3-Dichlorophenyl)-3,6-dihydro-4-methyl-2-thioxo-1,5(2H)-pyrimidinedicarboxylic acid, diethyl ester a)

4-(2,3-Dichlorophenyl)-1,4-dihydro-2-[[(4-methoxyphenyl)methyl]thio]-6-methyl-5-pyrimidinecarboxylic acid, ethyl ester A mixture of 2-[(2,3-dichlorophenyl)methylene]-3-oxobutanoic acid, ethyl ester (7.0 g., 24 mmole), S-(4-methoxybenzyl)thiopseudourea, hydrochloride (5.7 g., 24 mmole), and sodium acetate (2 g., 24 mmole) in dimethylformamide (50 ml.) is stirred and heated at 70° for 4 hours. After cooling, ether is added and the mixture is washed with water, sodium bicarbonate, and brine. The dried solution is concentrated until solids appear, then cooled overnight to give 6.3 g. of colorless solid 4-(2,3-dichlorophenyl)-1,4-dihydro-2-[[(4-methoxyphenyl)methyl]thio]-6-methyl-5-pyrimidinecarboxylic acid, ethyl ester; m.p. 134°-135°. TLC (silica gel; ethyl acetate:hexanes, 1:1) $R_f$=0.50.

Anal. calc'd. for $C_{22}H_{22}N_2Cl_2O_3S$: C, 56.77; H, 4.76; N, 6.02; Cl, 15.23; S, 6.88. Found: C, 56.74; H, 4.69; N, 5.65; Cl, 15.27; S, 6.87.

b)

2-[[(4-Methoxyphenyl)methyl]thio]-4-methyl-6-(2,3-dichlorophenyl)-1,5(6H)-pyrimidinedicarboxylic acid, diethyl ester A cold solution of the ester product from part (a) (2.0 g., 4 mmole) in dichloromethane (20 ml.) containing pyridine (0.7 ml., 9 mmole) is treated dropwise with a solution of ethyl chloroformate (0.56 g., 5 mmole) in dichloromethane (3 ml.), then stirred at room temperature for 16 hours. The solution is diluted with dichloromethane and washed with water, 1N hydrochloric acid, sodium bicarbonate, and brine. The dried solution is evaporated to 2.2 g. of an oil which solidifies; m.p. 120–122. Crystallization from acetonitrile (12 ml.) gives 1.9 g. of yellow solid 2-[[(4-methoxyphenyl)methyl]thio]-4-methyl-6-(2,3-dichlorophenyl)-1,5(6H)-pyrimidinedicarboxylic acid, diethyl ester; m.p. 124°–126°.

Anal. calc'd. for $C_{25}H_{26}N_2Cl_2O_5S$: C, 55.86; H, 4.87; N, 5.21. Found: C, 56.07; H, 4.87; N, 5.13.

c)
6-(2,3-Dichlorophenyl)-3,6-dihydro-4-methyl-2-thioxo-1,5(2H)-pyrimidinedicarboxylic acid, diethyl ester A solution of the diethyl ester product from part (b) (1.9 g., 3.5 mmole), trifluoroacetic acid (1.3 ml., 16.8 mmole) and ethanethiol (0.52 g., 8 mmole) in dichloromethane (25 ml.) is stirred at room temperature for 24 hours. The solvent is evaporated and the oily residue gradually solidifies. Trituration with isopropyl ether gives 1.36 g. of yellow solid 6-(2,3-dichlorophenyl)-3,6-dihydro-4-methyl-2-thioxo-1,5(2H)-pyrimidinedicarboxylic acid, diethyl ester; m.p. 155°–157°. TLC (silica gel; ethyl acetate: hexane, 1:1) $R_f = 0.55$.

Anal. calc'd. for $C_{17}H_{18}N_2Cl_2O_4S$: C, 48.92; H, 4.34; N, 6.71; Cl, 16.99; S, 7.68. Found: C, 49.07; H, 4.46; N, 6.99; Cl, 16.97; S, 7.70.

EXAMPLE 82

6-(2,3-Dichlorophenyl)-3,6-dihydro-4-methyl-2-thioxo-1,5(2H)-pyrimidinedicarboxylic acid, 5-ethyl 1-(1-methylethyl) ester a)
2-[[(4-Methoxyphenyl)methyl]thio]-4-methyl-6-(2,3-dichlorophenyl)-1,5(6H)-pyrimidinedicarboxylic acid, 5-ethyl 1-(1-methylethyl) ester A cold solution of the ester product from Example 79 (a) (2.0 g., 4.3 mmole) in dichloromethane (20 ml.) containing pyridine (0.7 ml., 9 mmole) is treated dropwise with a solution of isopropyl chloroformate (0.63 g., 5.1 mmole) in dichloromethane (3 ml.) and then stirred at room temperature for 24 hours. The solution is diluted with dichloromethane and washed with water, 1N hydrochloric acid, sodium bicarbonate, and brine. The dried solution is evaporated to give 2.17 g. of cream colored solid 2-[[(4-methoxyphenyl)methyl]thio]-4-methyl-6-(2,3-dichlorophenyl)-1,5(6H)-pyrimidinedicarboxylic acid, 5-ethyl 1-(1-methylethyl) ester; m.p. 97°–99°.

Anal. calc'd. for $C_{26}H_{28}N_2Cl_2O_5S$: C, 56.62; H, 5.11; N, 5.08. Found: C, 56.74; H, 5.12; N, 5.11.

b)
6-(2,3-Dichlorophenyl)-3,6-dihydro-4-methyl-2-thioxo-1,5(2H)-pyrimidinedicarboxylic acid, 5-ethyl 1-(1-methylethyl) ester A solution of the ester product from part (a) (1.88 g., 3.4 mmole), trifluoroacetic acid (1.26 ml., 16 mmole), and ethanethiol (0.52 g., 8 mmole) in dichloromethane (25 ml.) is stirred at room temperature for 24 hours. The solvent is evaporated and the solid residue is treated with isopropyl ether to give 1.3 g. of product; m.p. 153–155. Crystallization from acetonitrile (10 ml.) yields 1.2 g. of yellow solid 6-(2,3-dichlorophenyl)-3,6-dihydro-4-methyl-2-thioxo-1,5(2H)-pyrimidinedicarboxylic acid, 5-ethyl 1-(1-methylethyl) ester; m.p. 157°–159°. TLC (silica gel; ethyl acetate:hexanes, 1:1) $R_f = 0.55$.

Anal. calc'd for $C_{18}H_{20}N_2Cl_2O_4S$: C, 50.11; H, 4.67; N, 6.49; Cl, 16.43; S, 7.43. Found: C, 50.07; H, 4.69; N, 6.43; Cl, 16.41; S, 7.42.

EXAMPLE 83

6-(2-Chloro-3-nitrophenyl)-3,6-dihydro-4-methyl-2-thioxo-1,5(2H)-pyrimidinedicarboxylic acid, diethyl ester a)
4-(2-Chloro-3-nitrophenyl)-1,4-dihydro-2-[[(4-methoxyphenyl)methyl]thio]-6-methyl-5-pyrimidinecarboxylic acid, ethyl ester A mixture of 2-[(2-chloro-3-nitrophenyl)methylene]-3-oxobutanoic acid, ethyl ester (1.2 g., 4.3 mmole), S-(4-methoxybenzyl)thiopseudourea, hydrochloride (1.0 g., 4.3 mmole), and sodium acetate (0.36 g., 4.4 mmole) in dimethylformamide (8 ml.) is stirred at 70° for 4 hours. After cooling, ether is added and the solution is washed with water, sodium bicarbonate, and brine. The dried solution is evaporated to give 1.68 g. of a yellow solid. Flash chromatography eluting with ethyl acetate:hexanes (1:2) gives 1.0 g. of yellow solid 4-(2-chloro-3-nitrophenyl)-1,4-dihydro-2-[[(4-methoxyphenyl)methyl]thio]-6-methyl-5-pyrimidinecarboxylic acid, ethyl ester; m.p. 155°–157°. TLC (silica gel; ethyl acetate:hexanes, 1:1) $R_f = 0.50$.

Anal. calc'd. for $C_{22}H_{22}N_3ClO_5S$: C, 55.51; H, 4.65; N, 8.82; Cl, 7.44; S, 6.73. Found: C, 55.48; H, 4.67; N, 8.75; Cl, 7.24; S, 6.54.

b)
6-(2-Chloro-3-nitrophenyl)-2-[[(4-methoxypenyl)methyl]thio]-4-methyl-1,5(6H)-pyrimidinedicarboxylic acid, diethyl ester A cold solution of the ethyl ester product from part (a) (2.16 g., 4.5 mmole) in dichloromethane (25 ml.) containing pyridine (0.76 ml.) is treated dropwise with ethyl chloroformate (0.60 g., 5.6 mmole) and then stirred at room temperature for 16 hours. The solution is diluted with ether and washed with water, 1N hydrochloric acid, saturated sodium bicarbonate, and brine. The dried solution is evaporated to give 2.27 g., of 6-(2-chloro-3-nitrophenyl)-2-[[(4-methoxyphenyl)methyl]thio]-4-methyl-1,5(6H)-pyrimidinedicarboxylic acid, diethyl ester as an oil.

Anal. calc'd. for $C_{25}H_{26}N_3ClO_7S$: C, 54.79; H, 4.78; N, 7.66. Found: C, 55.14; H, 4.99; N, 7.44.

c)
6-(2-Chloro-3-nitrophenyl)-3,6-dihydro-4-methyl-2-thioxo-1,5(2H)-pyrimidinedicarboxylic acid, diethyl ester A solution of the diethyl ester product from part (b) (2.1 g., 3.8 mmole), trifluoroacetic acid (1.12 ml., 13 mmole), and ethanethiol (0.49 g., 7 mmole) in dichloromethane (20 ml.) is stirred at room temperature for 16 hours. The solvent is evaporated and the oil residue is treated with hot isopropyl ether. The solvent is decanted from a small amount of insoluble oil. The cooled solution gives 0.97 g. of yellow solid 6-(2-chloro-3-nitrophenyl)-3,6-dihydro-4-methyl-2-thioxo-1,5(2H)-pyrimidinedicarboxylic acid, diethyl ester; m.p. 136°–138° (dec.). TLC (silica gel; ethyl acetate:hexanes, 1:1) $R_f = 0.50$.

Anal. calc'd. for $C_{17}H_{18}N_3ClO_6S$: C, 47.72; H, 4.23; N, 9.82; Cl, 8.28, S, 7.49. Found: C, 48.00, H, 4.33; N, 9.51; Cl, 8.11, S, 7.44.

EXAMPLE 84

6-(2-Chloro-3-nitrophenyl)-3,6-dihydro-4-methyl-2-thioxo-1,5(2H)-pyrimidinedicarboxylic acid, 5-ethyl 1-(1-methylethyl) ester a)

6-(2-Chloro-3-nitrophenyl)-2-[[(4-methoxyphenyl)methyl]thio]-4-methyl-1,5(6H)-pyrimidinecarboxylic acid, 5-ethyl 1-(1-methylethyl) ester A solution of the ethyl ester product from Example 83 (a) (1.5 g., 3.15 mmole) in dry dichloromethane (10 ml.) under argon at 0°-5° is treated with pyridine (0.5 ml., 0.49 g., 6.2 mmole) and isopropyl chloroformate (0.5 ml., 0.54 g., 4.4 mmole). The mixture is stirred overnight at room temperature. The mixture is diluted with ethyl acetate and washed with water, 1N hydrochloric acid, water, sodium bicarbonate, water, and saturated brine. The aqueous washes are back-extracted with fresh ethyl acetate. The combined organic solutions are dried over anhydrous magnesium sulfate and concentrated in vacuo to give 1.87 g. of 6-(2-chloro-3-nitrophenyl)-2-[[(4-methoxyphenyl)methyl]thio]-4-methyl-1,5(6H)-pyrimidinedicarboxylic acid, 5-ethyl 1-(1-methylethyl) ester, as an amber oil. TLC (silica gel; ethyl acetate:hexanes, 1:1) $R_f=0.56$.

Anal. calc'd. for $C_{26}H_{28}ClN_3O_7S$: C, 55,56; H, 5.02; N, 7.48; Cl, 6.31; S, 5.71. Found: C, 55.32; H, 4.87; N, 7.02; Cl, 6.29; S, 5.47.

b)

6-(2-Chloro-3-nitrophenyl)-3,6-dihydro-4-methyl-2-thioxo-1,5(2H)-pyrimidinedicarboxylic acid,5-ethyl 1-(1-methylethyl) ester A solution of the ester product from part (a) (1.8 g., 3.2 mmole) in dry dichloromethane (15 ml.) under argon at room temperature is treated with trifluoroacetic acid (0.75 ml., 1.12 g., 9.6 mmole) and ethanethiol (0.47 ml., 0.4 g., 6.4 mmole). The mixture is heated at reflux for 2 hours. The volatiles are stripped in vacuo and the residue is triturated with isopropyl ether to give 1.2 g. of product. Recrystallization from isopropyl ether/dichloromethane gives 1.17 g. of light yellow solid 6-(2-chloro-3-nitrophenyl)-3,6-dihydro-4-methyl-2-thioxo-1,5(2H)-pyrimidinedicarboxylic acid, 5-ethyl 1-(1-methylethyl) ester; m.p. 161°-164°. TLC(silica gel; ethyl acetate:hexanes) $R_f=0.56$.

Anal. calc'd. for $C_{18}H_{20}ClN_3O_6S$: C, 48.92; H, 4.56; N, 9.51; Cl, 8.02; S, 7.26. Found: C, 48.60; H, 4.54; N, 9.13; Cl, 7.98; S, 7.25.

EXAMPLE 85

3,6-Dihydro-4-methyl-6-[2-(methylthio)-3-pyridinyl]-2-thioxo-1,5(2H)-pyrimidinedicarboxylic acid, bis(1-methylethyl) ester a)

1,4-Dihydro-2-[[(4-methoxyphenyl)methyl]thio]-6-methyl-4-[2-(methylthio)-3-pyridinyl-5-pyrimidinecarboxylic acid, 1-methylethyl ester A mixture of 2-[[2-(methylthio)-3-pyridinyl]methylene]-3-oxobutanoic acid, 1-methylethyl ester and S-(4-methoxybenzyl)thiopseudourea, hydrochloride (0.86 g., 3.7 mmole) in dimethylformamide (5 ml.) is treated with sodium acetate (0.30 g., 3.7 mmole) and heated at 70° for 3.5 hours. The reaction mixture is diluted with ethyl acetate, and washed with sodium bicarbonate, water (twice), and saturated brine. The aqueous washes are back extracted with fresh ethyl acetate. The combined organic fractions are dried over anhydrous magnesium sulfate and concentrated in vacuo to give 1.84 g. of an oil. Flash chromatography eluting with ethyl acetate:hexanes (1:4) gives 1.38 g. of 1,4-dihydro-2-[[(4-methoxyphenyl)methyl]thio]-6-methyl-4-[2-(methylthio)-3-pyridinyl]-5-pyrimidinecarboxylic acid, 1-methylethyl ester as a foam. TLC (silica gel; ethyl acetate:hexanes, 1:1) $R_f=0.50$.

Anal calc'd. for $C_{23}H_{27}N_3O_3S_2$: C, 60.36; H, 5.95; N, 9.18; S, 14.01. Found: C, 59.71; H, 5.94; N, 8.93; S, 13.91.

b)

2-[[{4-Methoxyphenyl)methylthio]-4-methyl-6-[2-(methylthio)-3-pyridinyl]-1,5(6H)-pyrimidinedicarboxylic acid, bis(1-methylethyl) ester The 1-methylethyl ester product from part (a) (1.12 g., 2.44 mmole) in dry dichloromethane (10 ml.) under argon at 0°-5° is treated with pyridine (0.6 ml., 0.58 g., 7.34 mmole) and isopropyl chloroformate (0.36 ml., 0.38 g., 3.17 mmole) and stirred at room temperature for 3 hours. The mixture is diluted with ethyl acetate and washed with 1N hydrochloric acid, sodium bicarbonate, water, and saturated brine. The aqueous washes are back-extracted with fresh ethyl acetate. The organic layers are combined, dried over anhydrous magnesium sulfate, and concentrated in vacuo to give 1.31 g. of 2-[[(4-methoxyphenyl)methyl]thio]-4-methyl-6-[2-(methylthio)-3-pyridinyl]-1,5(6H)-pyrimidinedicarboxylic acid, bis(1-methylethyl) ester as a homogeneous product. TLC (silica gel; ethyl acetate:hexanes, 1:1) $R_f=0.62$.

Anal. calc'd. for $C_{27}H_{33}N_3O_5S_2\cdot H_2O$: C, 57.73; H, 6.28; N, 7.48; S, 11.4. Found: C, 57.96; H, 5.98; N, 7.30; S, 11.18.

c)

3,6-Dihydro-4-methyl-6-[2-(methylthio)-3-pyridinyl]-2-thioxo-1,5(2H)-pyrimidinedicarboxylic acid, bis(1-methylethyl) ester A solution of the bis (1-methylethyl) ester product from part (b) (1.3 g., 2.39 mmole) in dry dichloromethane (10 ml.) under argon at 0°-5° is treated with trifluoroacetic acid (0.55 ml., 0.82 g., 7.18 mmole) and ethanethiol (0.36 ml., 0.3 g., 4.78 mmole) and heated at reflux for 7 hours. The volatiles are stripped in vacuo and the residue is dissolved in ethyl acetate and washed with sodium bicarbonate, water, and saturated brine. The aqueous fractions are back extracted with fresh ethyl acetate. The organic fractions are combined, dried over anhydrous magnesium sulfate, and concentrated in vacuo to give 1.45 g. of crude product. Flash chromatography eluting with ethyl acetate:hexanes (1:3) gives 0.93 g. of a homogeneous product that is crystallized from isopropyl ether/hexane to give 0.78 g. of 3,6-dihydro-4-methyl-6-[2-(methylthio)-3-pyridinyl]-2-thioxo-1,5(2H)-pyrimidinedicarboxylic acid, bis(1-methylethyl) ester as a pale yellow powder; m.p. 119°-121°. TLC (silica gel; ethyl acetate:hexanes, 1:1) $R_f=0.53$.

Anal. calc'd. for $C_{19}H_{25}N_3O_4S_2$: C, 53.88; H, 5.95; N, 9.92; S, 15.14. Found: C, 53.94; H, 6.06; N, 9.76; S, 15.22.

EXAMPLE 86

3,6-Dihydro-4-methyl-6-(3-nitrophenyl)-2-thioxo-1,5(2H)-pyrimidinedicarboxylic acid, 1-(1-methylethyl) 5-[2-[methyl(phenylmethyl)amino]ethyl] ester, monohydrochloride a)

1,4-Dihydro-2-[[(4-methoxyphenyl)methyl]thio]-6-methyl-4-(3-nitrophenyl)-5-pyrimidinecarboxylic acid, 2-[methyl(phenylmethyl)amino]ethyl ester A solution of 2-[(3-nitrophenyl)methylene]-3-oxobutanoic acid, 2-[methyl(phenylmethyl)amino]ethyl ester (3.0 g., 7.85 mmole) in dry dimethylformamide (8 ml.) is treated with S-(4-methoxybenzyl)thiopseudourea, hydrochloride (1.83 g., 7.85 mmole) and sodium acetate (0.64 g., 7.85 mmole) and heated at 75° for 4 hours. The mixture is cooled, diluted with ethyl acetate, and washed with water, sodium bicarbonate, water, and saturated brine. The aqueous fractions are back-washed with fresh ethyl acetate. The organic fractions are combined, dried over anhydrous magnesium sulfate, and concentrated in vacuo to give 4.0 g. of crude product. Flash chromatography eluting with ethyl acetate:hexane (1:2) gives 1.76 g. of 1,4-dihydro-2-[[(4-methoxyphenyl)methyl]thio]-6-methyl-4-(3-nitrophenyl)-5-pyrimidinecarboxylic acid, 2-[methyl(phenylmethyl)amino]ethyl ester. TLC (silica gel; ethyl acetate:hexanes, 1:1) $R_f$=0.19.

Anal. calc'd. for $C_{30}H_{32}N_4O_5S$: C, 64.26; H, 5.75; N, 9.99; S, 5.72. Found: C, 63.13; H, 5.80; N, 9.75; S, 5.52.

b)

2-[-[(4-Methoxyphenyl)methyl]thio]-4-methyl-6-(3-nitrophenyl)-1,5(6H)-pyrimidinedicarboxylic acid, 1-(1-methylethyl) 5-[2-[methyl(phenylmethyl)amino]ethyl] ester The ester product from part (a) (1.76 g., 3.1 mmole) in dry dichloromethane (15 ml.) under argon at 0°–5° is treated with pyridine (1.0 ml., 12.6 mmole) followed by isopropyl chloroformate (0.4 ml., 0.43 g., 3.5 mmole) over a 5 minute period. The mixture is allowed to warm to room temperature and stirred for 2 hours. The volatiles are stripped in vacuo and the residue is dissolved in ethyl acetate and washed with sodium bicarbonate, water, and saturated brine. The aqueous fractions are back-extracted with fresh ethyl acetate. The organic fractions are combined, dried over anhydrous magnesium sulfate, and concentrated in vacuo to give 1.93 g. of 2-[[(4-methoxyphenyl)methyl]thio]-4-methyl-6-(3-nitrophenyl)-1,5(6H)-pyrimidinedicarboxylic acid, 1-(1-methylethyl) 5-[2-[methyl(phenylmethyl)amino]ethyl]-ester. TLC (silica gel; ethyl acetate hexanes, 1:1) $R_f$=0.47.

c)

3,6-Dihydro-4-methyl-6-(3-nitrophenyl)-2-thioxo-1,5(2H)-pyrimidinedicarboxylic acid, 1-(1-methylethyl) 5-[2-[methyl(phenylmethyl)amino]ethyl] ester, monohydrochloride The ester product from part (b) (1.93 g., 3.0 mmole) in dry dichloromethane (15 ml.) under argon at 0°–5° is treated with trifluoroacetic acid (0.7 ml., 1.02 g., 9.0 mmole) and ethanethiol (0.45 ml., 0.38 g., 6.0 mmole) and the reaction mixture is stirred overnight at room temperature. Additional trifluoroacetic acid (0.5 ml., 0.73 g., 6.4 mmole) is added and the reaction mixture is heated at reflux for 2 hours. The volatiles are stripped in vacuo and the residue is dissolved in ethyl acetate and washed with sodium bicarbonate, water, and saturated brine. The aqueous fractions are back-extracted with fresh ethyl acetate. The organic fractions are combined, dried over anhydrous magnesium sulfate, and concentrated in vacuo to give 2.0 g. of an oil. Flash chromatography eluting with ethyl acetate:hexanes (1:2) gives 0.9 g. of the desired product as an oil.

This oil product is dissolved in ether and treated slowly with ethereal hydrochloric acid (20% excess) to give 0.7 g. of 3,6-dihydro-4-methyl-3-(nitrophenyl)-2-thioxo-1,5(2H)-pyrimidinedicarboxylic acid, 1-(1-methylethyl) 5-[2-[methylphenylmethyl)amino]ethyl]-ester, monohydrochloride; m.p. 105°–110°. TLC (silica gel; ethyl acetate: hexanes) $R_f$=0.35 (free base).

Anal calc'd. for $C_{26}H_{30}N_4O_6S \cdot HCl \cdot 0.3\ H_2O$: C, 54.93; H, 5.60; N, 9.85; S, 5.64; Cl, 6.24. Found: C, 54.9; H, 5.55; N, 9.64; S, 5.35; Cl, 6.19.

EXAMPLE 87

3,6-Dihydro-4-methyl-6-{3-nitrophenyl)-2-thioxo-1,5(2H)-pyrimidinedicarboxylic acid, 1-(1-methylethyl 5-[2-[4-(diphenylmethyl]-1-piperazinyl]ethyl] ester, dihydrochloride a)

1,4-Dihydro-2-[[(4-methoxyphenyl)methyl]thio]-6-methyl-4-(3-nitrophenyl)-5-pyrimidinecarboxylic acid, 2-[4-(diphenylmethyl)-1-piperazinyl]ethyl ester A mixture of 2-[(3-nitrophenyl)methylene]-3-oxobutanoic acid, 2-[4-(diphenylmethyl)-1-piperazinyl]ethyl ester (2.78 g., 5.4 mmole) and S-(4-methoxybenzyl)thiopseudourea, hydrochloride (1.26 g., 5.4 mmole) in toluene (15 ml.) under argon is treated with sodium acetate (0.45 g., 5.4 mmole) and warmed at 70°–75° for 4 hours. The cooled reaction mixture is diluted with ethyl acetate and washed with water (twice) and saturated brine. The aqueous fractions are back-extracted with fresh ethyl acetate. The organic extracts are combined, dried over anhydrous magnesium sulfate, and concentrated in vacuo to give 3.82 g. of an oil. Flash chromatography eluting with ethyl acetate:hexanes gives 2.25 g. of 1,4-dihydro-2-[[(4-methoxyphenyl)methyl]-thio]-6-methyl-4-(3-nitrophenyl)-5-pyrimidinecarboxylic acid, 2-[4-(diphenylmethyl)-1-piperazinyl]ethyl ester. TLC (silica gel; ethyl acetate:methanol, 10:1) $R_f$=0.57.

Anal. calc'd. for $C_{39}H_{41}N_5O_5S \cdot 0.7\ H_2O$: C, 66.49; H, 6.07; N, 9.94; S, 4.53. Found: C, 66.56; H, 5.87; N, 9.82; S, 4.50.

b)

2-[[(4-Methoxyphenyl)methyl]thio]-4-methyl-6-(3-nitrophenyl)-1,5(6H)-pyrimidinedicarboxylic acid, 1-(1-methylethyl) 5-[2-[4-(diphenylmethyl)-1-piperazinyl]ethyl] ester A solution of the ester product from part (a) (2.25 g., 3.26 mmole) in dichloromethane (15 ml.) and pyridine (2 ml.) at room temperature under argon is treated with isopropyl chloroformate (0.38 ml., 0.405 g., 3.32 mmole). Some warming is noted. Additional isopropyl chloroformate (0.1 ml.) is added and after 30 minutes the volatiles are stripped in vacuo. The residue is dissolved in ethyl acetate and washed with sodium bicarbonate, water, and saturated brine. The aqueous fractions are back-extracted with fresh ethyl acetate. The organic fractions are combined, dried over anhydrous magnesium sulfate, and concentrated in vacuo to give 2.45 g. of crude product. Flash chromatography eluting with ethyl acetate:hexanes (2:3) gives 2.1 g. of 2-[[(4-methoxyphenyl)methyl]thio]-4-methyl-6-(3-nitrophenyl)-1,5(6H)-pyrimidinedicarboxylic acid, 1-(1-methylethyl) 5-[2-[4-(diphenylmethyl)-1-piperazinyl]ethyl]ester. TLC (silica gel; ethyl acetate) $R_f=0.53$.

Anal. calc'd. for $C_{43}H_{47}N_5O_7S$: C, 66.93; H, 6.09; N, 9.00; S, 4.12. Found: C, 66.85; H, 6.11; N, 8.99; S, 4.01.

c)
3,6-Dihydro-4-methyl-6-(3-nitrophenyl)-2-thioxo-1,5(2H)-pyrimidinedicarboxylic acid, 1-(1-methylethyl) 5-[2-[4-(diphenylmethyl)-1-piperazinyl]ethyl]ester, dihydrochloride A solution of the ester product from part (b) (2.1 g., 2.7 mmole) in dichloromethane (15 ml.) under argon at room temperature is treated with trifluoroacetic acid (1 ml., 1.48 g., 12.9 mmole) and ethanethiol (0.5 ml., 0.42 g., 6.6 mmole). The mixture is heated at reflux temperature for 6 hours. The volatiles are removed in vacuo and the residue is dissolved in ethyl acetate and washed with sodium bicarbonate, water, and saturated brine. The aqueous fractions are back-extracted with fresh ethyl acetate. The organic fractions are combined, dried over anhydrous magnesium sulfate, and concentrated in vacuo to give 2.3 g. of an oil that solidifies on the vacuum pump. Trituration with ethyl acetate/hexanes give 1.6 g. of homogeneous 3,6-dihydro-4-methyl-6-(3-nitrophenyl)-2-thioxo-1,5(2H)-pyrimidinedicarboxylic acid, 1-(1-methylethyl) 5-[2-[4-(diphenylmethyl)-1-piperazinyl]-ethyl]ester as a homogeneous product; m.p. 200-203 (dec.). TLC (silica gel; ethyl acetate) $R_f=0.52$.

Anal. calc'd. for $C_{35}H_{39}N_5O_6S$: C, 63.91; H, 5.98; N, 10.65; S, 4.88. Found: C, 63.90; H, 6.06; N, 10.37; S, 4.93.

The above free base is dissolved in hot acetone (200 ml.), cooled to room temperature, and treated with ethereal hydrochloric acid (excess) causing the turbid solution to clarify. Solvent is removed in vacuo and the residue is triturated with ether to give 1.59 g. of 3,6-dihydro-4-methyl-6-(3-nitrophenyl)-2-thioxo-1,5(2H)-pyrimidinedicarboxylic acid, 1-(1-methylethyl) 5-[2-[4-(diphenylmethyl)-1-piperazinyl]ethyl]ester, dihydrochloride; m.p. 173° (foam), 190°-200° (dec.).

Anal. calc'd. for: $C_{35}H_{39}N_5O_6S\cdot 2HCl$ C, 57.53; H, 5.66; N, 9.58; Cl, 9.71; S, 4.39. Found: C, 57.32; H, 5.81; N, 9.33; Cl, 9.73; S, 4.11.

EXAMPLE 88

3,6-Dihydro-4-methyl-6-(3-nitrophenyl)-2-thioxo-1,5(2H)-pyrimidinedicarboxylic acid, 1-ethyl ester a)
1,4-Dihydro-2-[[(4-methoxyphenyl)methyl]thio]-6-methyl-4-(3-nitrophenyl)-5-pyrimidinecarboxylic acid, 1,1-dimethylethyl ester, monohydrochloride A solution of 2-[(3-nitrophenyl)methylene]-3-oxobutanoic acid, 1,1-dimethylethyl ester (28 g., 96.12 mmole) in dimethylformamide (98 ml.) is treated with S-(4-methoxybenzyl)thiopseudourea, hydrochloride (22.37 g., 96.12 mmole) and sodium acetate (7.9 g., 96.12 mmole). The mixture is heated at 60° overnight, diluted with ether, and filtered to remove sodium chloride. The filtrate is washed with water (150 ml.), sodium bicarbonate (150 ml.), and brine. The organic layer is dried over anhydrous magnesium sulfate, filtered, and stripped to give an oil. This oil is dissolved in dichloromethane (300 ml.) and treated with methanolic hydrochloric acid (1 eq., 96.12 mmole) to crystallize out 41.74 g. of product. A second crop of 2.77 g. is collected by reducing the volume of the mother liquor and cooling at 0° overnight to give a total of 44.51 g. of white solid 1,4-dihydro-2-[[(4-methoxyphenyl)methyl]thio]-6-methyl-4-(3-nitrophenyl)-5-pyrimidinecarboxylic acid, 1,1-dimethylethyl ester; m.p. 192°. TLC (silica gel; ethyl acetate:hexanes, 1:2 $R_f=0.51$.

Anal. calc'd. for $C_{24}H_{27}N_3O_5S\cdot HCl$: C, 56.97; H, 5.57; N, 8.30; S, 6.34; Cl, 7.01. Found: C, 57.02; H, 5.59; N, 8.26; S, 6.30; Cl, 7.08.

b)
1,4-Dihydro-2-[[(4-methoxyphenyl)methyl]thio]-6-methyl-4-(3-nitrophenyl)-5-pyrimidinecarboxylic acid The 1,1-dimethylethyl ester product from part (a) (13.5 g., 26.7 mmole) is added to a mixture of trifluoroacetic acid (125 ml.) and anisole (12.5 ml.) at 0° under nitrogen. After stirring for 30 minutes, the trifluoroacetic acid is stripped in vacuo at 0°. The resulting residue is taken up into ethyl acetate/dichloromethane and a white solid is precipitated out by the addition of hexane. This solid is washed with hexanes and dried to give 9.66 g. of 1,4-dihydro-2-[[(4-methoxyphenyl)methyl]thio]-6-methyl-4-(3-nitrophenyl)-5-pyrimidinecarboxylic acid; m.p. 90° (shrinks), 103°-106° (foams).

c)
2-[[(4-Methoxyphenyl)methyl]thio]-4-methyl-6-(3-nitrophenyl)-1,5(6H)-pyrimidinedicarboxylic acid, 1-ethyl ester Bis(trimethylsilyl)trifluoroacetamide (2.1 eq., 2.2 ml., 8.4 mmole) is added to a mixture of the acid product from part (b) (1.65 g., 3.99 mmole) in dry dichloromethane (7 ml.) at 0° under nitrogen. After 30 minutes, pyridine (2.1 eq., 0.68 ml., 8.4 mmole) is added to the mixture followed by ethyl chloroformate (2.1 eq., 0.8 ml., 8.4 mmole). The mixture is stirred at room temperature overnight. The reaction mixture is then poured into ethyl acetate (20 ml.) and washed witrh saturated aqueous sodium bicarbonate, saturated sodium dihydrogen phosphate, and brine. The organic layer is dried over anhydrous magnesium sulfate to give 2.8 g. of yellow solid 2-[[(4-methoxyphenyl)methyl]thio]-4-methyl-6-(3-nitrophenyl)-1,5(6H)-pyrimidinedicarboxylic acid, 1-ethyl ester.

d)
3,6-Dihydro-4-methyl-6-(3-nitrophenyl)-2-thioxo-1,5(2H)-pyrimidinedicarboxylic acid, 1-ethyl ester Ethanethiol (2 eq., 763 μl., 10.3 mmole) is added to a mixture of the 1-ethyl ester product from part (c) (2.57 g., 5.16 mmole) in trifluoroacetic acid (2.1 ml.) and dry dichloromethane ml.) under nitrogen and the mixture is stirred overnight at room temperature. The reaction mixture is diluted with dichloromethane (20 ml.) and washed with water (2×15 ml.). The product is extracted into 1N sodium hydroxide (three times) and the basic layers are combined and adjusted to pH 2 with concentrated hydrochloric acid. The product is extracted into ethyl acetate (twice), dried, and stripped to give 1.26 g. of yellow solid. Recrystallization from acetonitrile gives 630 mg. of yellow crystalline solid 3,6-dihydro-4-methyl-6-(3-nitrophenyl)-2-thioxo-1,5(2H)-pyrimidinedicarboxylic acid, 1-ethyl ester; m.p. 199°-202° (dec.). TLC (silica gel; ethyl acetate:dichloromethane:methanol, 8:1:1) $R_f=0.5$.

Anal. calc'd. for $C_{15}H_{15}N_3O_6S$: C, 49.32; H, 4.13; N, 11.50; S, 8.78. Found: C, 49.15; H, 4.14; N, 11.51; S, 8.39.

EXAMPLE 89

3,6-Dihydro-4-methyl-6-(3-nitrophenyl)-2-thioxo-1,5(2H)-pyrimidinedicarboxylic acid, 5-ethyl 1-[2-[methyl(phenylmethyl)amino]ethyl]ester, monohydrochloride a)

2-[[(4-Methoxyphenyl)methyl]thio]-4-methyl-6-(3-nitrophenyl)-1,5(6H)-pyrimidinedicarboxylic acid, 5-ethyl 1-[2-[methyl(phenylmethyl)amino]ethyl]ester Phosgene in benzene (1.3 eq., 5.89 mmole, 4.5 ml. of 1.3M solution) is added dropwise to a solution of 1,4-dihydro-2-[[(4-methoxyphenyl)methyl]thio]-6-methyl-4-(3-nitrophenyl)-5-pyrimidinecarboxylic acid, ethyl ester (2.0 g., 4.5 mmole) [prepared as set forth in Example 72 (a)] in neat pyridine (10 ml.). After 20 minutes, N-benzyl-N-methyl ethanolamine (1.6 eq., 1.17 ml., 7.2 mmole) is added as a solution in pyridine (2 ml.). The mixture is stirred overnight at room temperature. The reaction mixture is diluted with ethyl acetate (30 ml.) and washed with saturated aqueous sodium bicarbonate (2×15 ml.), saturated aqueous sodium dihydrogen phosphate (2×15 ml.), and water (15 ml.). The organic layer is dried over anhydrous magnesium sulfate, filtered, and adsorbed onto Celite. Flash chromatography eluting with ether:hexanes (1:1) gives 2.51g. of 2-[[(4-methoxyphenyl)methyl]thio]-4-methyl-6-(3-nitrophenyl)-1,5(6H)-pyrimidinedicarboxylic acid, 5-ethyl 1-[2-[methyl(phenylmethyl)amino]ethyl ester as a green oil.

b)

3,6-Dihydro-4-methyl-6-(3-nitrophenyl)-2-thioxo-1,5(2H)-pyrimidinedicarboxylic acid, 5-ethyl 1-[2-[methyl(phenylmethyl)amino]ethyl]ester, monohydrochloride Ethanethiol (2 eq., 0.59 ml., 7.94 mmol.) is added to a mixture of the ester product from part (a) (2.51 g., 3.97 mmole) in 10% trifluoroacetic acid/dichloromethane (1.6 ml. in 16 ml. dry dichloromethane) at room temperature under nitrogen. The mixture is stirred for 48 hours. The mixture is diluted with dichloromethane 16 ml.) and washed with water 2×15 ml.), sodium bicarbonate (2×15 ml.), and sodium dihydrogen phosphate (2×15 ml.). The resulting organic phase is dried over anhydrous magnesium sulfate, and stripped in vacuo to give an oil. The crude free base is flash chromatographed eluting with ethyl acetate:hexanes (1:2) to give a green oil. Ethereal hydrochloric acid is added to the free base in ether at 0° to give 710 mg. of 3,6-dihydro-4-methyl-6-(3-nitrophenyl)-2-thioxo-1,5(2H)-pyrimidinedicarboxylic acid, 5-ethyl 1-[2-[methyl(phenylmethyl)amino]ethyl]ester, monohydrochloride as a yellow solid; m.p. 80° (vaporizes). TLC (silica gel; ethyl acetate:hexanes, 1:2) $R_f=0.19$.

Anal. calc'd. for $C_{25}H_{28}N_4SO_6 \cdot HCl \cdot 0.6\ H_2O$: C, 53.63; H, 5.25; N, 10.00; S, 5.73; Cl, 6.33. Found: C, 53.63; H, 5.22; N, 9.90; S, 5.58; Cl, 6.09.

EXAMPLE 90

3,6-Dihydro-4-methyl-6-(3-nitrophenyl)-2-thioxo-1,5(2H)-pyrimidinedicarboxylic acid, 5-(1-methylethyl) 1-[2-[methyl(phenylmethyl)amino]ethyl ester, monohydrochloride a)

2-[[(4-Methoxyphenyl)methyl]thio]-4-methyl-6-(3-nitrophenyl)-1,5(6H)-pyrimidinedicarboxylic acid, 5-(1-methylethyl) 1-[2-[methyl(phenylmethyl)amino]ethyl]ester Phosgene in benzene (1.3 g., 5.7 mmole, 4.4 ml. of 1.3M solution) is added dropwise to a solution of 1,4-dihydro-2-[[(4-methoxyphenyl)methyl]thio]-6-methyl-4-(3-nitrophenyl)-5-pyrimidinecarboxylic acid, 1-methylethyl ester (2.0 g., 4.39 mmole) [prepared as set forth in Example 76 (a)] in neat pyridine (10 ml.) at room temperature under nitrogen. After 30 minutes, N-benzyl-N-methyl ethanolamine (1.6 eq., 1.14 ml., 7.0 mmole) is added and the mixture is stirred for 48 hours. The mixture is diluted with ethyl acetate (50 ml.) and washed with sodium bicarbonate (2×25 ml.), sodium dihydrogen phosphate (2×25 ml.) and water (2×25 ml.). The organic phase is dried over anhydrous sodium sulfate, filtered and adsorbed onto Celite (10 g.). Flash chromatography eluting with ether: hexanes (1:1) gives 2.08 g. of 2-[[(4-methoxyphenyl)methyl]thio]-4-methyl-6-(3-nitrophenyl)-1,5(6H)-pyrimidinedicarboxylic acid, 5-(1-methylethyl) 1-[2-[methyl(phenylmethyl)amino]ethyl]ester as a green oil.

b)

3,6-Dihydro-4-methyl-6-(3-nitrophenyl)-2-thioxo-1,5(2H)-pyrimidinedicarboxylic acid, 5-(1-methylethyl) 1-[2-[methyl(phenylmethyl)amino]ethyl]ester, monohydrochloride The ester product from part (a) (1.02 g., 3.12 mmole) is dissolved in 10% trifluoroacetic acid/dichloromethane (1.3 ml. trifluoroacetic acid/13 ml. dichloromethane) and ethanethiol (2 eq., 461 µl., 6.24 mmole) is added. The mixture is stirred for 48 hours, then diluted with dichloromethane (50 ml.) and washed with water (2×25 ml.), sodium bicarbonate (2×25 ml.), sodium dihydrogen phosphate (2×25 ml.), and water (2×25 ml.). The organic phase is dried over anhydrous sodium sulfate, filtered, and stripped. Flash chromatography eluting with ethyl acetate:hexanes (1:2) gives the product as a green foam. This material is taken up in ether at 0° and treated with ethereal hydrochloric acid to give 690 mg. of pale yellow, hygroscopic solid 3,6-dihydro-4-methyl-6-(3-nitrophenyl)-2-thioxo-1,5(2H)-pyrimidinedicarboxylic acid, 5-(1-methylethyl) 1-[2-[methyl(phenylmethyl)amino]ethyl]ester, monohydrochloride; m.p. 80° (vaporizes). TLC (silica gel; ethyl acetate:hexanes, 1:2) $R_f=0.21$.

Anal. calc'd. for $C_{26}H_{30}N_4SO_6 \cdot HCl \cdot 0.7\ H_2O$: C, 54.25; H, 5.50; N, 9.74; S, 5.57; Cl, 6.16. Found: C, 54.25; H, 5.54; N, 9.54; S, 5.49; Cl, 6.00.

EXAMPLE 91

6-(2,3-Dichlorophenyl)-3,6-dihydro-4-methyl-2-thioxo-1,5(2H)-pyrimidinedicarboxylic acid, 5-(1-methylethyl) 1-[2-[methyl(phenylmethyl)amino]ethyl]ester, monohydrochloride a)

6-(2,3-Dichlorophenyl)-2-[[(4-methoxyphenyl)methyl]thio]-4-methyl-1,5(6H)-pyrimidinedicarboxylic acid, 5-(1-methylethyl) 1-[2-[methyl(phenylmethyl)amino]ethyl]ester

Phosgene in benzene (1.3 eq., 8.7 mmole, 6.7 ml. of 1.3M solution) is added dropwise to a solution of 4-(2,3-dichlorophenyl)-1,4-dihydro-2-[[(4-methoxyphenyl)methyl]thio]-6-methyl-5-pyrimidinecarboxylic acid, 1-methylethyl ester (3.2 g., 6.7 mmole) [prepared as set forth in Example 80 (a)] in neat pyridine (13.4 ml.) at room temperature. The suspension is stirred for 40 minutes and then N-benzyl-N-methyl ethanolamine (1.6 eq., 1.74 g., 10.7 mmole) is added dropwise. As the mixture is stirred a solid precipitates out of solution. After stirring overnight, the mixture is diluted with dichloromethane (50 ml.) and washed with sodium bicarbonate (2×30 ml.) and sodium dihydrogen phosphate 2×30 ml.). The organic layer is dried over anhydrous magnesium sulfate, filtered, and stripped to give 4.5 g. of a brown oil. Flash chromatography eluting with ethyl acetate gives 1.26 g. of 6-(2,3-dichlorophenyl)-2-[[(4-methoxyphenyl)methyl]thio]-4-methyl-1,5(6H)-pyrimidinedicarboxylic acid, 5-(1-methylethyl) 1-[2-[methyl(phenylmethyl)amino]ethyl]ester as a pale yellow oil.

b)

6-(2,3-Dichlorophenyl)-3,6-dihydro-4-methyl-2-thioxo-1,5(2H)-pyrimidinedicarboxylic acid, 5-(1-methylethyl) 1-[2-[methyl(phenylmethyl)amino]ethyl]ester, monohydrochloride

Ethanethiol (2 eq., 277.7 μl., 3.76 mmole) is added to a mixture of the ester product from part (a) (1.26 g., 1.88 mmole) in dichloromethane (7.5 ml.) and trifluoroacetic acid (750 μl.) at room temperature under nitrogen. The mixture is stirred for 48 hours, then diluted with dichloromethane (100 ml.) and washed with sodium bicarbonate (2×50 ml.), water (2×50 ml.), and sodium dihydrogen phosphate (2×50 ml.). The organic layer is dried over anhydrous magnesium sulfate, filtered and concentrated in vacuo to give a yellow solid. This solid is dissolved in warm ether (100 ml. on a steam bath) and the hydrochloride salt precipitates out by the addition of ethereal hydrochloric acid. The mixture is cooled to −19° and the pure hydrochloride salt is collected by filtration. The solid is recrystallized twice from ethyl acetate/hexanes to give 701 mg. of pale yellow solid 6-(2,3-dichlorophenyl)-3,6-dihydro- 4-methyl-2-thioxo-1,5(2H)-pyrimidinedicarboxylic acid, 5-(1-methylethyl) 1-[2-[methyl(phenylmethyl)amino]ethyl]ester, monohydrochloride; m.p. 164°-166°. TLC (silica gel; ethyl acetate:hexanes; 1:2 $R_f$=0.33.

Anal. calc'd. for $C_{26}H_{29}Cl_2N_3O_4S \cdot HCl$: C, 53.30; H, 4.99; N, 7.17; S, 5.47; Cl, 18.15. Found: C, 53.41; H, 5.18; N, 7.11; S, 5.44; Cl, 18.13.

EXAMPLE 92

3,6-Dihydro-4-methyl-2-thioxo-6-[2-(trifluoromethyl)phenyl]-1,5(2H)-pyrimidinedicarboxylic acid, 5-ethyl 1-[1-(phenylmethyl)-4-piperidinyl]ester, monohydrochloride a)

2-[[(4-Methoxyphenyl)methyl]thio]-4-methyl-6-[2-(trifluoromethyl)phenyl]-1,5(6H)-pyrimidinedicarboxylic acid, 5-ethyl 1-[1-(phenylmethyl)-4-piperidinyl]ester

A solution of 1,4-dihydro-2-[[(4-methoxyphenyl)methyl]thio]-6-methyl-4-[2-(trifluoromethyl)phenyl]-5-pyrimidinecarboxylic acid, ethyl ester (2.5 g., 5.3 mmole) [prepared as set forth in Example 95 (a)] in pyridine (25 ml.) is treated with phosgene (0.67 g., 6.7 mmole, 12% toluene solution) and heated for one hour at 50° and then treated slowly with a solution of N-benzyl-4-hydroxypiperidine (1.5 g., 7.8 mmole) in pyridine (5 ml.). After heating for 16 hours at 50°, the solution is cooled and partitioned between water and ethyl acetate. The organic phase is washed with water (three times) and brine, then dried and evaporated to give 3.6 g. of a dark oil. This material is combined with 1.6 g. of similarly prepared crude product. Flash chromatography eluting with ethyl acetate:hexanes (1:2) gives 1.3 g. of slightly impure 2-[[(4-methoxyphenyl)methyl]thio]-4-methyl-6-[2-(trifluoromethyl)phenyl]-1,5(6H)-pyrimidinedicarboxylic acid, 5-ethyl 1-[1-(phenylmethyl)-4-piperidinyl]ester. TLC (silica gel; ethyl acetate:hexanes, 1:2) major spot at $R_f$=0.25.

b)

3,6-Dihydro-4-methyl-2-thioxo-6-[2-(trifluoromethyl)phenyl]-1,5(2H)-pyrimidinedicarboxylic acid, 5-ethyl 1-[1-(phenylmethyl)-4-piperidinyl]ester, monohydrochloride

A solution of the ester product from part (a) (1.3 g., 1.9 mmole) in chloroform (25 ml.) is treated with trifluoroacetic acid (0.7 ml., 7.2 mmole) and ethanethiol (0.28 g., 4.2 mmole) and refluxed for 3 hours. The cooled solution is evaporated. The residue is taken up in ethyl acetate and washed with sodium bicarbonate, water and brine, dried, and evaporated to give 1.2 g. of crude oil product. Flash chromatography eluting with ethyl acetate: hexanes:methanol (50:100:3) gives 0.64 g. of 3,6-dihydro-4-methyl-2-thioxo-6-[2-(trifluoromethyl)phenyl]-1,5(2H)-pyrimidinedicarboxylic acid, 5-ethyl 1-[1-(phenylmethyl)-4-piperidinyl]ester as a semi-solid product.

Anal. calc'd. for $C_{28}H_{30}N_3F_3O_4S$: C, 59.88; H, 5.38; N, 7.48. Found C, 59.47; H, 5.40; N, 7.41.

The above material is dissolved in acetonitrile (10 ml.) and treated with 1 eq. of ethanolic hydrochloric acid to slowly crystallize 0.53 g. of yellow solid 3,6-dihydro-4-methyl-2-thioxo-6-[2-(trifluoromethyl)phenyl]-1,5(2H)-pyrimidinedicarboxylic acid, 5-ethyl 1-[1-(phenylmethyl)-4-piperidinyl]ester, monohydrochloride; m.p. 203°-205°. TLC (silica gel; dichloromethane:methanol, 50:1) $R_f$=0.40.

Anal. calc'd. for $C_{28}H_{30}F_3N_3O_4S \cdot HCl$: C, 56.23; H, 5.22; N, 7.02; Cl, 5.92; S, 5.36. Found: C, 56.35; H, 5.21; N, 7.47; Cl, 6.01; S, 5.36.

EXAMPLE 93

3,6-Dihydro-4-methyl-6-(2,1,3-benzoxadiazol-4-yl)-2-thioxo-1,5(2H)-pyrimidinedicarboxylic acid, diethyl ester a)

1,4-Dihydro-2-[[(4-methoxyphenyl)methyl]thio]-6-methyl-4-(2,1,3-benzoxadiazol-4-yl)-5-pyrimidinecarboxylic acid, ethyl ester A mixture of 2-[(2,1,3-benzoxadiazol-4-yl)methylene]-3-oxobutanoic acid, ethyl ester (2.38 g., 9.15 mmole) and S-(4-methoxyphenyl)thiopseudourea, hydrochloride (2.13 g., 9.15 mmole) in dry dimethylformamide (15 ml.) under argon at room temperature is treated with sodium acetate (0.73 g., 9.15 mmole) and heated at 80° for 3 hours. The mixture is diluted with ether and washed with water (twice) and saturated brine. The organic fraction is dried over anhydrous magnesium sulfate and concentrated in vacuo to give 3.56 g. of crude product. Flash chromatography eluting with ethyl acetate:hexanes (4:7) gives 2.36 g. of 1,4-dihydro-2-[[(4-methoxyphenyl)methyl]thio]-6-methyl-4-(2,1,3-benzoxadiazol-4-yl)-5-pyrimidinecarboxylic acid, ethyl ester as an oil. TLC (silica gel; ethyl acetate:hexanes, 1:1) $R_f=0.45$.

b)

2-[[(4-Methoxyphenyl)methyl]thio]-4-methyl-6-(2,1,3-benzoxadiazol-4-yl)-1,5(6H)-pyrimidinedicarboxylic acid, diethyl ester The ethyl ester product from part (a)(1.02 g., 2.32 mmole) in dry dichloromethane (10 ml.) under argon at 0°–5° is treated with pyridine (1 ml.) followed by ethyl chloroformate (0.30 ml., 340 mg., 3.13 mmole). After 30 minutes, the cooling bath is removed and the mixture is allowed to stir at room temperature for one hour. Volatiles are stripped in vacuo and the residue is dissolved in ethyl acetate and washed with sodium bicarbonate, water, and brine. The organic fraction is dried over anhydrous magnesium sulfate and concentrated in vacuo to give 1.22 g. of crude product. Flash chromatography eluting with ethyl acetate:hexanes (1:3) gives 0.94 g. of an oil. Crystallization from isopropyl ether/hexanes gives 0.82 g. of 2-[[(4-methoxyphenyl)methyl]thio]-4-methyl-6-(2,1,3-benzoxadiazol-4-yl)-1,5(6H)-pyrimidinedicarboxylic acid, diethyl ester; m.p. 94°–96°. TLC (silica gel;ethyl acetate:hexanes, 1:1) $R_f=0.56$.

Anal. calc'd. for $C_{25}H_{26}N_4O_6S$: C, 58.81; H, 5.13; N, 10.97; S, 6.2. Found: C, 58.86; H, 5.14; N, 10.94; S, 6.1.

c)

3,6-Dihydro-4-methyl-6-(2,1,3-benzoxadiazol-4-yl)-2-thioxo-1,5(2H)-pyrimidinedicarboxylic acid, diethyl ester A solution of the diethyl ester from part (b) (0.82 g., 1.6 mmole) in dry dichloromethane (10 ml.) under argon at 0°–5° is treated with trifluoroacetic acid (0.37 ml., 0.55 g., 4.8 mmole) and ethanethiol (0.24 ml., 0.20 g., 3.2 mmole). The mixture is heated at reflux temperature overnight. Volatiles are stripped in vacuo and the residue is dissolved in warm isopropyl ether, diluted to the cloud point with hexane, and allowed to stand to give 0.58 g. of 3,6-dihydro-4-methyl-6-(2,1,3-benzoxadiazol-4-yl)-2-thioxo-1,5(2H)-pyrimidinedicarboxylic acid, diethyl ester as a yellow solid; m.p. 144°–146°. TLC (silica gel; ethyl acetate:hexanes, 1:1) $R_f=0.53$.

Anal. calc'd. for $C_{17}H_{18}N_4O_5S$: C, 52.30; H, 4.65; N, 14.35; S, 8.21 Found: C, 52.44; H, 4.58; N, 14.41; S, 8.14.

EXAMPLE 94

3,6-Dihydro-4-methyl-6-(2-nitrophenyl)-2-thioxo-1,5(2H)-pyrimidinedicarboxylic acid, 5-ethyl 1-[1-(phenylmethyl)-4-piperidinyl]ester, monohydrochloride a.

1,4-Dihydro-2-[[(4-methoxyphenyl)methyl]thio]-6-methyl-4-(2-nitrophenyl)-5-pyrimidinecarboxylic acid, ethyl ester A mixture of 2-[(2-nitrophenyl)methylene]-3-oxobutanoic acid, ethyl ester (6.0 g., 22 mmole), S-(4-methoxybenzyl) thiopseudourea, hydrochloride (5.3 g., 22 mmole) and sodium bicarbonate (1.9 g., 22 mmole) in dimethylformamide (60 ml.) is stirred and heated for 4 hours at 70°, then cooled and diluted with ethyl acetate. After washing with water (twice) and brine, the solution is dried and evaporated in vacuo to give 11.0 g. of crude product.

A solution of the above crude product in acetonitrile (50 ml.) is treated with a solution of oxalic acid (2.2 g.) in acetonitrile (20 ml.). A slow crystallization gives 8.2 g. of cream colored oxalate salt; m.p. 130°–132°. This salt is treated with sodium hydroxide in ethyl acetate to give 7.3 g. of 1,4-dihydro-2-[[(4-methoxyphenyl)methyl]thio]-6-methyl-4-(2-nitrophenyl)-5-pyrimidinecarboxylic acid, ethyl ester.

Anal. calc'd. for $C_{22}H_{23}N_3O_5S$: C, 59.85; H, 5.25; N, 9.51. Found: C, 59.50; H, 5.28; N, 9.35.

b.

2-[[(4-Methoxyphenyl)methyl]thio]-4-methyl-6-(2-nitrophenyl)-1,5(6H)-pyrimidinedicarboxylic acid, 5-ethyl 1-[1-(phenylmethyl)-4-piperidinyl]ester A solution of the product from part (a) (3.2 g., 7.2 mmole) in acetonitrile (50 ml.) and pyridine (35 ml.) is treated dropwise with phosgene (1.4 g., 14.4 mmole, 11.2 ml. of 12.5% solution in toluene), and then stirred for 4 hours at room temperature. A solution of N-benzyl-4-hydroxypiperidine, hydrochloride salt (5.1 g., 26 mmole) in acetonitrile (20 ml.) is slowly added and the solution is stirred for 16 hours at room temperature. Water (10 ml.) is added and the solvent is evaporated in vacuo to give an oil which is partitioned between ethyl acetate and 1N hydrochloric acid. The organic layer is washed with sodium bicarbonate solution, water, and brine, then dried and evaporated to give 4.0 g. of crude 2-[[(4-methoxyphenyl)methyl]thio]-4-methyl-6-(2-nitrophenyl)-1,5(6H)-pyrimidinedicarboxylic acid, 5-ethyl 1-[1-(phenylmethyl)-4-piperidinyl]ester as a semi-solid.

c.

3,6-Dihydro-4-methyl-6-(2-nitrophenyl)-2-thioxo-1,5(2H)-pyrimidinedicarboxylic acid, 5-ethyl 1-[1-(phenylmethyl)-4-piperidinyl]ester, monohydrochloride A solution of the crude product from part (b) (3.0 g., 4.5 mmole), trifluoroacetic acid (2.1 ml., 26.8 mmole) and ethanethiol (0.84 g., 13.4 mmole) in dichloromethane (50 ml.) is stirred at room temperature for 16 hours. The solvent is evaporated and the residue is taken up in ethyl acetate and washed with sodium bicarbonate solution, water, and brine, then dried, and evaporated in vacuo to give 3.45 g. of a crude oil product. The material is combined with 0.65 g. of similarly prepared product and then flash chromatographed using ethyl acetate/hexane (1:1) to give 2.5 g. of 3,6-dihydro-4-methyl-6-(2-nitrophenyl)-2-thioxo-1,5(2H)-pyrimidinedicarboxylic acid,5-ethyl 1-[1-(phenylmethyl)-4-piperidinyl]ester as a glass-like solid. TLC (silica gel; ethyl acetate:hexane, 1:1) $R_f$=0.25.

Anal. calc'd for $C_{27}H_{30}N_4O_6S$: C, 60.20; H, 5.61: N, 10.40. Found: C, 60.09; H, 5.68; N, 10.23.

The above product is dissolved in acetonitrile (40 ml.) and treated with 1 eq. of methanolic hydrochloric acid. The solution is concentrated to approximately one-half volume to initiate cyrstallization of 2.25 g. of 3,6-dihydro-4-methyl-6-(2-nitrophenyl)-2-thioxo-1,5-(2H)-pyrimidinedicarboxylic acid, 5-ethyl 1-[1-(phenylmethyl)-4-piperidinyl]ester, monohydrochloride as a yellow product; m.p. 203°-205° (dec.).

Anal. Calc'd for $C_{27}H_{30}N_4O_6S\cdot HCl\cdot 0.25C_2H_3N$ C, 56.42; H, 5.47; N, 10.17; Cl, 6.06; S, 5.48. Found: C, 56.56; H, 5.54; N, 10.25; Cl, 6.06; S, 5.32.

EXAMPLE 95

3,6-Dihydro-4-methyl-6-2-(trifluoromethyl)phenyl]-1,5(2H)-pyrimidinedicarboxylic acid, 5-ethyl 1-[1-(phenylmethyl)-3(S)-pyrrolidinyl]ester, monohydrochloride a.

1,4-Dihydro-2-[[(4-methoxyphenyl)methyl]thio]-6-methyl-4-[2-(trifluoromethyl)phenyl]-5-pyrimidinecarboxylic acid, ethyl ester A mixture of 2-[[2-(trifluoromethyl)phenyl]methylene]-3-oxobutanoic acid, ethyl ester (12 g., 42 mmole), S-(4-methoxybenzyl) thiopseudourea, hydrochloride (9.7 g., 42 mmole) and sodium acetate (3.4 g., 42 mmole) in dimethylformamide (75 ml.) is stirred and heated at 70° for 4 hours. The cooled solution is diluted with ether and washed with sodium bicarbonate, water, and brine. The dried solution is evaporated to give 18.6 g. of crude 1,4-dihydro-2-[[(4-methoxyphenyl)methyl]thio]-6-methyl-4-[2-(trifluoromethyl)phenyl]-5-pyrimidinecarboxylic acid, ethyl ester as a viscous oil.

b.

2-[[(4-Methoxyphenyl)methyl]thio]-4-methyl-6-[-2-(trifluoromethyl)phenyl]-1,5(6H)-pyrimidinedicarboxylic acid, 5-ethyl 1-[1-(phenylmethyl)-3(S)-pyrrolidinyl]ester A solution of the product from part (a) (1.4 g., 3.0 mmole) in acetonitrile (10 ml.) and pyridine (5 ml.) under argon at room temperature is treated with a solution of phosgene in toluene (4.5 ml., 5.6 mmole, 12.5% solution). After 2 hours, a solution of (S)-1-benzyl-3-pyrrolidinol (1.05 g., 5.9 mmole) as the hydrochloride salt in acetonitrile (3 ml.) is added. The mixture is allowed to stir for 48 hours. The volatiles are removed in vacuo and the residue is dissolved in ethyl acetate, washed with saturated sodium bicarbonate solution and saturated brine. The organic fraction is dried (MgSO4) and concentrated in vacuo to give 2.6 g. of a dark viscous oil. Flash chromatography on silica gel (LPS-1) eluting with ethyl acetate/hexane (1:4) gives 0.76 g. of 2-[[(4-methoxyphenyl)methyl]thio]-4-methyl-6-[2-(trifluoromethyl)phenyl-1,5(6H)-pyrimidinedicarboxylic acid, 5-ethyl 1-[1-(phenylmethyl)-3(S)-pyrrolidinyl]-ester.

Anal. calc'd. for $C_{35}H_{36}F_3N_3O_5S\cdot 0.56H_2O$: C, 62.01; H, 5.52; N, 6.20. Found C, 62.18; H, 5.22; N, 6.06.

c.

3,6-Dihydro-4-methyl-6-[2-(trifluoromethyl)phenyl]-1,5(2H)-pyrimidinedicarboxylic acid, 5-ethyl 1-[1-(phenylmethyl)-3(S)-pyrrolidinyl]ester, monohydrochloride A solution of the product from part (b) (0.75 g., 1.12 mmole) in dichloromethane (10 ml.) is treated with ethanethiol (0.17 ml., 0.145 g., 2.29 mmole) and trifluoroacetic acid (0.26 ml., 0.385 g., 3.37 mmole) and the mixture is heated at reflux temperature for 10 hours. The volatiles are removed in vacuo and the residue is dissolved in ethyl acetate, and washed with saturated sodium bicarbonate solution and brine. The organic fraction is dried (MgSO4) and concentrated in vacuo to give 0.75 g. of crude product. Flash chromatography on silica gel (LPS-1) eluting with ethyl acetate/hexane (1 l. of 3:7 and 1 l. of 1:2) gives 0.504 g. of 3,6-dihydro-4-methyl-6-[2-(trifluoromethyl)phenyl]-1,5(2H)-pyrimidinedicarboxylic acid, 5-ethyl 1-[1-(phenylmethyl)-3(S)-pyrrolidinyl]ester.

Anal. calc'd for $C_{27}H_{28}F_3N_3O_4S$: C, 59.44; H, 5.17; N, 7.70. Found: C, 59,04; H, 5.41; N, 7.48.

A solution of this product (220 mg., 0.40 mmole) in ether is treated with 0.5N ethereal hydrochloric acid (1 ml.) to precipitate 3,6-dihydro-4-methyl-6-[2-(trifluoromethyl)phenyl]-1,5(2H)-pyrimidinedicarboxylic acid, 5-ethyl 1-[1-(phenylmethyl)-3(S)-pyrrolidinyl]-ester, monohydrochloride; m.p. 115°-125° (foam).

Anal. calc'd for $C_{27}H_{29}ClF_3N_3O_4S\cdot 3.11H_2O$: C, 55.71; H, 5.20;N, 7.22; S, 5.51; Cl, 6.09. Found: C, 55.50; H. 5.69;N, 6.89; S, 5.56; Cl, 6.12.

EXAMPLES 96–118

Following the procedures of Examples 55 to and 89 to 95, the 2-(4-methoxybenzyl)thio substituted 1,4-dihydro 5-pyrimidinecarboxylic acid ester shown below in Col. I is reacted to give the corresponding 1,5(6H)-pyrimidinedicarboxylic acid diester shown in Col. II followed by treatment with trifluoroacetic acid to give the 2-thioxo-1,5(2H)-pyrimidinedicarboxylic acid ester product shown in Col. III.

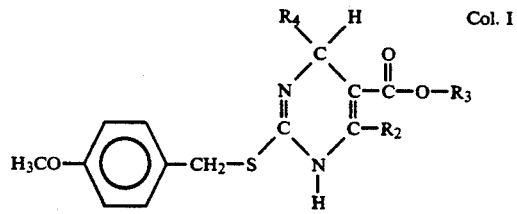

Col. I

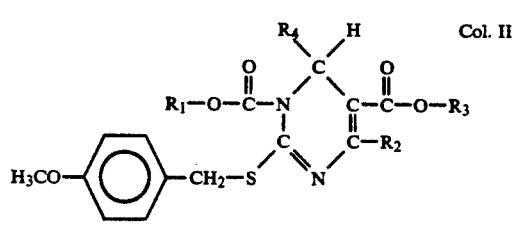

Col. II

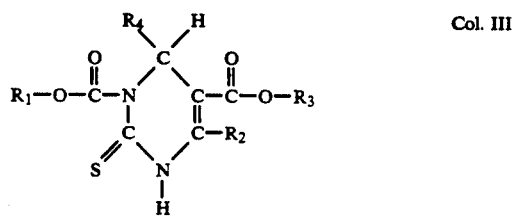

Col. III

| Example | R₃ | R₂ | R₄ | R₁ |
|---|---|---|---|---|
| 96 | —CH₂—C₆H₅ | —CH₃ | 2-thienyl | —CH₂—C₆H₅ |
| 97 | —CH₂—C₆H₁₁ | —C₂H₅ | 3-pyridyl | —CH₂—C₆H₁₁ |
| 98 | —(CH₂)₂—(2-pyridyl) | —CH₃ | 2-NO₂-C₆H₄ | —(CH₂)₂—(2-pyridyl) |
| 99 | —(CH₂)₂—O—CH₃ | —CH₃ | 2-CF₃-C₆H₄ | —(CH₂)₂—O—CH₃ |
| 100 | —(CH₂)₂—O—C₆H₅ | —CH₃ | 2-NO₂-3-Cl-C₆H₃ | —(CH₂)₂—O—C₆H₅ |
| 101 | —(CH₂)₂—S—C₂H₅ | —CH₃ | 2,3-Cl₂-C₆H₃ | —(CH₂)₂—S—C₂H₅ |
| 102 | —CH(CH₃)₂ | —CH₂—C₆H₅ | 2-NO₂-C₆H₄ | —(CH₂)₂—N(CH₃)₂ |

-continued

| Example | R₃ | R₂ | R₄ | R₁ |
|---|---|---|---|---|
| 103 | —CH(CH₃)₂ | —CH₃ | 2,3-difluorophenyl | —(CH₂)₂—N(piperazinyl)-N-phenyl |
| 104 | —CH(CH₃)₂ | —CH₃ | pyridyl | —CH₂—C(O)—N(morpholino) |
| 105 | —(CH₂)₂—O—C(O)—C₂H₅ | —CH₃ | 2-nitrophenyl | —(CH₂)₂—O—C(O)—C₂H₅ |
| 106 | —(CH₂)₂—O—C(O)—CH₂-phenyl | —CH₃ | 1-(trifluoromethyl)naphthyl | —C₂H₅ |
| 107 | —(CH₂)₂—O—C(O)—C₂H₅ | —CH₃ | 2,3-dichlorophenyl | —(CH₂)₂—O—C(O)—C₂H₅ |
| 108 | —C₂H₅ | —CH₃ | 1-benzylimidazolyl | —C₂H₅ |

-continued

| Example | R₃ | R₂ | R₄ | R₁ |
|---|---|---|---|---|
| 109 | —C₂H₅ | —CH₃ | N-benzylindole (4-yl) | —C₂H₅ |
| 110 | —CH₃ | —CH₃ | isoquinolin-like (benzo-fused pyridine with CH=N) | —CH(CH₃)₂ |
| 111 | —C₂H₅ | —CH₃ | quinolin-8-yl | —C₂H₅ |
| 112 | —(CH₂)₂—O—C₂H₅ | —CF₃ | isoquinolinyl | —(CH₂)₂—O—C₂H₅ |
| 113 | —(CH₂)₂—N(CH₃)₂ | —CH₃ | benzothiazolyl | —C₂H₅ |
| 114 | —C₂H₅ | —CH₃ | benzoxazolyl | —C₂H₅ |

-continued

| Example | R₃ | R₂ | R₄ | R₁ |
|---|---|---|---|---|
| 115 | —CH₂CCl₃ | —CH₃ | 2-(N-benzylideneamino)phenyl | —C₂H₅ |
| 116 | —C₂H₅ | —CH₃ | 2-(triazenyl)phenyl (ArNH—N=N) | —C₂H₅ |
| 117 | —C₂H₅ | —CH₃ | 1-naphthyl | —CH(CH₃)₂ |
| 118 | —CH(CH₃)₂ | —CH₃ | phenyl | 1-benzyl-4-piperidinyl |

The N-protecting group shown in Examples 108, 109, and 115 are removed as the last step in the synthesis.

EXAMPLE 119

(−)-3,6-Dihydro-4-methyl-6-(3-nitrophenyl)-2-thioxo-1,5(2H)-pyrimidinedicarboxylic acid, 5-methyl 1-(1-methylethyl) ester a)

2-[[1(4-(Methoxyphenyl)methyl]thio]-4-methyl-6-(3-nitrophenyl-1,5(6H)-pyrimidinedicarboxylic acid, 5-methyl 1-[(S)-1-[(1,1-dimethylethoxy)carbonyl]-5-(methoxycarbonyl)-3-pyrrolidinyl]ester A solution of phosgene in benzene (1.3M, 10.8 ml., 14.1 mmole) is added dropwise to a mixture of 1,4-dihydro-2-[[(4-methoxyphenyl)methyl]thio]-6-methyl-4-(3-nitrophenyl)-5-pyrimidinecarboxylic acid, methyl ester (4.63 g., 10.8 mmole) in neat pyridine (25 ml.) at room temperature under nitrogen and allowed to stir for one hour. A solution of 1-[(1,1-dimethylethoxy)carbonyl]-4-(trans-hydroxy)-L-proline, methyl ester (4.2 g., 1.6 eq., 17.3 mmole) in pyridine (10 ml.) is added to the mixture and allowed to stir overnight. The mixture is diluted with ethyl acetate (100 ml.) and washed with water (2×75 ml.), sodium bicarbonate (2×75 ml.), sodium dihydrogen phosphate (2×75 ml.), and water (75 ml.). The organic layer is dried over anhydrous magnesium sulfate, filtered, and stripped. Flash chromatography eluting with ethyl acetate:hexanes (1:2) gives 4.88 g. of 2-[[(4-methoxyphenyl)methyl]thio-4-methyl-6-(3-nitrophenyl)-1,5(6H)-pyrimidinedicarboxylic acid, 5-methyl 1-[(S)-1-[(1,1-dimethylethoxy)carbonyl]-5-(methoxycarbonyl)-3-pyrrolidinyl]ester as a yellow foam.

b)

(−)-1,2,3,4-Tetrahydro-6-methyl-4-(3-nitrophenyl)-2-thioxo-5-pyrimidinecarboxylic acid, methyl ester The ester product from part (a) (3.47 g., 4.97 mmole) is added to a mixture of trifluoroacetic acid (10 ml.) and anisole (10% by volume, 100 μl.) at 0° under nitrogen. After 2 hours the trifluoroacetic acid is removed in vacuo. The residue is dissolved in dichloromethane (30 ml.), washed with sodium bicarbonate (2×15 ml.), dried over anhydrous magnesium sulfate, filtered, and immediately absorbed onto Celite and flash chromatographed (600 g. LPS-1 silica gel) eluting with ethyl acetate:hexanes:methanol (80:20:1) to give 3,6-dihydro-4-methyl-6-(3-nitrophenyl)-2-thioxo-1,5(2H)-pyrimidinedicarboxylic acid, 5-methyl 1-[(S)-5-(methoxycarbonyl)-3-pyrrolidinyl] ester, isomer A; TLC (silica gel; ethyl acetate: hexanes:methanol; 80:20:1) $R_f=0.37$ and isomer B; TLC (silica gel; ethyl acetate:hexanes:methanol, 80:20:1) $R_f=0.25$.

The isomer A product is hydrolyzed in sodium methoxide (2 eq., 0.8 ml., 3.5 ml.) and methanol (3 ml.) overnight at room temperature. The suspension is acidified with ether/hydrochloric acid to give 567.2 mg. of (−)-1,2,3,4-tetrahydro-6-methyl-4-(3-nitrophenyl)-2-thioxo-5-pyrimidinecarboxylic acid, methyl ester as a white crystalline solid. TLC (silica gel; ethyl acetate:hexanes, 1:2) $R_f=0.23$; $[\alpha]_{589}^{20}=-28.8°$ (c=0.5, dimethylsulfoxide).

c)

(−)-3,6-Dihydro-4-methyl-6-(3-nitrophenyl)-2-thioxo-1,5(2H)-pyrimidinedicarboxylic acid, 5-methyl 1-(1-methylethyl) ester Bis(trimethylsilyl)trifluoroacetamide (1 eq., 425 μl., 1.6 mmole) is added to a mixture of (−)-1,2,3,4-tetrahydro-6-methyl-4-(3-nitrophenyl)-2-thioxo-5-pyrimidinecarboxylic acid, methyl ester (501 mg., 1.6 mmole) in neat pyridine (3.2 ml.) at 0° under nitrogen. The mixture is stirred for 30 minutes at 0° and isopropyl chloroformate (1 eq., 182 μl., 1.6 mmole) is added. The mixture is stirred to room temperature overnight. After diluting with ethyl acetate (30 ml.), the mixture is washed with 1N hydrochloric acid (2×10 ml.) and sodium bicarbonate (2×10 ml.), dried over anhydrous magnesium sulfate, filtered, and stripped to give a brown oil. Flash chromatography (60 g. LPS-1 silica gel) eluting with ethyl acetate: hexanes (1:4) gives a pale yellow oil which crystallizes upon standing. Recrystallization from ethyl acetate:hexane (1:3) gives 120.4 mg. of solid (−)-3,6-dihydro-4-methyl-6-(3-nitrophenyl)-2-thioxo-1,5(2H)-pyrimidinedicarboxylic acid, 5-methyl 1-(1-methylethyl) ester; m.p. 157°–158°; $[\alpha]_{589}^{20}=-54.7$ (c=1, CDCl₃) TLC (silica gel; ethyl aceate:hexanes, 1:2) $R_f=0.47$.

Anal. calc'd. for $C_{17}H_{19}N_3O_6S$: C, 51.90; H, 4.86;N, 10.68; S, 8.15. Found: C, 51.67; H, 4.72;N, 10.29; S, 7.92.

EXAMPLE 120

(+)-3,6-Dihydro-4-methyl-6-(3-nitrophenyl)-2-thioxo-1,5(2H)-pyrimidinedicarboxylic acid, 5-methyl 1-(1-methylethyl) ester a)

(+)-1,2,3,4-Tetrahydro-6-methyl-4-(3-nitrophenyl)-2-thioxo-5-pyrimidinecarboxylic acid, methyl ester 3,6-Dihydro-4-methyl-6-(3-nitrophenyl)-2-thioxo-1,5(2H)-pyrimidinedicarboxylic acid, 5-methyl 1-[(S)-5-(methoxycarbonyl)-3-pyrrolidinyl]ester, isomer B (1.12 g., from Example 115 (b)) is dissolved in methanol (2 ml.) and treated with 4.37M sodium methoxide in methanol (2 eq., 1.1 ml.) and stirred overnight. The mixture is acidified with ether/hydrochloric acid and a very fine precipitate is filtered off. The mother liquor is diluted with ether and cooled overnight. The pure product is obtained by suction filtration of the granular crystals to give 300.6 mg. of (+)-1,2,3,4-tetrahydro-6-methyl-4-(3-nitrophenyl)-2-thioxo-5-pyrimidinecarboxylic acid, methyl ester; $[\alpha]_{589}^{20}=+28.3°$ (c =0.5, dimethylsulfoxide).

b)

(+)-3,6-Dihydro-4-methyl-6-(3-nitrophenyl)-2-thioxo-1,5(2H)-pyrimidinedicarboxylic acid, 5-methyl 1-(1-methylethyl) ester Bis(trimethylsilyl)trifluoroacetamide (1 eq., 199 μl., 0.75 mmole) is added to a mixture of (+)-1,2,3,4-tetrahydro-6-methyl-4-(3-nitrophenyl)-2-thioxo-5-pyrimidinecarboxylic acid, methyl ester (230 mg., 0.75 mmole) in neat pyridine (1.5 ml.) at 0° under nitrogen and stirred for 30 minutes. Isopropyl chloroformate (1 eq., 85.4 μl., 0.75 mmole) is added dropwise to the mixture at 0° and the reaction is stirred at room temperature overnight. After diluting with ethyl acetate (20 ml.), the mixture is washed with 1N hydrochloric acid (2×10 ml.) and sodium bicarbonate (2×10 ml.), dried over anhydrous magnesium sulfate, filtered, and stripped in vacuo. Flash chromatography (LPS-1 silica gel; eluting with ethyl acetate:hexanes) gives 149.7 mg. of crude product. This product is recrystallized from ethyl acetate:hexanes (1:3). A yellow solid is filtered off and the mother liquor is reduced in vacuo and the solid is triturated with ethyl acetate:hexanes (1:3) to give 78.1 mg. of solid (+)-3,6-dihydro-4-methyl-6-(3-nitrophenyl)-2- thioxo-1,5(2H)-pyrimidinedicarboxylic acid, 5-methyl 1-(1-methylethyl) ester; m.p. 155.5°–157°; $[\alpha]_{589}^{20}=+56.7$ (c=1, CDCl$_3$) TLC (silica gel; ethyl acetate: hexanes, 1:2) R$_f$=0.33.

Anal. calc'd. for C$_{17}$H$_{19}$N$_3$O$_6$S: C, 51;90; H, 4.86;N, 10.68; S, 8.15. Found: C, 51.84; H, 4.84;N, 10.60; S, 7.94.

EXAMPLE 121

(−)-3,6-Dihydro-4-methyl-6-(3-nitrophenyl)-2-thioxo-1,5(2H)-pyrimidinedicarboxylic acid, bis(1-methylethyl) ester a)

2-[[(4-Methoxyphenyl)methyl]thio]-4-methyl-6-(3-nitrophenyl)-1,5(6H)-pyrimidinedicarboxylic acid, 5-(1-methylethyl) 1-[(S)-1-[(1,1-dimethylethoxy)carbonyl]-5-(methoxycarbonyl)-3-pyrrolidinyl]ester A solution of phosgene in benzene (1.3M, 1.3 eq., 21.9 ml.) is added dropwise to a mixture of 1,4-dihydro-2-[[(4-methoxyphenyl)methyl]thio]-6-methyl-4-(3-nitrophenyl)-5-pyrimidinecarboxylic acid, 1-methylethyl ester (10.0 g., 22 mmole) in neat pyridine (44 ml.) at room temperature under nitrogen and allowed to stir for one hour. A solution of 1-[(1,1-dimethylethoxy)carbonyl]-4-(trans-hydroxy)-L-proline, methyl ester (8.6 g., 1.6 eq., 35.2 mmole) in neat benzene (20 ml.) is added dropwise and the mixture is allowed to stir at room temperature for 48 hours. The mixture is then diluted with ethyl acetate (100 ml.) and washed with sodium bicarbonate (2×100 ml.), sodium dihydrogen phosphate (2×100 ml.), and brine. The organic layer is dried over anhydrous magnesium sulfate, filtered, and reduced in vacuo to give a brown oil. Flash chromatography eluting with ethyl acetate:hexane (1:2) gives 5.23 g. of 2-[[(4-methoxyphenyl)methyl]thio]-4-methyl-6-(3-nitrophenyl)-1,5(6H)-pyrimidinedicarboxylic acid, 5-(1-methylethyl) 1-[(S)-1-[(1,1-dimethylethoxy)carbonyl]-5-(methoxycarbonyl)-3-pyrrolidinyl]ester as a yellow oil.

b)

(−)-1,2,3,4-Tetrahydro-6-methyl-4-(3-nitrophenyl)-2-thioxo-5-pyrimidinecarboxylic acid, 1-methylethyl ester A solution of the ester product from part (a) (4.45 g., 6.12 mmole) in dry dichloromethane (5 ml.) is added dropwise to a solution of trifluoroacetic acid (12 ml.) and anisole (1.2 ml.) at 0° under nitrogen. After 2.5 hours, the trifluoroacetic acid is stripped in vacuo and the residue is dissolved in dichloromethane. The organic layer is washed with sodium bicarbonate (15 ml.), dried over anhydrous magnesium sulfate, filtered, and stripped. The crude product is immediately flash chromatographed (600 g. LPS-1 silica gel) eluting with ethyl acetate:hexane:methanol (80:20:1) to give 3,6-dihydro-4-methyl-6-(3-nitrophenyl)-2-thioxo-1,5(2H)-pyrimidinedicarboxylic acid, 5-(1-methylethyl) 1-[(S)-5-(methoxycarbonyl)-3-pyrrolidinyl]ester, isomer A and isomer B as yellow oils.

The isomer A product is hydrolyzed in sodium methoxide (0.64 ml., 6.12 mmole) and methanol (5 ml.) overnight. The mixture is acidified with ether/hydrochloric acid at 0° with stirring and then stripped in vacuo. The resulting gum is triturated with cold methanol, filtered, and washed to give 584.6 mg. of (−)-1,2,3,4-tetrahydro-6-methyl-4-(3-nitrophenyl)-2-thioxo-5-pyrimidinecarboxylic acid, 1-methylethyl ester as a beige solid; m.p. greater than 250°.

c)

(−)-3,6-Dihydro-4-methyl-6-(3-nitrophenyl)-2-thioxo-1,5(2H)-pyrimidinedicarboxylic acid, bis(1-methylethyl) ester Bis(trimethylsilyl)trifluoroacetamide (1.1 eq., 436 μl., 1.6 mmole) is added to a solution of (−)-1,2,3,4-tetrahydro-6-methyl-4-(3-nitrophenyl)-2-thioxo-5-pyrimidinecarboxylic acid, 1-methylethyl ester (1.49 mmole) in pyridine (2.98 ml.) and dry tetrahydrofuran (2.98 mmole) at 0° under nitrogen. The mixture is stirred at 0° for one hour and then the temperature is reduced to −78° (dry ice/acetone). A solution of isopropyl chloroformate (1.1 eq., 182 μl., 1.6 mmole) in dry tetrahydrofuran (1 ml.) is added dropwise and the mixture is stirred to room temperature overnight. The mixture is diluted with ethyl acetate (20 ml.) and washed with 1N hydrochloric acid (2×10 ml.) and sodium bicarbonate (2×10 ml.). The organic layer is dried over anhydrous magnesium sulfate, filtered, and reduced in vacuo to an oil. Flash chromatography (50 g. LPS-1 silica gel) eluting with ethyl acetate:hexanes (1:4) gives both mono and diacylated products. The fractions of monoacylated product (R$_f$=0.48) are reduced in vacuo to give 272.9 mg. of crystalline solid. Recrystallization from ethyl acetate:hexanes gives 205.2 mg. of (−)-3,6-dihydro-4-methyl-6-(3-nitrophenyl)-2-thioxo-1,5(2H)-pyrimidinedicarboxylic acid, bis(1-methylethyl) ester as a yellow solid; m.p. 146°–148°; $[\alpha]_{589}^{20}=-71.4°$ (c=1.05, CDCl$_3$) TLC (silica gel; ethyl acetate:hexanes) R$_f$=0.48.

Anal calc'd. for C$_{19}$H$_{23}$N$_3$O$_6$S: C, 54.15; H, 5.50;N, 9.97; S, 7.61. Found: C, 54.00; H, 5.44;N, 9.94; S, 7.36.

EXAMPLE 122

(+)-3,6-Dihydro-4-methyl-6-(3-nitrophenyl)-2-thioxo-1,5(2H)-pyrimidinedicarboxylic acid, bis(1-methylethyl) ester a)

(+)-1,2,3,4-Tetrahydro-6-methyl-4-(3-nitrophenyl)-2-thioxo-5-pyrimidinecarboxylic acid, 1-methylethyl ester 3,6-Dihydro-4-methyl-6-(3-nitrophenyl)-2-thioxo-1,5(2H)-pyrimidinedicarboxylic acid, 5-(1-methylethyl) 1-[(S)-5-(methoxycarbonyl)-3-pyrrolidinyl]ester, isomer B [from Example 121 (b)] is hydrolyzed in sodium methoxide and methanol according to the procedure of Example 121 (b) to give (+)-1,2,3,4-tetrahydro-6-methyl-4-(3-nitrophenyl)-2-thioxo-5-pyrimidinecarboxylic acid, 1-methylethyl ester.

b)

(+)-3,6-Dihydro-4-methyl-6-(3-nitrophenyl)-2-thioxo-1,5(2H)-pyrimidinedicarboxylic acid, bis (1-methylethyl) ester Bis(trimethylsilyl)trifluoroacetamide (1.1 eq., 260 μl., 0.98 mmole) is added to a solution of (+)-1,2,3,4-tetrahydro-6-methyl-4-(3-nitrophenyl)-2-thioxo-5-pyrimidinecarboxylic acid, 1-methylethyl ester (0.89 mmole) in pyridine (2 ml.) and tetrahydrofuran (2 ml.) at 0° under nitrogen. After one hour the temperature is lowered to −78° (dry ice/acetone), and a solution of isopropyl chloroformate (1.1 eq., 112 μl.) in tetrahydrofuran (1 ml.) is added dropwise. The mixture is stirred at room temperature overnight. The mixture is diluted with ethyl acetate (10 ml.) and washed wtih 1N hydrochloric acid (2×5 ml.) and sodium bicarbonate (2×5 ml.). The organic layer is dried over anhydrous magnesium sulfate, filtered, and dried to give a brown oil. Flash chromatography (35 g. LPS-silica gel) eluting with ethyl acetate:hexanes (1:4) gives the monoacylated product ($R_f=0.5$) as a yellow solid. Recrystallization from ethyl acetate:hexanes yields 93 mg. of (+)-3,6-dihydro-4-methyl-6-(3-nitrophenyl)-2-thioxo-1,5(2H)-pyrimidinedicarboxylic acid, bis (1-methylethyl) ester as a yellow crystalline solid; m.p. 146°-148°; $[\alpha]_{589}^{20}=+68.5°$ (c=1, CDCl$_3$) TLC (silica gel; ethyl acetate:hexanes, 1:2) $R_f=0.5$.

Anal. calc'd. for C$_{19}$H$_{23}$N$_3$O$_6$S: C, 54.15; H, 5.50;N, 9.97; S, 7.61. Found: C, 54.14; H, 5.57;N, 9.94; S, 7.39.

EXAMPLE 123

(−)-3,6-Dihydro-4-methyl-6-(3-nitrophenyl)-2-thioxo-1,5(2H)-pyrimidinedicarboxylic acid, 1-ethyl 5-(1-methylethyl) ester Bis(trimethylsilyl)trifluoroacetamide (2.1 eq., 1.5 ml., 5.64 mmole) is added to a mixture of (−)-1,2,3,4-tetrahydro-6-methyl-4-(3-nitrophenyl)-2-thioxo-5-pyrimidinecarboxylic acid, 1-methylethyl ester (900 mg., 2.68 mmole) in dry tetrahydrofuran (5 ml.) and pyridine (5 ml.) at 0° under nitrogen. After stirring for one hour the bath temperature is lowered to −78° (dry ice/acetone), and a solution of ethyl chloroformate (2.1 eq., 0.54 ml., 5.64 mmole) in tetrahydrofuran (1 ml.) is added dropwise with stirring. The mixture is then brought to room temperature and stirred for 2 hours. The mixture is then diluted with ethyl acetate (25 ml.) and washed with sodium bicarbonate (2×20 ml.) and water (2×20 ml.). The organic layer is dried over anhydrous magnesium sulfate, filtered, and stripped to give an oil. This oil is allowed to stand overnight and residual pyridine hydrolyzes the diacylated intermediate to the desired monoacylated product. Flash chromatography (100 g. of Baker 40 mesh silica) eluting with ethyl acetate:hexanes (1:3) gives 455.3 mg. of (−)-3,6-dihydro-4-methyl-6-(3-nitrophenyl)-2-thioxo-1,5(2H)-pyrimidinedicarboxylic acid, 1-ethyl 5-(1-methylethyl) ester as a yellow solid; m.p. 120°-122°; $[\alpha]_{589}^{20}=-57.7°$ (c=1.24, CDCl$_3$) gel; ethyl acetate:hexanes, 1:2) $R_f=0.5$.

Anal. calc'd. for C$_{18}$H$_{21}$N$_3$O$_6$S: C, 53.06; H, 5.20;N, 10.30; S, 7.87. Found: C, 53.23; H, 5.17;N, 10.31; S, 7.81.

EXAMPLE 124

(+)-3,6-Dihydro-4-methyl-6-(3-nitrophenyl)-2-thioxo-1,5(2H)-pyrimidinedicarboxylic acid, 1-ethyl 5-(1-methylethyl) ester Bis(trimethylsilyl)trifluoroacetamide (2.1 eq., 0.82 ml., 3.1 mmole) is added to a mixture of (+)-1,2,3,4-tetrahydro-6-methyl-4-(3-nitrophenyl)-2-thioxo-5-pyrimidinecarboxylic acid, 1-methylethyl ester (500 mg., 1.49 mmole) in pyridine (3 ml.) and tetrahydrofuran (3 ml.) at 0° under nitrogen. After one hour, the bath temperature is reduced to −78° (dry ice/acetone) and a solution of ethyl chloroformate (2.1 eq., 0.3 ml., 3.1 mmole) in tetrahydrofuran (1 ml.) is added dropwise to the mixture. After the addition is completed, the bath is removed and the reaction is stirred to room temperature for one hour. The mixture is then poured into ethyl acetate (10 ml.) and washed with sodium bicarbonate (2×7 ml.) and water (7 ml.). The organic layer is dried over anhydrous magnesium sulfate, filtered, and reduced in vacuo to give the diacylated intermediate. After standing under vacuum overnight in the residual pyridine all the diacylated material had been converted to the desired monoacylated product. Flash chromatography (60 g. Baker 40 mesh silica gel) eluting with ethyl acetate: hexanes (1:3) gives 407 mg. of product as a pale yellow solid. Recrystallization from ethyl acetate:hexanes (1:4) gives 273 mg. of (+)-3,6-dihydro-4-methyl-6-(3-nitrophenyl)-2-thioxo-1,5(2H)-pyrimidinedicarboxylic acid, 1-ethyl 5-(1-methylethyl) ester as a yellow solid; m.p. 120°-121°; $[\alpha]_{589}^{20}=+56.8°$ (c=1, CDCl$_3$). TLC (silica gel; ethyl acetate:hexanes, 1:2) $R_f=0.5$.

Anal. calc'd. for C$_{18}$H$_{21}$N$_3$O$_6$S: C, 53.06; H, 5.20;N, 10.31; S, 7.87. Found: C, 53.41; H, 5.28;N, 10.08; S, 8.07.

EXAMPLE 125

1,2,3,4-Tetrahydro-6-methyl-4-(3-nitrophenyl)-3-(1-oxopropyl)-2-thioxo-5-pyrimidinecarboxylic acid, methyl ester a) 1,6-Dihydro-2-[[(4-methoxyphenyl)methyl]thio]-4-methyl-6-(3-nitrophenyl)-1-(1-oxopropyl)-5 pyrimidinecarboxylic acid, methyl ester 1,4-Dihydro-2-[[(4-methoxyphenyl)methyl]thio]-6-methyl-4-(3-nitrophenyl)-5-pyrimidinecarboxylic acid, methyl ester (1.52 g., 3.5 mmole) in 15 ml of dichloromethane is cooled under argon to 0°-5° C. and treated with propionyl chloride (0.43 g., 4.7 mmole) and pyridine (0.55 g., 7.0 mmole). The mixture is then allowed to stir at room temperature for 3 hours, diluted with ether and the salt is filtered. The filtrate is washed with water, 1N hydrochloric acid, water, aqueous sodium bicarbonate, water and saturated brine. The aqueous fractions are back extracted with fresh ether. The combined organic solutions are dried (magnesium sulfate) and concentrated in vacuo to give 1.6 g. of a viscous oily product.

b) 1,2,3,4-Tetrahydro-6-methyl-4-(3-nitrophenyl)-3-(1-oxopropyl)-2-thioxo-5-pyrimidinecarboxylic acid, methyl ester 1,6-Dihydro-2-[[(4-methoxyphenyl)methyl]thio]-4-methyl-6-(3-nitrophenyl)-1-(1-oxopropyl)-5-pyrimidinecarboxylic acid, methyl ester (1.6 g., 3.3 mmole) in 20 ml of dichloromethane under argon at room temperature is treated with trifluoroacetic acid (0.75 ml., 1.1 g., 9.7 mmole) and ethanethiol (0.4 ml, 0.33 g, 5.4 mmole). After 3 hours, volatiles are evaporated in vacuo and the residue (solidified) is triturated with isopropyl ether to give 0.95 g. of product, m.p. 167°-171°. TLC(silica gel; ethyl acetate:hexanes, 1:1) $R_f=0.50$.

Analysis calc'd. for C$_{16}$H$_{17}$N$_3$O$_5$S: C, 52.88; H, 4.72;N, 11.56; S, 8.82. Found: C, 52.83; H, 4.74;N, 11.45; S, 8.71.

EXAMPLE 126

1,2,3,4-Tetrahydro-6-methyl-4-(3-nitrophenyl)-3-(1-oxo-2-phenylethyl)-2-thioxo-5-pyrimidinecarboxylic acid, methyl ester a) 1,6-Dihydro-2-[[(4-methoxyphenyl)methyl]thio]-4-methyl-6-(3-nitrophenyl)-1-(1-oxo-2-phenylethyl)-5-pyrimidinecarboxylic acid, methyl ester 1,4-Dihydro-2-[[(4-methoxyphenyl)methyl]thio]-6-methyl-4-(3-nitrophenyl)-5-pyrimidinecarboxylic acid, methyl ester (1.52 g., 3.5 mmole) in 15 ml. of dichloromethane is cooled under argon to 0°-5° and treated with pyridine (0.6 ml., 0.55 g., 7.0 mmole) and phenylacetyl chloride (0.72 g., 4.7 mmole). The mixture is then allowed to stir at room temperature for 4 hours; a small amount of starting material remained unchanged during the last two hours.

The reaction mixture is diluted with ether and washed with water, 1N hydrochloric acid, water, sodium bicarbonate, water and saturated brine. The aqueous fractions are backwashed with fresh ether. The combined organic solutions are dried (magnesium sulfate) and concentrated in vacuo to give 1.95 g. of crude oily product. Flash chromatography on 250 ml. of silica gel and elution with ethyl acetate/hexane (1:3) gives 1.25 g. of the title compound.

b)
1,2,3,4-Tetrahydro-6-methyl-4-(3-nitrophenyl)-3-(1-oxo-2-phenylethyl)-2-thioxo-5-pyrimidine-carboxylic acid, methyl ester A solution of 1,6-dihydro-2-[[(4-methoxyphenyl)methyl]thio]-4-methyl-6-(3-nitrophenyl)-1-(1-oxo-2-phenylethyl)-5-pyrimidinecarboxylic acid, methyl ester (1.25 g., 2.25 mmole) in 15 ml. of dichloromethane under argon at room temperature is treated with trifluoroacetic acid (0.6 ml., 0.85 g., 7.7 mmole) and ethanethiol (0.4 ml., 0.33 g., 5.4 mmole). After 4 hours, volatiles are evaporated in vacuo to give a solid residue. Trituration with isopropyl ether gives 0.72 g. of pale yellow powder which is recrystallized from ethyl acetate/isopropyl ether to give 400 mg. of the title compound, m.p. 155°–156.5°. TLC (silica gel; ethyl acetate:hexanes, 1:1) $R_f$=0.46.

Analysis calc'd. for $C_{21}H_{19}N_3O_5S$: C, 59.28; H, 4.50;N, 9.88; S, 7.54. Found: C, 59.21; H, 4.47;N, 9.73; S, 7.12.

EXAMPLE 127

1,2,3,4-Tetrahydro-6-methyl-3-[(4-methoxyphenyl)carbonyl]-4-(3-nitrophenyl)-2-thioxo-5-pyrimidinecarboxylic acid, ethyl ester a)
1,6-Dihydro-2-[[(4-methoxyphenyl)methyl]thio]-4-methyl-6-(3-nitrophenyl)-1-[(4-methoxyphenyl)carbonyl]-5-pyrimidinecarboxylic acid, ethyl ester A solution of 1.5 g. (0.0034 mole) of 1,4-dihydro-2-[[(4-methoxyphenyl)methyl]thio]-6-methyl-4-(3-nitrophenyl)-5-pyrimidinecarboxylic acid, ethyl ester in 10 ml. of dichloromethane containing 0.6 ml. (0.0074 mole) of pyridine is treated gradually with a solution of 0.70 g (0.0041 mole) of p-anisoyl chloride in 10 ml. of dichloromethane. After stirring for 16 hours at room temperature, dichloromethane is added and the solution is washed with water, 1N hydrochloric acid, sodium bicarbonate and brine. The dried solution is evaporated to give 1.8 g. of an impure oil. Flash chromatography using ethyl acetate/hexane (1:3) gives 1.58 g. of yellow oil.

b)
1,2,3,4-Tetrahydro-6-methyl-3-[(4-methoxyphenyl)carbonyl]-4-(3-nitrophenyl)-2-thioxo-5pyrimidinecarboxylic acid, ethyl ester A solution of 1.5 g. (0.0026 mole) of 1,6-dihydro-2-[[(4-methoxyphenyl)methyl]thio]-4-methyl-6-(3-nitrophenyl)-1-[(4-methoxyphenyl)carbonyl]-5-pyrimidinecarboxylic acid, ethyl ester in 15 ml. of dichloromethane is treated with 0.88 ml. (0.0113 mole) of trifluoroacetic acid and 0.38 g. (0.0059 mole) of ethanethiol. After stirring for 48 hours, the solvent is evaporated and the oil residue is triturated with isopropyl ether to form 0.91 g. of the title compound as a yellow solid, m. p. 130°–132°. TLC(silica gel; ethyl acetate hexane, 1:1) $R_f$=0.50.

Anal. calc'd. for $C_{22}H_{21}N_3O_6S$: C, 58.01; H, 4.64;N, 9.22; S, 7.03. Found: C, 57.60; H, 5.01;N, 9.47; S, 6.92.

EXAMPLE 128

1,2,3,4-Tetrahydro-6-methyl-4-(3-nitrophenyl)-3-[(4-nitrophenyl)carbonyl]-2-thioxo-5-pyrimidinecarboxylic acid, ethyl ester a)
1,6-Dihydro-2-[[(4-methoxyphenyl)methyl]thio]-4-methyl-6-(3-nitrophenyl)-1-[(4-nitrophenyl)carbonyl]-5-pyrimidinecarboxylic acid, ethyl ester A solution of 1.5 g. (0.0034 mole) of 1,4-dihydro-2-[[(4-methoxyphenyl)methyl]thio]-6-methyl-4-(3-nitrophenyl)-5-pyrimidinecarboxylic acid, ethyl ester in 10 ml. of dichloromethane is added gradually to a solution of 0.76 g. (0.0041 mole) of p-nitrobenzoyl chloride in 10 ml. of dichloromethane containing 0.6 ml. (0.0074 mole) of pyridine. After stirring for 4 hours at room temperature, dichloromethane is added and the solution is washed with water, 1N hydrochloric acid, sodium bicarbonate and brine. The dried solution is evaporated to give 2.0 g. of an oil. Flash chromatography using ethyl acetate/hexane (1:4) gave a yellow oil. Trituration with isopropyl ether gives 1.32 g. of the title compound as a yellow solid, m. p. 121°–123°.

b)
1,2,3,4-Tetrahydro-6-methyl-4-(3-nitrophenyl)-3-[(4-nitrophenyl)carbonyl]-2-thioxo-5-pyrimidinecarboxylic acid, ethyl ester A solution of 1.3 g. (0.0022 mole) of 1,6-dihydro-2-[[(4-methoxyphenyl)methyl]thio]-4-methyl-6-(3-nitrophenyl)-1-[(4-nitrophenyl)carbonyl]-5pyrimidinecarboxylic acid, ethyl ester, 0.75 ml. (0.0097 mole) of trifluoroacetic acid and 0.32 g. (0.0050 mole) of ethanethiol in 15 ml. of dichloromethane is stirred at room temperature for 24 hours. The solvent is evaporated and the residue is triturated with isopropyl ether to give 0.95 . g of the title compound as a yellow solid, m.p. 139°–141°. TLC (silica gel; ethyl acetate:hexane, 1:1) $R_f$=0.35.

Analysis calc'd. for $C_{21}H_{19}N_3O_5S$: C, 59.27; H, 4.50;N, 9.80; S, 7.53. Found: C, 59.92; H, 4.49;N, 9.79; S, 7.46.

EXAMPLE 129

3-Benzoyl-1,2,3,4-tetrahydro-6-methyl-4-(3-nitrophenyl)-2-thioxo-5-pyrimdinecarboxylic acid, ethyl ester a) 1-Benzoyl-1,6-dihydro-2-[[(4-methoxyphenyl)methyl]thio]-4-methyl-6-(3-nitrophenyl)-5-pyrimidinecarboxylic acid, ethyl ester A cold solution (5°) of 2.0 g. (0.0045 mole) of 1,4-dihydro-2-[[(4-methoxyphenyl)methyl]thio]-6-methyl-4-(3-nitrophenyl)-5-pyrimidinecarboxylic acid, ethyl ester in 25 ml. of dichloromethane containing 0.72 g. (0.0091 mole) of pyridine is treated slowly with a solution of 0.76 g. (0.0054 mole) of benzoyl chloride in 3 ml. of dichloromethane. After stirring at room temperature for 16 hours, the solution is diluted with dichloromethane and washed with water, 1N hydrochloric acid, sodium bicarbonate and brine. The dried solution is evaporated to give 2.37 g. of a viscous oil which is not purified.

b)
3-Benzoyl-1,2,3,4-tetrahydro-6-methyl-4-(3-nitrophenyl)-2-thioxo-5-pyrimidinecarboxylic acid, ethyl ester A solution of 2.2 g. (0.0040 mole) of 1-benzoyl-1,6-dihydro-2-[[(4-methoxyphenyl)methyl]thio-4-methyl-6-(3-nitrophenyl)-5-pyrimidinecarboxylic acid, ethyl ester, 1.53 ml. (0.0198 mole) of trifluoroacetic acid and 0.6 g. (0.0092 mole) of ethanethiol is stirred at room temperature for 24 hours. The solvent is evaporated. Trituration of the oil residue with isopropyl ether gives 1.2 g. of a yellow solid (mixture), m. p. 152°-156°.

This material is dissolved in a small amount of ethyl acetate. Approximately 2.0 g. of silica gel is added and the solvent is evaporated in vacuo to give a dry powder which is placed on a column of silica gel. Flash chromatography using dichloromethane gives 0.55 g. of the title compound as a yellow solid, m. p. 173°-175°. TLC(silica gel; ethyl acetate:hexanes, 1:1) $R_f$=0.60.

Analysis calc'd. for $C_{21}H_{19}N_3O_5S$: C, 59.27; H, 4.50;N, 9.87; S, 7.53. FOUND: C, 58.92; H, 4.49; N, 9.79; S, 7.46.

EXAMPLE 130

1,2,3,4-Tetrahydro-6-methyl-4-(3-nitrophenyl)-3-(1-oxopropyl)-2-oxo-5-pyrimidinecarboxylic acid, ethyl ester A solution of 1,4-dihydro-2-methoxy-6-methyl-4-(3-nitrophenyl)-5-pyrimidinecarboxylic acid, ethyl ester (750 mg., 2.35 mmole) and dry pyridine (0.57 ml., 7.05 mmole) in dichloromethane (5.0 ml.) at −20° (methanol/ice bath) under argon is treated dropwise via gas-tight syringe with propionyl chloride (0.26 ml., 2.82 mmole). The reaction mixture is stirred for 2.0 hours and evaporated. The solid yellow residue is dissolved in methanol (25 ml.) and tetrahydrofuran (15 ml.) and treated with 5N hydrochloric acid (6.0 ml.). After stirring at room temperature for 1.0 hour, the reaction mixture is evaporated. The residue is partitioned between ethyl acetate and sodium bicarbonate solution. The organic phase is washed with saturated sodium chloride, dried over magnesium sulfate, and evaporated. The residue is flash chromatographed to give the title compound as a white foam (567 mg.). This foam is combined with material from another batch (290 mg.) and recrystallized from dichloromethane/isopropyl ether to give large shiny white crystals (784 mg., m. p. 152°-154°). TLC(silica gel; 50% ethyl acetate:hexanes) $R_f$=0.57.

Analysis calc'd. for $C_{17}H_{19}N_3O_6$: C, 56.50; H, 5.30;N, 11.63. Found: C, 56.59; H, 5.25;N, 11.57.

EXAMPLE 131

3-(2,2-Dimethyl-1-oxopropyl)-1,2,3,4-tetrahydro-6-methyl-4-(3-nitrophenyl)-2-oxo-5-pyrimidinecarboxylic acid, ethyl ester A solution of 1,4-dihydro-2-methoxy-6-methyl-4-(3-nitrophenyl)-5-pyrimidinecarboxylic acid, ethyl ester (0.96 g., 3.0 mmole), dry triethylamine (1.25 ml., 9.0 mmole), and dimethylaminopyridine (36 mg., 0.3 mmole) in dichloromethane (12 ml.) under argon is treated with pivaloyl chloride (0.44 ml., 3.6 mmole). After stirring for 45 minutes at room temperature, the reaction mixture is evaporated. The residue is taken up in tetrahydrofuran/methanol (10 ml. each) and treated with 2N hydrochloric acid (6.0 ml., pH 1). After stirring at room temperature for 3.0 hours, the reaction is quenched with saturated sodium bicarbonate, partially evaporated and extracted with ethyl acetate. The organic phase is washed with saturated sodium chloride and evaporated. Flash chromatography and crystallization from dichloromethane/isopropyl ether gives the title compound as white crystals (420 mg. , m. p. 155°-156°. TLC(silica gel; ethyl acetate:hexane, 1:1)$R_f$=0.67.

Analysis calc'd. for $C_{19}H_{23}N_3O_6$: C 58.60; H, 5.95N, 10 79. Found: C, 58.62; H, 5.89;N, 10.64.

Additional compounds prepared according to the procedure of Examples 125-131 and falling within the scope of this invention are:

3-benzyl-1,2,3,4-tetrahydro-6-methyl-4-(3-nitrophenyl)-2-oxo-5-pyrimidinecarboxylic acid, 2-[(methyl)(phenylmethyl)amino]ethyl ester;

4-(4-benzofurazanyl)-1,2,3,4-tetrahydro-6-methyl-2-oxo-3-[1-oxo-3-[4-(phenylmethyl)-1piperazinyl]propyl]-5-pyrimidinecarboxylic acid, ethyl ester;

1,2,3,4-tetrahydro-6-methyl-4-[2-(methylthio)-3-pyridinyl]-2-oxo-3-(1-oxobutyl)-5-pyrimidinecarboxylic acid, ethyl ester;

4-(2-chloro-3-nitrophenyl)-1,2,3,4-tetrahydro-6-methyl-2-oxo-3-(1-oxo-2-methylpropyl)-5-pyrimidinecarboxylic acid, ethyl ester;

4-(2-chlorophenyl)-1,2,3,4-tetrahydro-6-methyl-2-oxo-3-[1-oxo-3-(dimethylamino)propyl-]-5-pyrimidinecarboxylic acid, ethyl ester;

3-benzoyl-1,2,3,4-tetrahydro-6-methyl-4-(3-nitrophenyl)-2-thioxo-5-pyrimidinecarboxylic acid, 2-[(methyl)(phenylmethyl)amino]ethyl ester;

4-(2,3-dichlorophenyl)-1,2,3,4-tetrahydro-6-methyl-3-(1-oxopropyl)-2-thioxo-5-pyrimidinecarboxylic acid, 1-(phenylmethyl)-4-piperidinyl ester;

3-(cyclopentylcarbonyl)-1,2,3,4-tetrahydro-6-methyl-4-(2-nitrophenyl)-2-thioxo-5-pyrimidinecarboxylic acid, 2-[4-(diphenylmethyl)-1-piperazinyl]ethyl ester;

1,2,3,4-tetrahydro-6-methyl-3-[1-oxo-3-[(methyl)(phenylmethyl)amino]propyl]-2-thioxo-4-[2-(trifluoromethyl)phenyl]-5-pyrimidinecarboxylic acid, ethyl ester;

4-(2,1,3-benzoxadiazol-4-yl)-1,2,3,4-tetrahydro-6-methyl-3-[1-oxo-3-[4-(phenylmethyl)-1-piperazinyl]propyl]-2-thioxo-5-pyrimidinecarboxylic acid, ethyl ester;

1,2,3,4-tetrahydro-6-methyl-4-[2-(methylthio)-3-pyridinyl]-3-(1-oxobutyl)-2-thioxo-5pyrimidinecarboxylic acid, ethyl ester;

4-(2,3-dichlorophenyl)-1,2,3,4-tetrahydro-6-methyl-2-oxo-3-(1-oxopropyl)-5-pyrimidinecarboxylic acid, 1-(phenylmethyl)-4-piperidinyl ester;

3-(cyclopentylcarbonyl)-1,2,3,4-tetrahydro-6-methyl-2-oxo-4-(2-nitrophenyl)-5-pyrimidinecarboxylic acid, 2-[4-(diphenylmethyl)-1-piperazinyl]ethyl ester;

1,2,3,4-tetrahydro-6-methyl-2-oxo-3-[1-oxo-3-[(methyl)(phenylmethyl)amino]propyl]-4-[2(trifluoromethyl)phenyl]-5-pyrimidinecarboxylic acid, ethyl ester;

4-(2-chloro-3-nitrophenyl)-1,2,3,4-tetrahydro-6-methyl-3-(1-oxo-2-methylpropyl)-2-thioxo-5-pyrimidinecarboxylic acid, ethyl ester; and 4-(2-chlorophenyl)-1,2,3,4-tetrahydro-6-methyl-3-[1-oxo-3-(dimethylamino)propyl]-2-thioxo-5-pyrimidinecarboxylic acid, ethyl ester.

EXAMPLE 132

1000 tablets each containing the following ingredients:

| | |
|---|---|
| 3,6-Dihydro-4-methyl-6-[2-(trifluoromethyl)phenyl]-2-thioxo-1,5(2H)-pyrimidinedicarboxylic acid, diethyl ester | 100 mg. |
| Cornstarch | 50 mg. |
| Gelatin | 7.5 mg. |
| Avicel(microcrystalline cellulose) | 25 mg |
| Magnesium stearate | 2.5 mg. |
| | 185 mg. | are prepared from sufficient bulk quantities by mixing the 3,6-dihydro-4-methyl-6-[2-(trifluoromethyl)-phenyl]-2-thioxo-1,5(2H)-pyrimidinedicarboxylic acid, diethyl ester and cornstarch with an aqueous solution of the gelatin. The mixture is dried and ground to a fine powder. The Avicel and then the magnesium stearate are admixed with granulation. This mixture is then compressed in a tablet press to form 1000 tablets each containing 100 mg. of active ingredient.

In a similar manner, tablets containing 100 mg. of the product of any of Examples 1 to 54 and 56 to 131 can be prepared.

A similar procedure can be employed to form tablets containing 50 mg. of active ingredient.

EXAMPLE 133

Two piece #1 gelatin capsules are filled with a mixture of the following ingredients:

| | |
|---|---|
| 3,6-Dihydro-4-methyl-6-(3-nitrophenyl)-2-thioxo-1,5(2H)-pyrimidinedicarboxylic acid, diethyl ester | 50 mg. |
| Magnesium stearate | 7 mg. |
| Lactose | 193 mg. |
| | 250 mg. |

In a similar manner capsules containing 50 mg. of the product of any of Examples 2 to 131 can be prepared.

EXAMPLE 134

An injectable solution is prepared as follows:

| | |
|---|---|
| 3,6-Dihydro-4-methyl-6-(3-nitrophenyl)-2-oxo-1,5(2H)-pyrimidinedinedicarboxylic acid, diethyl ester | 500 g. |
| Methyl paraben | 5 g. |
| Propyl paraben | 1 g. |
| Sodium chloride | 25 g. |
| Water for injection | 5 l. |

The active substance, preservatives, and sodium chloride are dissolved in 3 liters of water for injection and then the colume is brought up to 5 liters. The solution is filtered through a sterile filter and aseptically filled into presterilized vials which are closed with presterilized rubber closures. Each vial contains 5 ml. of solution in a concentration of 100 mg. of active ingredient per ml. of solution for injection.

In a similar manner, an injectable solution containing 100 mg. of active ingredient per ml. of solution can be prepared for the product of any of Examples 1 and 3 to 131.

EXAMPLE 135

1000 tablets each containing the following ingredients:

| | |
|---|---|
| 3,6-Dihydro-4-methyl-6-[2-(trifluoromethyl)phenyl]-2-thioxo-1,5(2H)-pyrimidinedicarboxylic acid, diethyl ester | 100 mg. |
| Avicel | 100 mg. |
| Hydrochlorothiazide | 12.5 mg. |
| Lactose | 113 mg. |
| Cornstarch | 17.5 mg. |
| Stearic acid | 7 mg. |
| | 350 mg. | are prepared from sufficient bulk quantities by slugging the 3,6-dihydro-4-methyl-6-[2-(trifluoromethyl)-phenyl]-2-thioxo-1,5(2H)-pyrimidinedicarboxylic acid, diethyl ester, Avicel, and a portion of the stearic acid. The slugs are ground and passed through a #2 screen, then mixed with the hydrochlorothiazide, lactose, cornstarch, and remainder of the stearic acid. The mixture is compressed into 350 mg. capsule shaped tablets in a tablet press. The tablets are scored for dividing in half.

In similar manner, tablets can be prepared containing 100 mg. of the product of any of Examples 1 to 54 and 56 to 131.

What is claimed is:

1. A compound of the formula

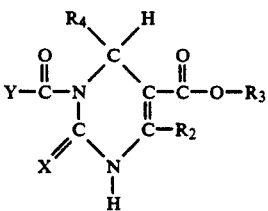

including a pharmaceutically acceptable salt thereof wherein:

X is oxygen or sulfur;

Y is $R_{11}$ or $—O—R_1$;

$R_1$ is lower alkyl, aryl, cycloalkyl, $-A_1$-aryl, $-A_1$-cycloalkyl, $-A_1$-heterocyclo, $-A_2$—OH, $-A_2$—O—lower alkyl, $-A_2$—O—$(CH_2)_m$-aryl, $-A_2$—SH, $-A_2$—S—lower alkyl, $-A_2$—S—$(CH_2)_m$-aryl,

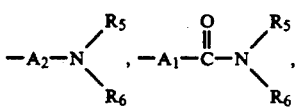

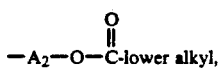

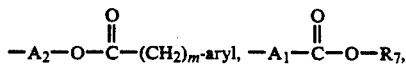

halo substituted lower alkyl,

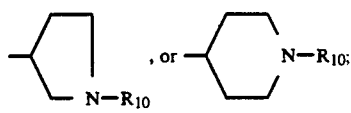

$R_2$ is hydrogen, lower alkyl, lower alkenyl, lower alkynyl, cycloalkyl, aryl, -$A_1$-cycloalkyl, -$A_1$-aryl, -$A_1$-heterocyclo, -$A_1$—OH, -$A_1$—O—lower alkyl, -$A_1$—O—(CH$_2$)$_m$-aryl, -$A_1$—SH, -$A_1$—S—lower alkyl, -$A_1$—S—(CH$_2$)$_m$-aryl,

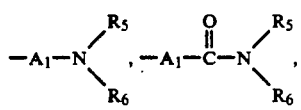

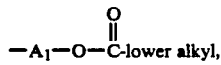

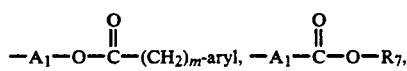

or halo substituted lower alkyl;
$R_3$ is hydrogen, lower alkyl, aryl, cycloalkyl, -$A_1$-aryl, -$A_1$-cycloalkyl, -$A_1$-heterocyclo, -$A_2$—OH, -$A_2$—O—lower alkyl, -$A_2$—O—(CH$_2$)$_m$-aryl, -$A_2$—SH, -$A_2$—S—lower alkyl, -$A_2$—S—(CH$_2$)$_m$-aryl,

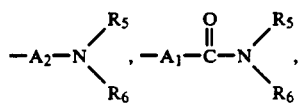

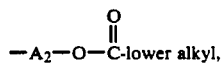

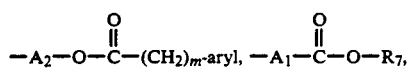

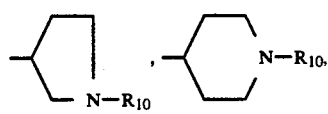

substituted lower alkyl, or a pharmaceutically acceptable salt forming ion;
$R_4$ is heterocyclo or aryl;
$R_5$ and $R_6$ are independently selected from the group consisting of hydrogen, lower alkyl, —(CH$_2$)$_m$-aryl,

or $R_5$ and $R_6$ taken together with the N-atom to which they are attached complete a heterocyclic ring of the formula

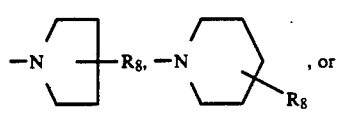

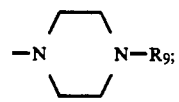

$R_7$ is hydrogen, lower alkyl, —(CH$_2$)$_m$—aryl or a pharmaceutically acceptable salt forming ion;
$R_8$ is hydrogen, lower alkyl of 1 to 4 carbons, lower alkoxy of 1 to 4 carbons, lower alkylthio of 1 to 4 carbons, halo, CF$_3$, nitro, or hydroxy;
$R_9$ is hydrogen, lower alkyl of 1 to 4 carbons,

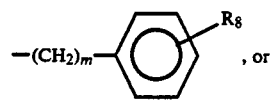

$R_{10}$ is lower alkyl of 1 to 4 carbons,

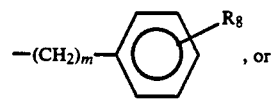

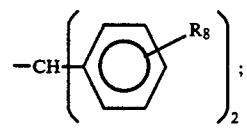

$R_{11}$ is lower alkyl, aryl, cycloalkyl, heterocyclo, -$A_1$-aryl, -$A_1$-cycloalkyl, -$A_1$-heterocyclo, -$A_1$-OH, -$A_1$—O—lower alkyl, -$A_1$—O—(CH$_2$)$_m$—aryl, -$A_1$—SH, -$A_1$—S—lower alkyl, -$A_1$—S—(CH$_2$)$_m$—aryl,

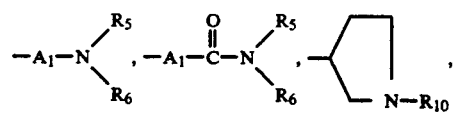

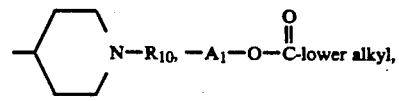

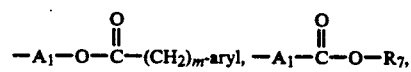

or halo substituted lower alkyl;

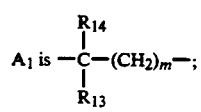

-continued

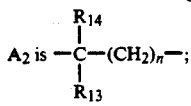

m is zero or an integer from 1 to 6;
n is an integer from 1 to 6;
R$_{13}$ and R$_{14}$ are independently selected from the group consisting of hydrogen, lower alkyl of 1 to 4 carbons,

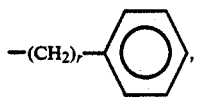

and —(CH$_2$)$_r$—cycloalkyl;
r is zero or an integer from 1 to 3;
the term "lower alkyl" refers to straight or branched chain hydrocarbon radicals of one to eight carbons;
the term "lower alkenyl" refers to straight or branched chain hydrocarbon radicals of two to eight carbons with one double bond;
the term "lower alkynyl" refers to straight or branched chain hydrocarbon radicals of two to eight carbons with one triple bond;
the term "cycloalkyl" refers to saturated rings of 4 to 7 carbons;
the term "halo" refers to chloro, bromo, and fluoro;
the term "aryl" refers to phenyl, 1-naphthyl, 2-naphthyl, mono substituted phenyl, 1-naphthyl or 2-naphthyl wherein said substituent is lower alkyl of 1 to 4 carbons, lower alkoxy of 1 to 4 carbons, lower alkylthio of 1 to 4 carbons, halo, nitro, cyano, hydroxy, amino, —NH—alkyl wherein alkyl is of 1 to 4 carbons, —N(alkyl)$_2$ wherein alkyl is of 1 to 4 carbons, —CF$_3$, —NCS, —OCHF$_2$,

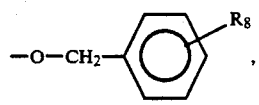

—O—CH$_2$—cycloalkyl,

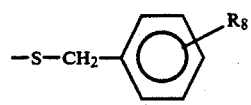

or
—S—CH$_2$-cycloalkyl, and di-substituted phenyl, 1-naphthyl, or 2-naphthyl wherein said substituents are selected from the group consisting of methyl, ethoxy, methylthio, halo, CF$_3$, nitro, amino, and OCHF$_2$; and
the term "heterocyclo" refers to 2- or 3-thienyl, 2-or 3-furyl, 2-, 3- or 4-pyridinyl, imidazolyl, 4-, 5-, 6-, or 7-indolyl, 4-, 5-, 6-, or 7-isoindolyl, 5-, 6-, 7, or 8-quinolinyl, 5-, 6-, 7- , or 8-isoquinolinyl, 4-, 5-, 6- or 7-benzothiazolyl, 4-, 5-, 6-, or 7-benzoxazolyl, 4-, 5-, 6-, or 7-benzimidazolyl, 4-, 5-, 6-, or 7-benzoxadiazolyl, 4-, 5-, 6-, or 7-benzofuranyl, and substituted 2-, 3- or 4-pyridinyl wherein said substituent is methyl, methoxy, or methylthio.

2. A compound of claim 1 wherein:
the term "aryl" refers to phenyl, mono substituted phenyl wherein said substituent is lower alkyl of 1 to 4 carbons, lower alkoxy of 1 to 4 carbons, lower alkylthio of 1 to 4 carbons, halo, nitro, cyano, hydroxy, amino, -NH-alkyl wherein alkyl is of 1 to 4 carbons, —N(alkyl)$_2$ wherein alkyl is of 1 to 4 carbons, CF$_3$, —OCHF$_2$, or

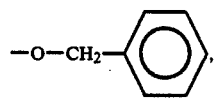

and di-substituted phenyl wherein said substituents are selected from the group consisting of methyl, methoxy, methylthio, halo, —CF$_3$, nitro, amino, and —OCHF$_2$.
3. A compound of claim 2 wherein:
Y is —O—R$_1$.
4. A compound of claim 3 wherein
R$_1$ is straight or branched chain lower alkyl of 1 to 5 carbons, benzyl,

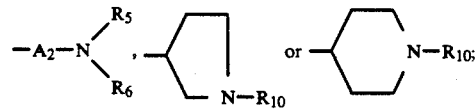

R$_2$ is straight or branched chain lower alkyl of 1 to 5 carbons;
R$_3$ is straight or branched chain lower alkyl of 1 to 5 carbons, benzyl,

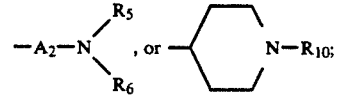

R$_4$ is mono substituted phenyl wherein substituent is selected from the group consisting of lower alkyl of 1 to 4 carbons, halo, CF$_3$, and nitro, disubstituted phenyl wherein said substituents are selected from the group consisting of methyl, halo, CF$_3$, and nitro, 2-, 3-, or 4- pyridinyl, 2-methylthio-3-pyridinyl, or 2,1,3-benzoxadiazolyl;
A$_2$ is -(CH$_2$)-(CH$_2$)$_n$— or —CH—(CH$_2$)$_n$—;
|
CH$_3$ R$_5$ and R$_6$ are independently selected from the group consisting of hydrogen, straight or branched chain lower alkyl of 1 to 5 carbons, and benzyl or R$_5$ and R$_6$ taken together with the N atom to which they are attached complete a heterocyclic ring of the formula

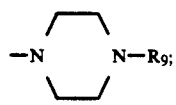

R$_9$ is methyl, benzyl, or diphenylmethyl; and
R$_{10}$ is benzyl or diphenylmethyl.

5. A compound of claim 4 wherein:
$R_2$ is methyl.
6. A compound of claim 5 wherein
$R_1$ is methyl, ethyl, isopropyl, benzyl,

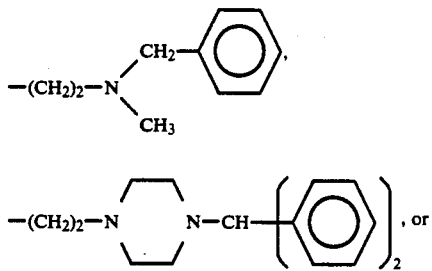

$R_3$ is ethyl, isopropyl, benzyl,

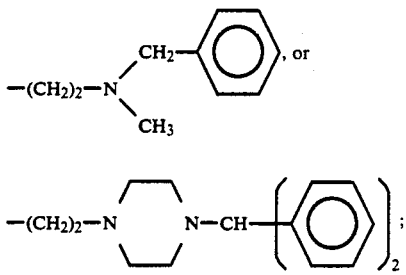

and
$R_4$ is 2-nitrophenyl, 3-nitrophenyl, 2-chlorophenyl, 3-chlorophenyl, 2-(trifluoromethyl)phenyl, 3-(trifluoromethyl)phenyl, 2,3-dichlorophenyl, or 2-chloro-3-nitrophenyl or 4-(2,1,3-benzoxadiazol)-yl.
7. A compound of claim 6 wherein:
X is sulfur.
8. The compound of claim 7 wherein:
$R_1$ is isopropyl;
$R_3$ is

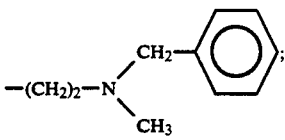

and
$R_4$ is 3-nitrophenyl.
9. The compound of claim 7 wherein:
$R_1$ is

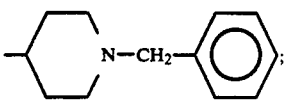

$R_3$ is ethyl;
$R_4$ is 2-nitrophenyl.
10. The compound of claim 7 wherein:

$R_1$ is

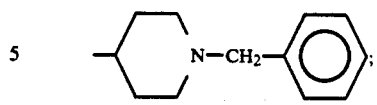

$R_5$ is ethyl;
$R_4$ is 2-(trifluoromethyl)phenyl.
11. A compound of claim 6 wherein:
X is oxygen.
12. The compound of claim 11 wherein:
$R_1$ and $R_3$ are both isopropyl; and
$R_4$ is 3-nitrophenyl.
13. The compound of claim 11 wherein:
$R_1$ is

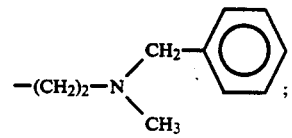

$R_3$ is ethyl; and
$R_4$ is 3-nitrophenyl.
14. The compound of claim 11 wherein:
$R_1$ is

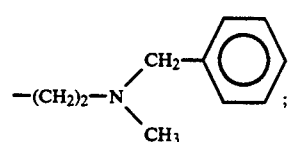

$R_3$ is isopropyl; and
$R_4$ is 3-nitrophenyl.
15. The compound of claim 11 wherein:
$R_1$ is

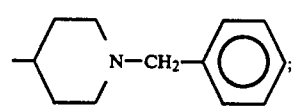

$R_3$ is isopropyl; and
$R_4$ is 3-nitrophenyl.
16. The compound of claim 11 wherein:
$R_1$ is isopropyl;
$R_3$ is

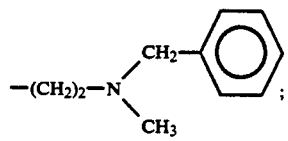

and
$R_4$ is 3-nitrophenyl.
17. A compound of claim 7 wherein:
at least one of $R_1$ and $R_3$ is ethyl or isopropyl; and
$R_4$ is 3-nitrophenyl, 2,3-dichlorophenyl, 2-chloro-3-nitrophenyl, 2-nitrophenyl, or 2-(trifluoromethyl)phenyl.
18. A compound of claim 2 wherein:

Y is $R_{11}$.

19. A compound of claim 18 wherein:
$R_{11}$ is straight or branched chain lower alkyl of 1 to 5 carbons,

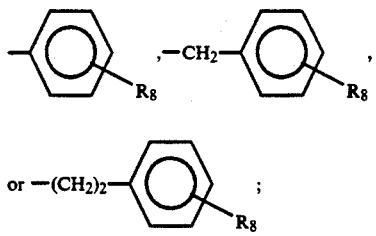

$R_2$ is straight or branched chain lower alkyl of 1 to 5 carbons;
$R_3$ is straight or branched chain lower alkyl of 1 to 5 carbons;
$R_4$ is mono substituted phenyl wherein said substituent is selected from the group consisting of lower alkyl of 1 to 4 carbons, halo, $CF_3$ and nitro, disubstituted phenyl wherein said substituents are selected from the group consisting of methyl, halo, $CF_3$ and nitro, or 2,1,3-benzoxadiazolyl; and
$R_8$ is hydrogen, methyl, methoxy, methylthio, halo, $CF_3$, nitro, or hydroxy.

20. A compound of claim 19 wherein
$R_2$ is methyl.

21. A compound of claim 20 wherein
$R_{11}$ is ethyl, isopropyl, phenyl, 4-methoxyphenyl 4-nitrophenyl, or benzyl;
$R_3$ is methyl or ethyl; and
$R_4$ is 3-nitrophenyl.

22. A compound of claim 21 wherein X is sulfur.
23. A compound of claim 21 wherein X is oxygen.
24. A compound having the structural formula

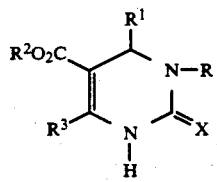

wherein:
X is O or S;
R is COY wherein Y is $C_1$-$C_8$ alkyl or $C_1$-$C_8$ alkoxy;
$R^1$ is aryl of 6 carbon atoms or substituted aryl wherein the substituent is selected from $C_1$-$C_4$ alkyl, $C_1$-$C_4$ alkoxy, $C_1$-$C_4$ alkylthio, $CF_3$, cyano, nitro or halo and disubstituted aryl wherein said substituents are methyl, methoxy, methylthio, $CF_3$, halo, or nitro;
$R^2$ and $R^3$ are $C_1$-$C_8$ alkyl.

25. A pharmaceutical composition useful in the treatment of cardiovascular disease comprising a pharmaceutically acceptable carrier and a nontoxic $Ca^{++}$ controlling amount of a compound represented by the structural formula as defined in claim 24.

26. A method of treatment for cardiovascular disorders which comprises administering to a subject in need of such treatment a non-toxic $Ca^{++}$ controlling amount of a compound of the structural formula as defined in claim 24.

27. A composition useful in reducing blood pressure in a mammal comprising a pharmaceutically acceptable carrier and an anti-hypertensively effective amount of a compound or pharmaceutically acceptable salt thereof of the formula :

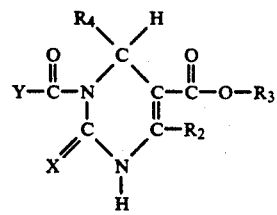

wherein X, Y, $R_2$ and $R_5$ are as defined in claim 1 and $R_4$, is aryl or heterocyclo as defined in claim 1.

28. The composition of claim 27 wherein:
$R_4$ is mono substituted phenyl wherein said substituent is selected from the group consisting of lower alkyl of 1 to 4 carbons, lower alkoxy of 1 to 4 carbons, lower alkylthio of 1 to 4 carbons, halo, $CF_3$, cyano, nitro, benzyloxy, and —$OCHF_2$, disubstituted phenyl wherein said substituents are selected from the group consisting of methyl, methoxy, methylthio, halo, $CF_3$, and nitro.

29. The composition of claim 27 wherein:
$R_4$ is 2-, 3-, or 4-pyridinyl, 2-methylthio-3-pyridinyl, or 2,1,3-benoxadiazolyl.

30. The method of reducing blood pressure in a mammal comprising administering an anti-hypertensively effective amount of the composition of claim 27.

* * * * *